United States Patent
Jong et al.

(10) Patent No.: US 11,124,555 B2
(45) Date of Patent: Sep. 21, 2021

(54) FUSION POLYPEPTIDES COMPRISING ONE OR MORE INCLUSION BODY TAGS, METHODS AND USES

(71) Applicant: Abera Bioscience AB, Stockholm (SE)

(72) Inventors: Wouter Simon Petrus Jong, Stockholm (SE); Joen Luirink, Stockholm (SE)

(73) Assignee: ABERA BIOSCIENCE AB, Stockholm (SE)

( * ) Notice: Subject to any disclaimer, the term of this patent is extended or adjusted under 35 U.S.C. 154(b) by 0 days.

(21) Appl. No.: 16/480,658

(22) PCT Filed: Jan. 29, 2018

(86) PCT No.: PCT/EP2018/052093
§ 371 (c)(1),
(2) Date: Jul. 24, 2019

(87) PCT Pub. No.: WO2018/138316
PCT Pub. Date: Aug. 2, 2018

(65) Prior Publication Data
US 2019/0359671 A1 Nov. 28, 2019

(30) Foreign Application Priority Data
Jan. 27, 2017 (EP) .................................... 17153605

(51) Int. Cl.
*C07K 14/54* (2006.01)
*C07K 14/47* (2006.01)
*C07K 14/485* (2006.01)
*C12N 1/20* (2006.01)

(52) U.S. Cl.
CPC ...... *C07K 14/5403* (2013.01); *C07K 14/4723* (2013.01); *C07K 14/485* (2013.01); *C12N 1/20* (2013.01); *C07K 2319/02* (2013.01); *C07K 2319/034* (2013.01); *C07K 2319/50* (2013.01)

(58) Field of Classification Search
CPC ............ C07K 2319/00; C07K 2319/02; C07K 2319/10; C07K 2319/50
See application file for complete search history.

(56) References Cited

U.S. PATENT DOCUMENTS

| | | |
|---|---|---|
| 2007/0026012 A1 | 2/2007 | DeLisa et al. |
| 2009/0029420 A1 | 1/2009 | Decarolis et al. |
| 2015/0037842 A1* | 2/2015 | Robinson ............... C12P 21/02 435/69.3 |

FOREIGN PATENT DOCUMENTS

| | | | |
|---|---|---|---|
| CN | 103756989 A | 4/2014 | |
| WO | WO 2011/057237 A1 | 5/2011 | |
| WO | WO-2014205518 A1 * | 12/2014 | ............. G01N 33/68 |

OTHER PUBLICATIONS

Thomas et all. "Export of active green fluorescent protein to the periplasm by the twin-arginine translocase pathway in *Escherichia coli*", Molecular Microbiology, 2001, 46-53 (Year: 2001).*
DeLisa et al., "Folding quality control in the export of proteins by the bacterial twin-arginine translocation pathway", Proceedings National Academy of Sciences, PNAS, 2003, 100(10): 6115-6120.
Lim et al., "Mining mammalian genomes for folding competent proteins using Tat-dependent genetic selection in *Escherichia coli*", Protein Science, 2009, 18(12): 2537-2549.
Jong et al., "Application of an *E. coli* signal sequence as a versatile inclusion body tag", Microbial Cell Factories, 2017, 16:50.
Huang et al., "A comparative study on the secretion of alkaline phosphatase in *Escherichia coli*", Journal of the Taiwan Institute of Chemical Engineers, 2009, 40(1): 29-35.
Chou et al., "Polymeric Sequences Reveal a Functional Interrelationship between Hydrophobicity and Length of Signal Peptides", The Journal of Biological Chemistry, 1990, 265(5): 2873-2880.
Mohanty et al., "Membrane protein expression and production: effects of polyhistidine tag length and position", Protein Expression and Purification, 2004, 33: 311-325.
Sauri et al., "Autotransporter β-Domains Have a Specific Function in Protein Secretion beyond Outer-Membrane Targeting", Journal of Molecular Biology, 2011, 412: 553-567.
Speretta et al., "Expression in *Drosophila* of Tandem Amyloid β Peptides Provides Insights into Links between Aggregation and Neurotoxicity", The Journal of Biological Chemistry, 2012, 287(24): 20748-20754.
Sukharev et al., "Stoichiometry of the Large Conductance Bacterial Mechanosensitive Channel of *E. coli*. A Biochemical Study", The Journal of Membrane Biology, 1999, 171: 183-193.

* cited by examiner

*Primary Examiner* — Lianko G Garyu
(74) *Attorney, Agent, or Firm* — James S. Keddie; Bozicevic, Field & Francis LLP

(57) ABSTRACT

A fusion polypeptide, comprising an inclusion body tag fused to at least one polypeptide of interest, is provided. The inclusion body tag comprises an inclusion body forming (IBF) amino acid sequence selected from $X_{14}X_{15}AX_{17}X_{18}X_{19}$GLTVA GMLG and sequences having at least 71% identity thereto. Also provided are inclusion bodies comprising the fusion polypeptide, as well as nucleic acids, expression vectors, host cells and methods for its production.

20 Claims, 20 Drawing Sheets
Specification includes a Sequence Listing.

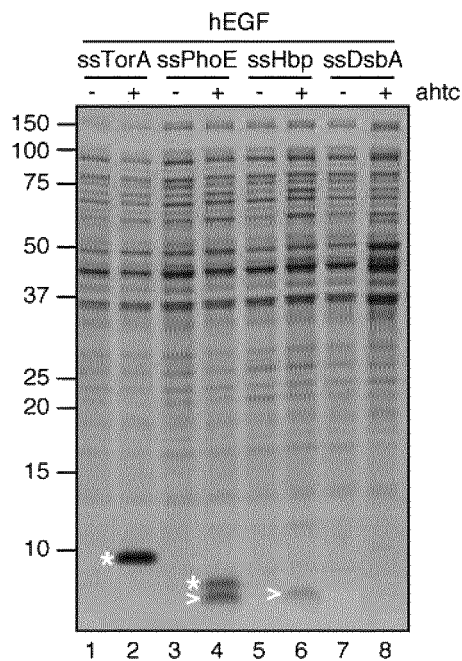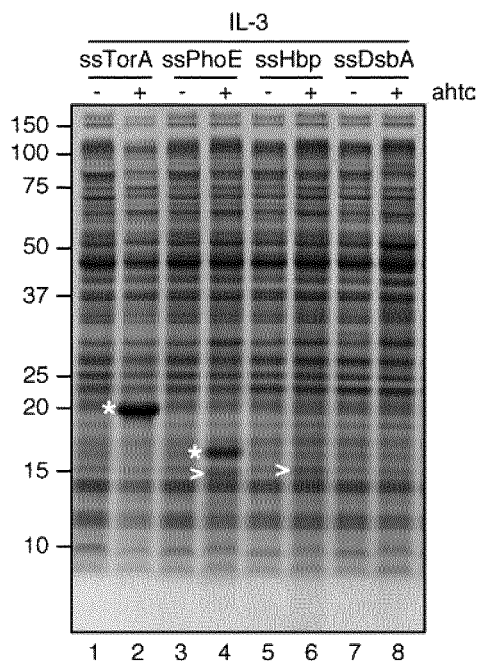
Fig. 5A  Fig. 5B
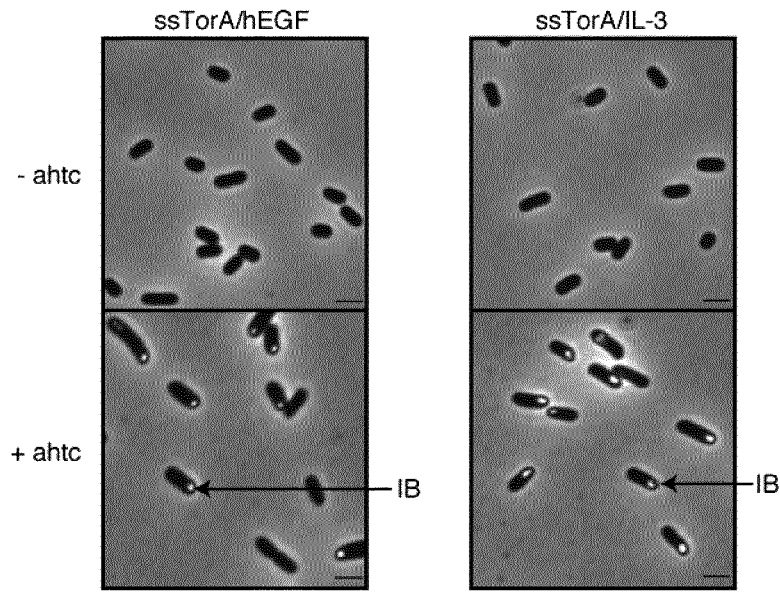
Fig. 6A  Fig. 6B

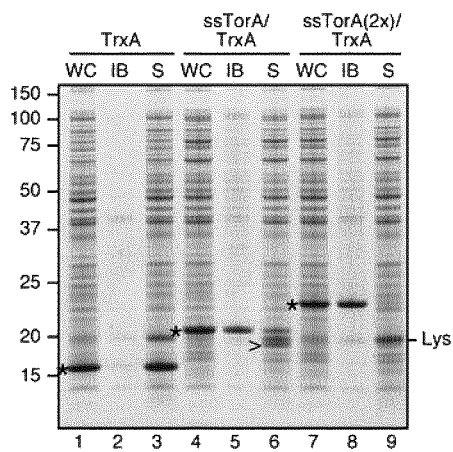 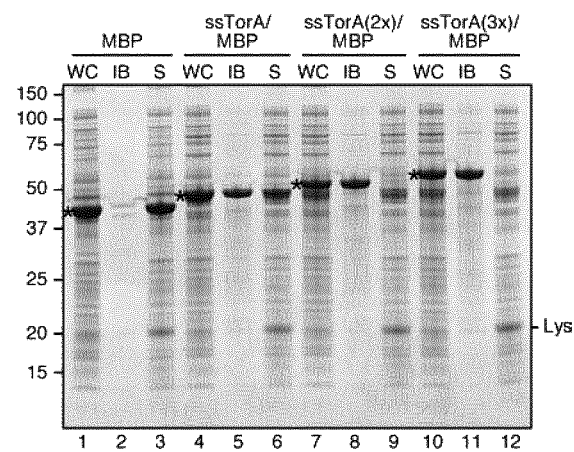
Fig. 7A  Fig. 7B
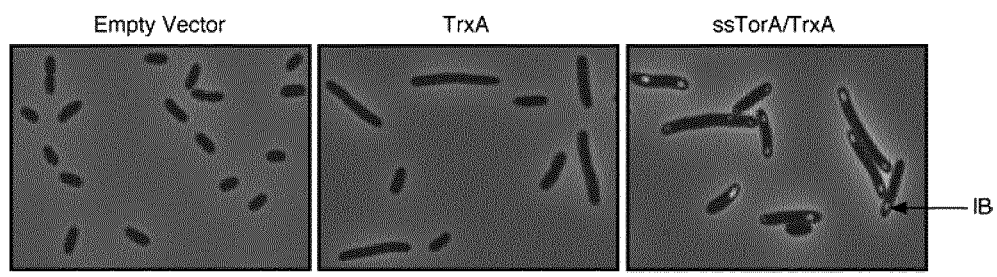
Fig. 8A  Fig. 8B  Fig. 8C

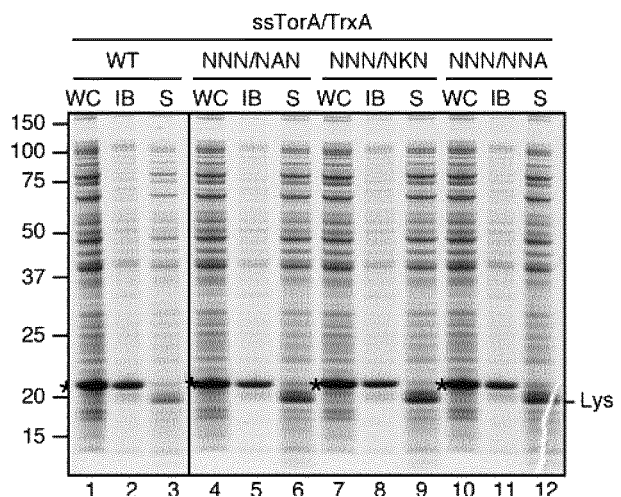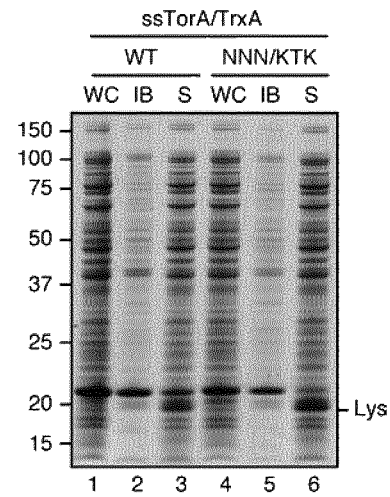
Fig. 11A  Fig. 11B
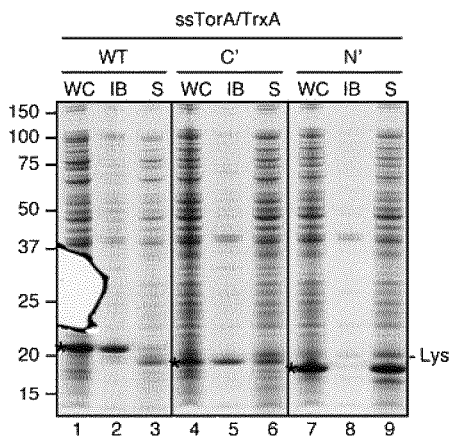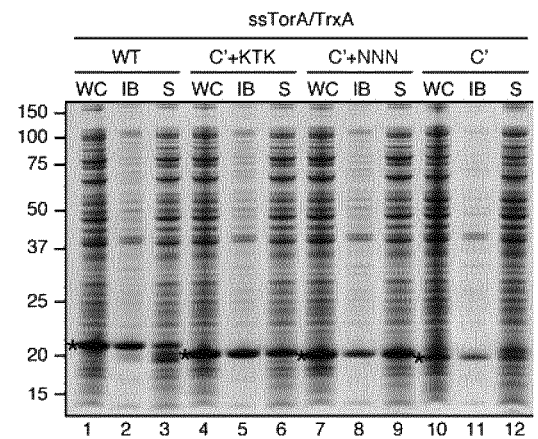
Fig. 12A  Fig. 12B

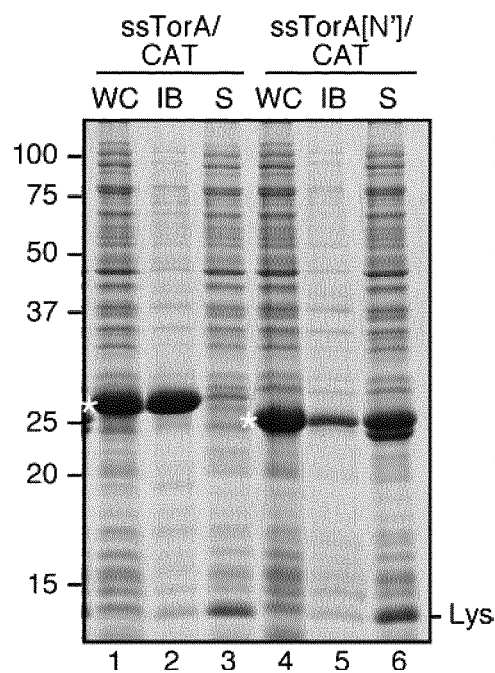
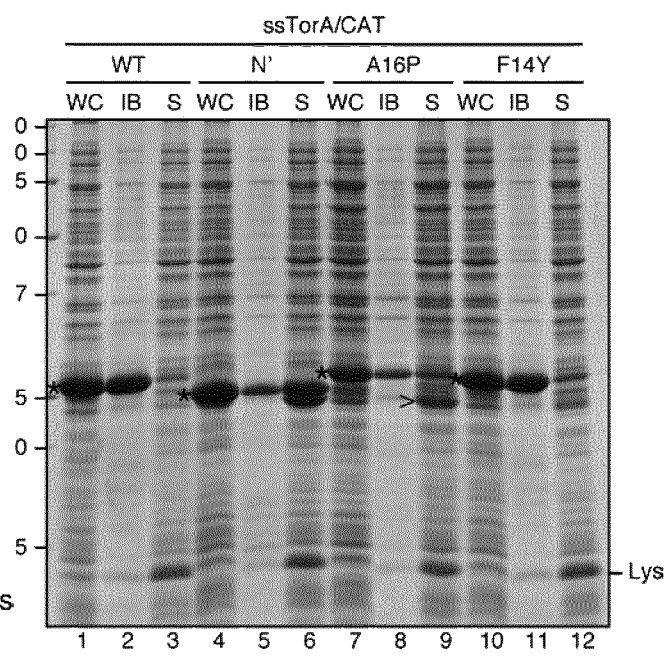
Fig. 17
Fig. 18
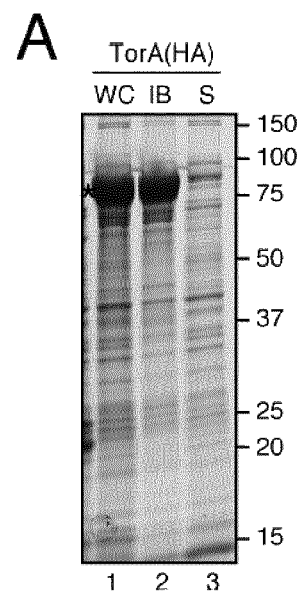
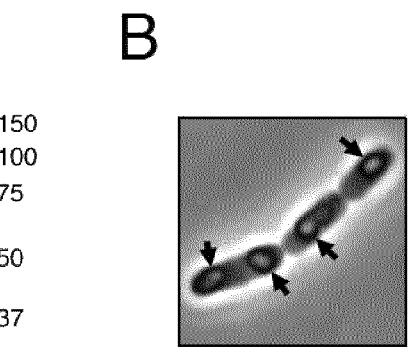
Fig. 19

SEQUENCE LISTING

```
<160> NUMBER OF SEQ ID NOS: 59

<210> SEQ ID NO 1
<211> LENGTH: 15
<212> TYPE: PRT
<213> ORGANISM: Artificial sequence
<220> FEATURE:
<223> OTHER INFORMATION: Fusion tag
<220> FEATURE:
<221> NAME/KEY: VARIANT
<222> LOCATION: (1)..(1)
<223> OTHER INFORMATION: F or Y
<220> FEATURE:
<221> NAME/KEY: VARIANT
<222> LOCATION: (2)..(2)
<223> OTHER INFORMATION: L or M
<220> FEATURE:
<221> NAME/KEY: VARIANT
<222> LOCATION: (4)..(4)
<223> OTHER INFORMATION: Q or E
<220> FEATURE:
<221> NAME/KEY: VARIANT
<222> LOCATION: (5)..(5)
<223> OTHER INFORMATION: L, V or I
<220> FEATURE:
<221> NAME/KEY: VARIANT
<222> LOCATION: (6)..(6)
<223> OTHER INFORMATION: G or V

<400> SEQUENCE: 1

Xaa Xaa Ala Xaa Xaa Xaa Gly Leu Thr Val Ala Gly Met Leu Gly
1               5                   10                  15

<210> SEQ ID NO 2
<211> LENGTH: 19
<212> TYPE: PRT
<213> ORGANISM: Artificial sequence
<220> FEATURE:
<223> OTHER INFORMATION: Fusion tag
<220> FEATURE:
<221> NAME/KEY: VARIANT
<222> LOCATION: (2)..(2)
<223> OTHER INFORMATION: R, C, K, A, S or H
<220> FEATURE:
<221> NAME/KEY: VARIANT
<222> LOCATION: (3)..(3)
<223> OTHER INFORMATION: R, Q, K, A or L
<220> FEATURE:
<221> NAME/KEY: VARIANT
<222> LOCATION: (5)..(5)
<223> OTHER INFORMATION: F or Y
<220> FEATURE:
<221> NAME/KEY: VARIANT
```

```
<222> LOCATION: (6)..(6)
<223> OTHER INFORMATION: L or M
<220> FEATURE:
<221> NAME/KEY: VARIANT
<222> LOCATION: (8)..(8)
<223> OTHER INFORMATION: Q or E
<220> FEATURE:
<221> NAME/KEY: VARIANT
<222> LOCATION: (9)..(9)
<223> OTHER INFORMATION: L, V or I
<220> FEATURE:
<221> NAME/KEY: VARIANT
<222> LOCATION: (10)..(10)
<223> OTHER INFORMATION: G or V

<400> SEQUENCE: 2

Ser Xaa Xaa Arg Xaa Xaa Ala Xaa Xaa Xaa Gly Leu Thr Val Ala Gly
1               5                   10                  15

Met Leu Gly

<210> SEQ ID NO 3
<211> LENGTH: 39
<212> TYPE: PRT
<213> ORGANISM: Artificial sequence
<220> FEATURE:
<223> OTHER INFORMATION: Fusion tag

<400> SEQUENCE: 3

Met Asn Asn Asn Asp Leu Phe Gln Ala Ser Arg Arg Arg Phe Leu Ala
1               5                   10                  15

Gln Leu Gly Gly Leu Thr Val Ala Gly Met Leu Gly Pro Ser Leu Leu
                20                  25                  30

Thr Pro Arg Arg Ala Ser Ala
            35

<210> SEQ ID NO 4
<211> LENGTH: 39
<212> TYPE: PRT
<213> ORGANISM: Artificial sequence
<220> FEATURE:
<223> OTHER INFORMATION: Fusion tag

<400> SEQUENCE: 4

Met Asn Asn Asn Asp Leu Phe Gln Ala Ser Lys Lys Arg Phe Leu Ala
1               5                   10                  15

Gln Leu Gly Gly Leu Thr Val Ala Gly Met Leu Gly Pro Ser Leu Leu
                20                  25                  30

Thr Pro Arg Arg Ala Ser Ala
            35

<210> SEQ ID NO 5
<211> LENGTH: 39
<212> TYPE: PRT
<213> ORGANISM: Artificial sequence
<220> FEATURE:
<223> OTHER INFORMATION: Fusion tag

<400> SEQUENCE: 5

Met Asn Asn Asn Asp Leu Phe Gln Ala Ser Ala Ala Arg Phe Leu Ala
1               5                   10                  15

Gln Leu Gly Gly Leu Thr Val Ala Gly Met Leu Gly Pro Ser Leu Leu
                20                  25                  30

Thr Pro Arg Arg Ala Ser Ala
            35
```

<210> SEQ ID NO 6
<211> LENGTH: 39
<212> TYPE: PRT
<213> ORGANISM: Artificial sequence
<220> FEATURE:
<223> OTHER INFORMATION: Fusion tag

<400> SEQUENCE: 6

Met Asn Ala Asn Asp Leu Phe Gln Ala Ser Arg Arg Arg Phe Leu Ala
1               5                   10                  15

Gln Leu Gly Gly Leu Thr Val Ala Gly Met Leu Gly Pro Ser Leu Leu
            20                  25                  30

Thr Pro Arg Arg Ala Ser Ala
        35

<210> SEQ ID NO 7
<211> LENGTH: 39
<212> TYPE: PRT
<213> ORGANISM: Artificial sequence
<220> FEATURE:
<223> OTHER INFORMATION: Fusion tag

<400> SEQUENCE: 7

Met Asn Lys Asn Asp Leu Phe Gln Ala Ser Arg Arg Arg Phe Leu Ala
1               5                   10                  15

Gln Leu Gly Gly Leu Thr Val Ala Gly Met Leu Gly Pro Ser Leu Leu
            20                  25                  30

Thr Pro Arg Arg Ala Ser Ala
        35

<210> SEQ ID NO 8
<211> LENGTH: 39
<212> TYPE: PRT
<213> ORGANISM: Artificial sequence
<220> FEATURE:
<223> OTHER INFORMATION: Fusion tag

<400> SEQUENCE: 8

Met Asn Asn Ala Asp Leu Phe Gln Ala Ser Arg Arg Arg Phe Leu Ala
1               5                   10                  15

Gln Leu Gly Gly Leu Thr Val Ala Gly Met Leu Gly Pro Ser Leu Leu
            20                  25                  30

Thr Pro Arg Arg Ala Ser Ala
        35

<210> SEQ ID NO 9
<211> LENGTH: 39
<212> TYPE: PRT
<213> ORGANISM: Artificial sequence
<220> FEATURE:
<223> OTHER INFORMATION: Fusion tag

<400> SEQUENCE: 9

Met Lys Thr Lys Asp Leu Phe Gln Ala Ser Arg Arg Arg Phe Leu Ala
1               5                   10                  15

Gln Leu Gly Gly Leu Thr Val Ala Gly Met Leu Gly Pro Ser Leu Leu
            20                  25                  30

Thr Pro Arg Arg Ala Ser Ala
        35

<210> SEQ ID NO 10
<211> LENGTH: 16

```
<212> TYPE: PRT
<213> ORGANISM: Artificial sequence
<220> FEATURE:
<223> OTHER INFORMATION: Fusion tag

<400> SEQUENCE: 10

Met Asn Asn Asp Leu Phe Gln Ala Ser Arg Arg Arg Ala Ser Ala
1               5                   10                  15

<210> SEQ ID NO 11
<211> LENGTH: 27
<212> TYPE: PRT
<213> ORGANISM: Artificial sequence
<220> FEATURE:
<223> OTHER INFORMATION: Fusion tag

<400> SEQUENCE: 11

Met Phe Leu Ala Gln Leu Gly Gly Leu Thr Val Ala Gly Met Leu Gly
1               5                   10                  15

Pro Ser Leu Leu Thr Pro Arg Arg Ala Ser Ala
            20                  25

<210> SEQ ID NO 12
<211> LENGTH: 30
<212> TYPE: PRT
<213> ORGANISM: Artificial sequence
<220> FEATURE:
<223> OTHER INFORMATION: Fusion tag

<400> SEQUENCE: 12

Met Asn Asn Asn Phe Leu Ala Gln Leu Gly Gly Leu Thr Val Ala Gly
1               5                   10                  15

Met Leu Gly Pro Ser Leu Leu Thr Pro Arg Arg Ala Ser Ala
            20                  25                  30

<210> SEQ ID NO 13
<211> LENGTH: 30
<212> TYPE: PRT
<213> ORGANISM: Artificial sequence
<220> FEATURE:
<223> OTHER INFORMATION: Fusion tag

<400> SEQUENCE: 13

Met Lys Thr Lys Phe Leu Ala Gln Leu Gly Gly Leu Thr Val Ala Gly
1               5                   10                  15

Met Leu Gly Pro Ser Leu Leu Thr Pro Arg Arg Ala Ser Ala
            20                  25                  30

<210> SEQ ID NO 14
<211> LENGTH: 34
<212> TYPE: PRT
<213> ORGANISM: Artificial sequence
<220> FEATURE:
<223> OTHER INFORMATION: Fusion tag

<400> SEQUENCE: 14

Met Asn Asn Asn Ser Arg Arg Arg Phe Leu Ala Gln Leu Gly Gly Leu
1               5                   10                  15

Thr Val Ala Gly Met Leu Gly Pro Ser Leu Leu Thr Pro Arg Arg Ala
            20                  25                  30

Ser Ala

<210> SEQ ID NO 15
<211> LENGTH: 29
```

```
<212> TYPE: PRT
<213> ORGANISM: Artificial sequence
<220> FEATURE:
<223> OTHER INFORMATION: Fusion tag

<400> SEQUENCE: 15

Met Asn Asn Asn Leu Ala Gln Leu Gly Gly Leu Thr Val Ala Gly Met
1               5                   10                  15

Leu Gly Pro Ser Leu Leu Thr Pro Arg Arg Ala Ser Ala
            20                  25

<210> SEQ ID NO 16
<211> LENGTH: 24
<212> TYPE: PRT
<213> ORGANISM: Artificial sequence
<220> FEATURE:
<223> OTHER INFORMATION: Fusion tag

<400> SEQUENCE: 16

Met Asn Asn Asn Gly Leu Thr Val Ala Gly Met Leu Gly Pro Ser Leu
1               5                   10                  15

Leu Thr Pro Arg Arg Ala Ser Ala
            20

<210> SEQ ID NO 17
<211> LENGTH: 19
<212> TYPE: PRT
<213> ORGANISM: Artificial sequence
<220> FEATURE:
<223> OTHER INFORMATION: Fusion tag

<400> SEQUENCE: 17

Met Asn Asn Asn Gly Met Leu Gly Pro Ser Leu Leu Thr Pro Arg Arg
1               5                   10                  15

Ala Ser Ala

<210> SEQ ID NO 18
<211> LENGTH: 14
<212> TYPE: PRT
<213> ORGANISM: Artificial sequence
<220> FEATURE:
<223> OTHER INFORMATION: Fusion tag

<400> SEQUENCE: 18

Met Asn Asn Asn Ser Leu Leu Thr Pro Arg Arg Ala Ser Ala
1               5                   10

<210> SEQ ID NO 19
<211> LENGTH: 9
<212> TYPE: PRT
<213> ORGANISM: Artificial sequence
<220> FEATURE:
<223> OTHER INFORMATION: Fusion tag

<400> SEQUENCE: 19

Met Asn Asn Asn Arg Arg Ala Ser Ala
1               5

<210> SEQ ID NO 20
<211> LENGTH: 4
<212> TYPE: PRT
<213> ORGANISM: Artificial sequence
<220> FEATURE:
<223> OTHER INFORMATION: Fusion tag

<400> SEQUENCE: 20
```

Met Asn Asn Asn
1

<210> SEQ ID NO 21
<211> LENGTH: 35
<212> TYPE: PRT
<213> ORGANISM: Artificial sequence
<220> FEATURE:
<223> OTHER INFORMATION: Fusion tag

<400> SEQUENCE: 21

Met Asn Asn Asn Asp Leu Phe Gln Ala Ser Arg Arg Arg Phe Leu Ala
1               5                   10                  15

Gln Leu Gly Gly Leu Thr Val Ala Gly Met Leu Gly Pro Ser Leu Leu
            20                  25                  30

Ala Ser Ala
        35

<210> SEQ ID NO 22
<211> LENGTH: 31
<212> TYPE: PRT
<213> ORGANISM: Artificial sequence
<220> FEATURE:
<223> OTHER INFORMATION: Fusion tag

<400> SEQUENCE: 22

Met Asn Asn Asn Asp Leu Phe Gln Ala Ser Arg Arg Arg Phe Leu Ala
1               5                   10                  15

Gln Leu Gly Gly Leu Thr Val Ala Gly Met Leu Gly Ala Ser Ala
            20                  25                  30

<210> SEQ ID NO 23
<211> LENGTH: 27
<212> TYPE: PRT
<213> ORGANISM: Artificial sequence
<220> FEATURE:
<223> OTHER INFORMATION: Fusion tag

<400> SEQUENCE: 23

Met Asn Asn Asn Asp Leu Phe Gln Ala Ser Arg Arg Arg Phe Leu Ala
1               5                   10                  15

Gln Leu Gly Gly Leu Thr Val Ala Ala Ser Ala
            20                  25

<210> SEQ ID NO 24
<211> LENGTH: 23
<212> TYPE: PRT
<213> ORGANISM: Artificial sequence
<220> FEATURE:
<223> OTHER INFORMATION: Fusion tag

<400> SEQUENCE: 24

Met Asn Asn Asn Asp Leu Phe Gln Ala Ser Arg Arg Arg Phe Leu Ala
1               5                   10                  15

Gln Leu Gly Gly Ala Ser Ala
            20

<210> SEQ ID NO 25
<211> LENGTH: 19
<212> TYPE: PRT
<213> ORGANISM: Artificial sequence
<220> FEATURE:
<223> OTHER INFORMATION: Fusion tag

```
<400> SEQUENCE: 25

Met Asn Asn Asn Asp Leu Phe Gln Ala Ser Arg Arg Arg Phe Leu Ala
1               5                   10                  15

Ala Ser Ala

<210> SEQ ID NO 26
<211> LENGTH: 26
<212> TYPE: PRT
<213> ORGANISM: Artificial sequence
<220> FEATURE:
<223> OTHER INFORMATION: Fusion tag

<400> SEQUENCE: 26

Met Asn Asn Asn Ser Arg Arg Arg Phe Leu Ala Gln Leu Gly Gly Leu
1               5                   10                  15

Thr Val Ala Gly Met Leu Gly Ala Ser Ala
            20                  25

<210> SEQ ID NO 27
<211> LENGTH: 39
<212> TYPE: PRT
<213> ORGANISM: Artificial sequence
<220> FEATURE:
<223> OTHER INFORMATION: Fusion tag

<400> SEQUENCE: 27

Met Asn Asn Asn Asp Leu Phe Gln Ala Ser Arg Arg Arg Phe Leu Pro
1               5                   10                  15

Gln Leu Gly Gly Leu Thr Val Ala Gly Met Leu Gly Pro Ser Leu Leu
            20                  25                  30

Thr Pro Arg Arg Ala Ser Ala
        35

<210> SEQ ID NO 28
<211> LENGTH: 39
<212> TYPE: PRT
<213> ORGANISM: Artificial sequence
<220> FEATURE:
<223> OTHER INFORMATION: Fusion tag

<400> SEQUENCE: 28

Met Asn Asn Asn Asp Leu Phe Gln Ala Ser Arg Arg Arg Tyr Leu Ala
1               5                   10                  15

Gln Leu Gly Gly Leu Thr Val Ala Gly Met Leu Gly Pro Ser Leu Leu
            20                  25                  30

Thr Pro Arg Arg Ala Ser Ala
        35

<210> SEQ ID NO 29
<211> LENGTH: 39
<212> TYPE: PRT
<213> ORGANISM: Artificial sequence
<220> FEATURE:
<223> OTHER INFORMATION: Fusion tag

<400> SEQUENCE: 29

Met Asn Asn Asn Asp Leu Phe Gln Ala Ser Cys Arg Arg Phe Leu Ala
1               5                   10                  15

Gln Leu Gly Gly Leu Thr Val Ala Gly Met Leu Gly Pro Ser Leu Leu
            20                  25                  30

Thr Pro Arg Arg Ala Ser Ala
        35
```

```
<210> SEQ ID NO 30
<211> LENGTH: 39
<212> TYPE: PRT
<213> ORGANISM: Artificial sequence
<220> FEATURE:
<223> OTHER INFORMATION: Fusion tag

<400> SEQUENCE: 30

Met Asn Asn Asn Asp Leu Phe Gln Ala Ser His Arg Arg Phe Leu Ala
1               5                   10                  15

Gln Leu Gly Gly Leu Thr Val Ala Gly Met Leu Gly Pro Ser Leu Leu
            20                  25                  30

Thr Pro Arg Arg Ala Ser Ala
        35

<210> SEQ ID NO 31
<211> LENGTH: 39
<212> TYPE: PRT
<213> ORGANISM: Artificial sequence
<220> FEATURE:
<223> OTHER INFORMATION: Fusion tag

<400> SEQUENCE: 31

Met Asn Asn Asn Asp Leu Phe Gln Ala Ser Ser Arg Arg Phe Leu Ala
1               5                   10                  15

Gln Leu Gly Gly Leu Thr Val Ala Gly Met Leu Gly Pro Ser Leu Leu
            20                  25                  30

Thr Pro Arg Arg Ala Ser Ala
        35

<210> SEQ ID NO 32
<211> LENGTH: 39
<212> TYPE: PRT
<213> ORGANISM: Artificial sequence
<220> FEATURE:
<223> OTHER INFORMATION: Fusion tag

<400> SEQUENCE: 32

Met Asn Asn Asn Asp Leu Phe Gln Ala Ser Arg Leu Arg Phe Leu Ala
1               5                   10                  15

Gln Leu Gly Gly Leu Thr Val Ala Gly Met Leu Gly Pro Ser Leu Leu
            20                  25                  30

Thr Pro Arg Arg Ala Ser Ala
        35

<210> SEQ ID NO 33
<211> LENGTH: 39
<212> TYPE: PRT
<213> ORGANISM: Artificial sequence
<220> FEATURE:
<223> OTHER INFORMATION: Fusion tag

<400> SEQUENCE: 33

Met Asn Asn Asn Asp Leu Phe Gln Ala Ser Arg Gln Arg Phe Leu Ala
1               5                   10                  15

Gln Leu Gly Gly Leu Thr Val Ala Gly Met Leu Gly Pro Ser Leu Leu
            20                  25                  30

Thr Pro Arg Arg Ala Ser Ala
        35

<210> SEQ ID NO 34
```

```
<211> LENGTH: 39
<212> TYPE: PRT
<213> ORGANISM: Artificial sequence
<220> FEATURE:
<223> OTHER INFORMATION: Fusion tag

<400> SEQUENCE: 34

Met Asn Asn Asn Asp Leu Phe Gln Ala Ser Arg Arg Arg Phe Gln Ala
1               5                   10                  15

Gln Leu Gly Gly Leu Thr Val Ala Gly Met Leu Gly Pro Ser Leu Leu
            20                  25                  30

Thr Pro Arg Arg Ala Ser Ala
        35

<210> SEQ ID NO 35
<211> LENGTH: 39
<212> TYPE: PRT
<213> ORGANISM: Artificial sequence
<220> FEATURE:
<223> OTHER INFORMATION: Fusion tag

<400> SEQUENCE: 35

Met Asn Asn Asn Asp Leu Phe Gln Ala Ser Arg Arg Arg Phe Pro Ala
1               5                   10                  15

Gln Leu Gly Gly Leu Thr Val Ala Gly Met Leu Gly Pro Ser Leu Leu
            20                  25                  30

Thr Pro Arg Arg Ala Ser Ala
        35

<210> SEQ ID NO 36
<211> LENGTH: 39
<212> TYPE: PRT
<213> ORGANISM: Artificial sequence
<220> FEATURE:
<223> OTHER INFORMATION: Fusion tag

<400> SEQUENCE: 36

Met Asn Asn Asn Asp Leu Phe Gln Ala Ser Arg Arg Arg Phe Leu Ala
1               5                   10                  15

Gln His Gly Gly Leu Thr Val Ala Gly Met Leu Gly Pro Ser Leu Leu
            20                  25                  30

Thr Pro Arg Arg Ala Ser Ala
        35

<210> SEQ ID NO 37
<211> LENGTH: 39
<212> TYPE: PRT
<213> ORGANISM: Artificial sequence
<220> FEATURE:
<223> OTHER INFORMATION: Fusion tag

<400> SEQUENCE: 37

Met Asn Asn Asn Asp Leu Phe Gln Ala Ser Arg Arg Arg Phe Leu Ala
1               5                   10                  15

Gln Pro Gly Gly Leu Thr Val Ala Gly Met Leu Gly Pro Ser Leu Leu
            20                  25                  30

Thr Pro Arg Arg Ala Ser Ala
        35

<210> SEQ ID NO 38
<211> LENGTH: 39
<212> TYPE: PRT
<213> ORGANISM: Artificial sequence
```

```
<220> FEATURE:
<223> OTHER INFORMATION: Fusion tag

<400> SEQUENCE: 38

Met Asn Asn Asn Asp Leu Phe Gln Ala Ser Arg Arg Arg Phe Leu Ala
1               5                   10                  15

Gln Leu Asp Gly Leu Thr Val Ala Gly Met Leu Gly Pro Ser Leu Leu
            20                  25                  30

Thr Pro Arg Arg Ala Ser Ala
            35

<210> SEQ ID NO 39
<211> LENGTH: 39
<212> TYPE: PRT
<213> ORGANISM: Artificial sequence
<220> FEATURE:
<223> OTHER INFORMATION: Fusion tag

<400> SEQUENCE: 39

Met Asn Asn Asn Asp Leu Phe Gln Ala Ser Arg Arg Arg Phe Met Ala
1               5                   10                  15

Gln Leu Gly Gly Leu Thr Val Ala Gly Met Leu Gly Pro Ser Leu Leu
            20                  25                  30

Thr Pro Arg Arg Ala Ser Ala
            35

<210> SEQ ID NO 40
<211> LENGTH: 39
<212> TYPE: PRT
<213> ORGANISM: Artificial sequence
<220> FEATURE:
<223> OTHER INFORMATION: Fusion tag

<400> SEQUENCE: 40

Met Asn Asn Asn Asp Leu Phe Gln Ala Ser Arg Arg Arg Phe Leu Ala
1               5                   10                  15

Glu Leu Gly Gly Leu Thr Val Ala Gly Met Leu Gly Pro Ser Leu Leu
            20                  25                  30

Thr Pro Arg Arg Ala Ser Ala
            35

<210> SEQ ID NO 41
<211> LENGTH: 39
<212> TYPE: PRT
<213> ORGANISM: Artificial sequence
<220> FEATURE:
<223> OTHER INFORMATION: Fusion tag

<400> SEQUENCE: 41

Met Asn Asn Asn Asp Leu Phe Gln Ala Ser Arg Arg Arg Phe Leu Ala
1               5                   10                  15

Gln Ile Gly Gly Leu Thr Val Ala Gly Met Leu Gly Pro Ser Leu Leu
            20                  25                  30

Thr Pro Arg Arg Ala Ser Ala
            35

<210> SEQ ID NO 42
<211> LENGTH: 39
<212> TYPE: PRT
<213> ORGANISM: Artificial sequence
<220> FEATURE:
<223> OTHER INFORMATION: Fusion tag
```

```
<400> SEQUENCE: 42

Met Asn Asn Asn Asp Leu Phe Gln Ala Ser Arg Arg Arg Phe Leu Ala
1               5                   10                  15

Gln Val Gly Gly Leu Thr Val Ala Gly Met Leu Gly Pro Ser Leu Leu
            20                  25                  30

Thr Pro Arg Arg Ala Ser Ala
            35

<210> SEQ ID NO 43
<211> LENGTH: 39
<212> TYPE: PRT
<213> ORGANISM: Artificial sequence
<220> FEATURE:
<223> OTHER INFORMATION: Fusion tag

<400> SEQUENCE: 43

Met Asn Asn Asn Asp Leu Phe Gln Ala Ser Arg Arg Arg Phe Leu Ala
1               5                   10                  15

Gln Leu Val Gly Leu Thr Val Ala Gly Met Leu Gly Pro Ser Leu Leu
            20                  25                  30

Thr Pro Arg Arg Ala Ser Ala
            35

<210> SEQ ID NO 44
<211> LENGTH: 39
<212> TYPE: PRT
<213> ORGANISM: Escherichia coli

<400> SEQUENCE: 44

Met Asn Asn Asn Asp Leu Phe Gln Ala Ser Arg Arg Arg Phe Leu Ala
1               5                   10                  15

Gln Leu Gly Gly Leu Thr Val Ala Gly Met Leu Gly Pro Ser Leu Leu
            20                  25                  30

Thr Pro Arg Arg Ala Thr Ala
            35

<210> SEQ ID NO 45
<211> LENGTH: 5
<212> TYPE: PRT
<213> ORGANISM: Artificial sequence
<220> FEATURE:
<223> OTHER INFORMATION: Partial fusion tag

<400> SEQUENCE: 45

Asp Leu Phe Gln Ala
1               5

<210> SEQ ID NO 46
<211> LENGTH: 23
<212> TYPE: PRT
<213> ORGANISM: Artificial sequence
<220> FEATURE:
<223> OTHER INFORMATION: Partial fusion tag
<220> FEATURE:
<221> NAME/KEY: VARIANT
<222> LOCATION: (1)..(3)
<223> OTHER INFORMATION: N, A, K or T
<220> FEATURE:
<221> NAME/KEY: VARIANT
<222> LOCATION: (9)..(9)
<223> OTHER INFORMATION: F or Y
<220> FEATURE:
<221> NAME/KEY: VARIANT
<222> LOCATION: (10)..(10)
<223> OTHER INFORMATION: L or M
```

```
<220> FEATURE:
<221> NAME/KEY: VARIANT
<222> LOCATION: (12)..(12)
<223> OTHER INFORMATION: Q or E
<220> FEATURE:
<221> NAME/KEY: VARIANT
<222> LOCATION: (13)..(13)
<223> OTHER INFORMATION: L, V or I
<220> FEATURE:
<221> NAME/KEY: VARIANT
<222> LOCATION: (14)..(14)
<223> OTHER INFORMATION: G or V

<400> SEQUENCE: 46

Xaa Xaa Xaa Asp Leu Phe Gln Ala Xaa Xaa Ala Xaa Xaa Xaa Gly Leu
1               5                   10                  15

Thr Val Ala Gly Met Leu Gly
            20

<210> SEQ ID NO 47
<211> LENGTH: 9
<212> TYPE: PRT
<213> ORGANISM: Artificial sequence
<220> FEATURE:
<223> OTHER INFORMATION: Partial fusion tag

<400> SEQUENCE: 47

Asp Leu Phe Gln Ala Ser Arg Arg Arg
1               5

<210> SEQ ID NO 48
<211> LENGTH: 27
<212> TYPE: PRT
<213> ORGANISM: Artificial sequence
<220> FEATURE:
<223> OTHER INFORMATION: Partial fusion tag
<220> FEATURE:
<221> NAME/KEY: VARIANT
<222> LOCATION: (1)..(3)
<223> OTHER INFORMATION: N, A, K or T
<220> FEATURE:
<221> NAME/KEY: VARIANT
<222> LOCATION: (13)..(13)
<223> OTHER INFORMATION: F or Y
<220> FEATURE:
<221> NAME/KEY: VARIANT
<222> LOCATION: (14)..(14)
<223> OTHER INFORMATION: L or M
<220> FEATURE:
<221> NAME/KEY: VARIANT
<222> LOCATION: (16)..(16)
<223> OTHER INFORMATION: Q or E
<220> FEATURE:
<221> NAME/KEY: VARIANT
<222> LOCATION: (17)..(17)
<223> OTHER INFORMATION: L, V or I
<220> FEATURE:
<221> NAME/KEY: VARIANT
<222> LOCATION: (18)..(18)
<223> OTHER INFORMATION: G or V

<400> SEQUENCE: 48

Xaa Xaa Xaa Asp Leu Phe Gln Ala Ser Arg Arg Arg Xaa Xaa Ala Xaa
1               5                   10                  15

Xaa Xaa Gly Leu Thr Val Ala Gly Met Leu Gly
            20                  25

<210> SEQ ID NO 49
<211> LENGTH: 26
<212> TYPE: PRT
<213> ORGANISM: Artificial sequence
```

-continued

```
<220> FEATURE:
<223> OTHER INFORMATION: Partial fusion tag
<220> FEATURE:
<221> NAME/KEY: VARIANT
<222> LOCATION: (1)..(1)
<223> OTHER INFORMATION: F or Y
<220> FEATURE:
<221> NAME/KEY: VARIANT
<222> LOCATION: (2)..(2)
<223> OTHER INFORMATION: L or M
<220> FEATURE:
<221> NAME/KEY: VARIANT
<222> LOCATION: (4)..(4)
<223> OTHER INFORMATION: Q or E
<220> FEATURE:
<221> NAME/KEY: VARIANT
<222> LOCATION: (5)..(5)
<223> OTHER INFORMATION: L, V or I
<220> FEATURE:
<221> NAME/KEY: VARIANT
<222> LOCATION: (6)..(6)
<223> OTHER INFORMATION: G or V
<220> FEATURE:
<221> NAME/KEY: VARIANT
<222> LOCATION: (25)..(25)
<223> OTHER INFORMATION: S or T

<400> SEQUENCE: 49

Xaa Xaa Ala Xaa Xaa Xaa Gly Leu Thr Val Ala Gly Met Leu Gly Pro
1               5                   10                  15

Ser Leu Leu Thr Pro Arg Arg Ala Xaa Ala
            20                  25

<210> SEQ ID NO 50
<211> LENGTH: 34
<212> TYPE: PRT
<213> ORGANISM: Artificial sequence
<220> FEATURE:
<223> OTHER INFORMATION: Partial fusion tag
<220> FEATURE:
<221> NAME/KEY: VARIANT
<222> LOCATION: (1)..(3)
<223> OTHER INFORMATION: N, A, K or T
<220> FEATURE:
<221> NAME/KEY: VARIANT
<222> LOCATION: (9)..(9)
<223> OTHER INFORMATION: F or Y
<220> FEATURE:
<221> NAME/KEY: VARIANT
<222> LOCATION: (10)..(10)
<223> OTHER INFORMATION: L or M
<220> FEATURE:
<221> NAME/KEY: VARIANT
<222> LOCATION: (12)..(12)
<223> OTHER INFORMATION: Q or E
<220> FEATURE:
<221> NAME/KEY: VARIANT
<222> LOCATION: (13)..(13)
<223> OTHER INFORMATION: L, V or I
<220> FEATURE:
<221> NAME/KEY: VARIANT
<222> LOCATION: (14)..(14)
<223> OTHER INFORMATION: G or V
<220> FEATURE:
<221> NAME/KEY: VARIANT
<222> LOCATION: (33)..(33)
<223> OTHER INFORMATION: S or T

<400> SEQUENCE: 50

Xaa Xaa Xaa Asp Leu Phe Gln Ala Xaa Xaa Ala Xaa Xaa Xaa Gly Leu
1               5                   10                  15

Thr Val Ala Gly Met Leu Gly Pro Ser Leu Leu Thr Pro Arg Arg Ala
            20                  25                  30
```

Xaa Ala

<210> SEQ ID NO 51
<211> LENGTH: 7
<212> TYPE: PRT
<213> ORGANISM: Artificial sequence
<220> FEATURE:
<223> OTHER INFORMATION: Consensus Tat signal
<220> FEATURE:
<221> NAME/KEY: VARIANT
<222> LOCATION: (1)..(1)
<223> OTHER INFORMATION: S or T
<220> FEATURE:
<221> NAME/KEY: VARIANT
<222> LOCATION: (4)..(4)
<223> OTHER INFORMATION: Any polar amino acid

<400> SEQUENCE: 51

Xaa Arg Arg Xaa Phe Leu Lys
1               5

<210> SEQ ID NO 52
<211> LENGTH: 9
<212> TYPE: PRT
<213> ORGANISM: Artificial sequence
<220> FEATURE:
<223> OTHER INFORMATION: HA detection tag

<400> SEQUENCE: 52

Tyr Pro Tyr Asp Val Pro Asp Tyr Ala
1               5

<210> SEQ ID NO 53
<211> LENGTH: 30
<212> TYPE: PRT
<213> ORGANISM: Artificial sequence
<220> FEATURE:
<223> OTHER INFORMATION: Fusion tag

<400> SEQUENCE: 53

Met Asn Asn Asn Asp Leu Phe Gln Ala Ser Arg Arg Arg Phe Leu Ala
1               5                   10                  15

Gln Leu Gly Gly Leu Thr Val Ala Gly Met Leu Gly Ala Ser
            20                  25                  30

<210> SEQ ID NO 54
<211> LENGTH: 58
<212> TYPE: PRT
<213> ORGANISM: Artificial sequence
<220> FEATURE:
<223> OTHER INFORMATION: Fusion tag

<400> SEQUENCE: 54

Met Asn Asn Asn Asp Leu Phe Gln Ala Ser Arg Arg Arg Phe Leu Ala
1               5                   10                  15

Gln Leu Gly Gly Leu Thr Val Ala Gly Met Leu Gly Met Asn Asn Asn
            20                  25                  30

Asp Leu Phe Gln Ala Ser Arg Arg Arg Phe Leu Ala Gln Leu Gly Gly
        35                  40                  45

Leu Thr Val Ala Gly Met Leu Gly Ala Ser
    50                  55

<210> SEQ ID NO 55
<211> LENGTH: 86
<212> TYPE: PRT
<213> ORGANISM: Artificial sequence
<220> FEATURE:
<223> OTHER INFORMATION: Fusion tag

<400> SEQUENCE: 55

Met Asn Asn Asn Asp Leu Phe Gln Ala Ser Arg Arg Phe Leu Ala
1               5                   10                  15

Gln Leu Gly Gly Leu Thr Val Ala Gly Met Leu Gly Met Asn Asn
            20                  25                  30

Asp Leu Phe Gln Ala Ser Arg Arg Phe Leu Ala Gln Leu Gly Gly
        35                  40                  45

Leu Thr Val Ala Gly Met Leu Gly Met Asn Asn Asp Leu Phe Gln
    50                  55                  60

Ala Ser Arg Arg Arg Phe Leu Ala Gln Leu Gly Gly Leu Thr Val Ala
65                  70                  75                  80

Gly Met Leu Gly Ala Ser
                85

<210> SEQ ID NO 56
<211> LENGTH: 84
<212> TYPE: PRT
<213> ORGANISM: Artificial sequence
<220> FEATURE:
<223> OTHER INFORMATION: Fusion tag

<400> SEQUENCE: 56

Met Asn Asn Asn Asp Leu Phe Gln Ala Ser Arg Arg Phe Leu Ala
1               5                   10                  15

Gln Leu Gly Gly Leu Thr Val Ala Gly Met Leu Gly Met Asn Asn
            20                  25                  30

Asp Leu Phe Gln Ala Ser Arg Arg Phe Leu Ala Gln Leu Gly Gly
        35                  40                  45

Leu Thr Val Ala Gly Met Leu Gly Met Asn Asn Asp Leu Phe Gln
    50                  55                  60

Ala Ser Arg Arg Arg Phe Leu Ala Gln Leu Gly Gly Leu Thr Val Ala
65                  70                  75                  80

Gly Met Leu Gly

<210> SEQ ID NO 57
<211> LENGTH: 87
<212> TYPE: PRT
<213> ORGANISM: Artificial sequence
<220> FEATURE:
<223> OTHER INFORMATION: Fusion tag

<400> SEQUENCE: 57

Met Asn Asn Asn Asp Leu Phe Gln Ala Ser Arg Arg Phe Leu Ala
1               5                   10                  15

Gln Leu Gly Gly Leu Thr Val Ala Gly Met Leu Gly Met Asn Asn
            20                  25                  30

Asp Leu Phe Gln Ala Ser Arg Arg Phe Leu Ala Gln Leu Gly Gly
        35                  40                  45

Leu Thr Val Ala Gly Met Leu Gly Met Asn Asn Asp Leu Phe Gln
    50                  55                  60

Ala Ser Arg Arg Arg Phe Leu Ala Gln Leu Gly Gly Leu Thr Val Ala
65                  70                  75                  80

Gly Met Leu Gly Ala Ser Ala
                85

```
<210> SEQ ID NO 58
<211> LENGTH: 23
<212> TYPE: PRT
<213> ORGANISM: Artificial sequence
<220> FEATURE:
<223> OTHER INFORMATION: Fusion tag
<220> FEATURE:
<221> NAME/KEY: VARIANT
<222> LOCATION: (1)..(1)
<223> OTHER INFORMATION: F or Y
<220> FEATURE:
<221> NAME/KEY: VARIANT
<222> LOCATION: (2)..(2)
<223> OTHER INFORMATION: L or M
<220> FEATURE:
<221> NAME/KEY: VARIANT
<222> LOCATION: (4)..(4)
<223> OTHER INFORMATION: Q or E
<220> FEATURE:
<221> NAME/KEY: VARIANT
<222> LOCATION: (5)..(5)
<223> OTHER INFORMATION: L, V or I
<220> FEATURE:
<221> NAME/KEY: VARIANT
<222> LOCATION: (6)..(6)
<223> OTHER INFORMATION: G or V

<400> SEQUENCE: 58

Xaa Xaa Ala Xaa Xaa Xaa Gly Leu Thr Val Ala Gly Met Leu Gly Pro
1               5                   10                  15

Ser Leu Leu Thr Pro Arg Arg
            20

<210> SEQ ID NO 59
<211> LENGTH: 31
<212> TYPE: PRT
<213> ORGANISM: Artificial sequence
<220> FEATURE:
<223> OTHER INFORMATION: Fusion tag
<220> FEATURE:
<221> NAME/KEY: VARIANT
<222> LOCATION: (1)..(3)
<223> OTHER INFORMATION: N, A, K or T
<220> FEATURE:
<221> NAME/KEY: VARIANT
<222> LOCATION: (9)..(9)
<223> OTHER INFORMATION: F or Y
<220> FEATURE:
<221> NAME/KEY: VARIANT
<222> LOCATION: (10)..(10)
<223> OTHER INFORMATION: L or M
<220> FEATURE:
<221> NAME/KEY: VARIANT
<222> LOCATION: (12)..(12)
<223> OTHER INFORMATION: Q or E
<220> FEATURE:
<221> NAME/KEY: VARIANT
<222> LOCATION: (13)..(13)
<223> OTHER INFORMATION: L, V or I
<220> FEATURE:
<221> NAME/KEY: VARIANT
<222> LOCATION: (14)..(14)
<223> OTHER INFORMATION: G or V

<400> SEQUENCE: 59

Xaa Xaa Xaa Asp Leu Phe Gln Ala Xaa Xaa Ala Xaa Xaa Xaa Gly Leu
1               5                   10                  15

Thr Val Ala Gly Met Leu Gly Pro Ser Leu Leu Thr Pro Arg Arg
            20                  25                  30
```

FUSION POLYPEPTIDES COMPRISING ONE OR MORE INCLUSION BODY TAGS, METHODS AND USES

CROSS-REFERENCE TO RELATED APPLICATIONS

This application is a § 371 national phase of International Application No. PCT/EP2018/052093, filed on Jan. 29, 2018, which claims the benefit of European Patent Application No. 17153605.5, filed on Jan. 27, 2017, which applications are incorporated by reference herein.

FIELD OF THE INVENTION

The present disclosure relates in general to the field of polypeptide and protein expression. More specifically, the disclosure relates to fusion polypeptides comprising tags, so-called inclusion body tags, that are useful for production of polypeptides and proteins in inclusion bodies. It also relates to methods and uses that exploit such tags for producing polypeptides and proteins in inclusion bodies.

BACKGROUND OF THE INVENTION

Efficient production of proteins, or polypeptides, has become an essential part of the biomedical and industrial biochemical industries. Biopharmaceutical products have become increasingly important in the pharmaceutical industry, and polypeptides and proteins are needed in various industries, such as the food and beverage, cosmetic, washing detergent, pulp and paper, textile and wastewater industries, to name a few.

Such pharmaceutical and industrially used proteins or polypeptides are commonly produced as recombinant proteins in host cells that are recombinantly engineered to over-express the selected protein or polypeptide (Terpe, K., Appl Microbiol Biotechnol. (2006) 72:211-223). The host cells can for instance be selected from bacterial cells, yeast cells and mammalian cells.

Yeast and mammalian cells are often more expensive and less efficient to use than bacterial cells, but may be necessary for expression and production of unstable or complex proteins that require a eukaryotic protein expression system to achieve its functionality. Bacterial host cells are often preferred for industrial scale production of proteins, since bacterial cells are easier to handle and give a higher protein yield in a shorter period of time, thus being more cost efficient. *Escherichia coli* (*E. coli*) is one of the most commonly used and well-studied hosts for commercial and research based production of heterologous proteins.

Although quite efficient, recombinant production of proteins or polypeptides suffers from some disadvantages. Polypeptides produced in a cellular environment are susceptible to degradation through the action of cellular proteases. Also, heterologous disulphide-containing proteins expressed in the cytoplasm of bacteria, such as *E. coli*, may be unstable or fold incorrectly since the disulphide bridges, which are often important for proper folding and stability, cannot form in this compartment. Some polypeptides are so unstable and prone to degradation that they are impossible or very difficult to recover from the host cell. Some polypeptides of interest are toxic to the host cell and inhibit host cell growth and/or induce host cell death, leading to reduced or even completely ceased protein production. Also, purification and isolation of the polypeptide of interest from the other proteins in the protein rich cytoplasm, and from other cell components, can be difficult and very labor intense (Weikert, M. J. et al., Curr Opin Biotechnol. (1996) 7:494-499; Baneyx, F. and Mujacic, M., Nat Biotechnol. (2004) 22:1399-1408).

In order to circumvent these obstacles, several different techniques have been developed. The polypeptide of interest may for instance be produced such that it is exported to the periplasm, which enables disulphide bond formation and provides a more favorable environment for folding and stability of heterologous proteins (Baneyx, F. and Mujacic, M., Nat Biotechnol. (2004) 22:1399-1408). Another strategy is to produce the polypeptide of interest such that it is exported to the extracellular space, where it is more easily isolated (Choi, J. H. and Lee, S. Y., Appl Microbiol Biotechnol. (2004) 64(5):625-35). Although such strategies overcome some of the above-mentioned problems, there are still some disadvantages associated with them. Export of the polypeptide of interest to the periplasm or extracellular space requires translocation of the protein across one or two membranes. Such translocation is often difficult and inefficient and therefore leads to low protein yields (Sahdev, S. et al., Mol Cell Biochem. (2008) 307:249-264). Furthermore, the polypeptide of interest may still be toxic to the host cell, and proteins located in the periplasm may be difficult to isolate and purify (Jana, S. and Deb, J. K., Appl Microbiol Biotechnol. (2005) 67:289-298; Swartz, J. R., Curr Opin Biotechnol. (2001) 12:195-201).

One strategy to avoid or overcome these disadvantages is to produce the polypeptide of interest in inclusion bodies (Sahdev, S. et al., Mol Cell Biochem. (2008) 307:249-264; Swartz, J. R., Curr Opin Biotechnol. (2001) 12:195-201; Martinez-Alonso, M. et al., Microb Cell Fact. (2009) 8:4). Inclusion bodies are water-insoluble aggregates of polypeptides in the cytoplasm or periplasm of bacterial cells or in the nucleus or cytoplasm of eukaryotic cells. The polypeptides contained in inclusion bodies are generally inactive, and thus, by producing the polypeptides in inclusion bodies, the host cell is protected from any toxic effects that the polypeptide of interest would otherwise have. The insoluble form of the polypeptides contained in inclusion bodies also renders the polypeptides resistant to degradation. Moreover, inclusion bodies contain large amounts of relatively pure material and are rather easily isolated from the rest of the cellular constituents. Production of a polypeptide of interest in inclusion bodies may thus facilitate simple recovery of the polypeptide, protect the polypeptide from degradation and protect the host cell in case the polypeptide of interest is toxic.

One way to produce a polypeptide of interest in inclusion bodies is to fuse the polypeptide to a tag that induces formation of inclusion bodies, i.e. an "inclusion body tag". The polypeptide of interest is recombinantly fused to the inclusion body tag, and the resulting fusion polypeptide is produced in inclusion bodies when expressed. A number of different tags are known that induce formation of inclusion bodies when fused to a polypeptide of interest. Typically, these tags comprise a peptide or protein that is rather large, which increases the likelihood that it will be insoluble and prone to form inclusion bodies. Examples include chloramphenicol acetyltransferase, 1-galactosidase and ketosteroid isomerase. The fusion protein is typically designed to include a cleavage site between the polypeptide of interest and the inclusion body tag, such that the inclusion body tag can be removed from the polypeptide of interest once the fusion protein has been recovered from the inclusion bodies.

US2009/0029420 A1 discloses an inclusion body tag derived from the ketosteroid isomerase (KSI). The tag has been shown to be efficient in inducing inclusion body formation when fused to a small peptide of interest and has been engineered to become more resistant to acid hydrolysis.

WO98/30684 discloses an inclusion partner protein based on a bacterial thioredoxin, such as a carboxy-terminally truncated form of *E. coli* thioredoxin.

There is still a need for alternative tags or fusion partners that enable efficient production of polypeptides of interest in inclusion bodies.

SUMMARY OF THE INVENTION

It is an object of the present invention to overcome this problem, and to provide such a fusion tag for production of a polypeptide of interest in inclusion bodies.

According to a first aspect, this and other objects are achieved by a fusion polypeptide comprising an inclusion body tag fused to at least one polypeptide of interest, wherein said inclusion body tag comprises an inclusion body forming (IBF) amino acid sequence selected from:

i)

$$X_{14}X_{15}AX_{17}X_{18}\ X_{19}GLTVA\ GMLG \quad (SEQ\ ID\ NO:\ 1)$$

wherein, independently from each other,
$X_{14}$ is selected from F and Y;
$X_{15}$ is selected from L and M;
$X_{17}$ is selected from Q and E;
$X_{18}$ is selected from L, V and I; and
$X_{19}$ is selected from G and V;
and
ii) an amino acid sequence which has at least 71% identity to the sequence defined in i).

In one embodiment of this fusion polypeptide, the sequence IBF is selected from:

iii)

$$SX_{11}X_{12}RX_{14}X_{15}AX_{17}X_{18}\ X_{19}GLTVA\ GMLG \quad (SEQ\ ID\ NO:\ 2)$$

wherein, independently from each other,
$X_{11}$ is selected from R, C, K, A, S and H;
$X_{12}$ is selected from R, Q, K, A and L; and
$X_{14}$, $X_{15}$, $X_{17}$, $X_{18}$ and $X_{19}$ are as defined above;
and
iv) an amino acid sequence which has at least 77% identity to the sequence defined in iii).

As used herein, "$X_n$" and "$X_m$" are used to indicate amino acids in positions n and m in the sequences i) and iii) as defined above, wherein n and m are integers which indicate the position of an amino acid within said sequence as counted from the N-terminal end of the ssTorA sequence from which they are derived (SEQ ID NO:3). For example, $X_{14}$ and $X_{18}$ indicate the amino acids in the positions corresponding to positions 14 and 18, respectively, counted from the N-terminal end of SEQ ID NO:3.

In embodiments of the first aspect, polypeptides are provided wherein $X_n$ in sequence i) or iii) is independently selected from a group of possible residues according to Table 1 below. The skilled person will appreciate that $X_n$ may be selected from any one of the listed groups of possible residues and that this selection is independent from the selection of amino acids in $X_m$, wherein n m. Thus, any of the listed possible residues in position $X_n$ in Table 1 may be independently combined with any of the listed possible residues in any other variable position in Table 1.

The skilled person will appreciate that Table 1 is to be read as follows: In one embodiment according to the first aspect, there is provided a polypeptide wherein amino acid residue "$X_n$" in sequence i) or iii) is selected from "Possible residues". Thus, Table 1 discloses several specific and individualized embodiments of the first aspect of the present disclosure. For example, in one embodiment according to the first aspect, there is provided a polypeptide wherein $X_{11}$ in sequence iii) is selected from R, C, K, A, S and H, and in another embodiment according to the first aspect, there is provided a polypeptide wherein $X_{11}$ in sequence iii) is selected from R, C and H. For avoidance of doubt, the listed embodiments may be freely combined in yet other embodiments. For example, one such combined embodiment is a polypeptide in which $X_{11}$ is selected from R, C and H, while $X_{15}$ is L and $X_{19}$ is selected from G and V.

TABLE 1

| $X_n$ | Possible residues |
|---|---|
| $X_{11}$ | R, C, K, A, S and H |
| $X_{11}$ | R, C, K, A and H |
| $X_{11}$ | R, C, S and H |
| $X_{11}$ | R, C and H |
| $X_{11}$ | R and C |
| $X_{11}$ | R, K and A |
| $X_{11}$ | K and A |
| $X_{11}$ | C, S and H |
| $X_{11}$ | C and H |
| $X_{11}$ | R |
| $X_{11}$ | C |
| $X_{11}$ | K |
| $X_{11}$ | A |
| $X_{11}$ | S |
| $X_{11}$ | H |
| $X_{12}$ | R, Q, K, A and L |
| $X_{12}$ | R, Q and L |
| $X_{12}$ | R, K and A |
| $X_{12}$ | Q and L |
| $X_{12}$ | K and A |
| $X_{12}$ | R |
| $X_{12}$ | Q |
| $X_{12}$ | K |
| $X_{12}$ | A |
| $X_{12}$ | L |
| $X_{14}$ | F and Y |
| $X_{14}$ | F |
| $X_{14}$ | Y |
| $X_{15}$ | L and M |
| $X_{15}$ | L |
| $X_{15}$ | M |
| $X_{17}$ | Q and E |
| $X_{17}$ | Q |
| $X_{17}$ | E |
| $X_{18}$ | L, V and I |
| $X_{18}$ | V and I |
| $X_{18}$ | L |
| $X_{18}$ | V |
| $X_{18}$ | I |
| $X_{19}$ | G and V |
| $X_{19}$ | G |
| $X_{19}$ | V |

The inclusion body forming sequence IBF defined above was identified by the present inventors as the core motif responsible for inclusion body formation of fusion polypeptides according to the first aspect of the disclosure. From the disclosure herein, it is clear that the starting key insight underlying the invention was that the signal sequence from the *E. coli* protein trimethylamine-N-oxide reductase (TorA, TOR or TMAO reductase) acts as an inclusion body forming tag when fused to a heterologous protein. Based on this initial finding, and following extensive work on mutation and deletion analysis, the inventors arrived at the above definition of the core IBF sequence. The work leading to this identification is described in detail in the Examples section.

As the skilled person will realize, the function of any polypeptide, such as the inclusion body forming capacity inherent in the inclusion body tag of the fusion polypeptide of the first aspect, is dependent on the structure of the polypeptide. It is therefore possible to make minor changes to the sequence of amino acids in a polypeptide without affecting its function. Thus, the disclosure encompasses modified variants of the inclusion body forming sequence, which have retained functional characteristics.

In this way, encompassed by the present disclosure is a polypeptide having an inclusion body tag which comprises an inclusion body forming sequence with 71% or greater identity to a sequence according to i), as defined by ii) in the first definition above. Likewise encompassed is a polypeptide having an inclusion body tag which comprises an inclusion body forming sequence with 77% or greater identity to a sequence according to iii), as defined by iv) in the second definition above. For example, it is possible that an amino acid residue belonging to a certain functional grouping of amino acid residues (e.g. hydrophobic, hydrophilic, polar etc) could be exchanged for another amino acid residue from the same functional group. Such minor changes are also within the scope of the present disclosure. In some embodiments, sequence ii) has at least 78%, such as at least 85%, such as at least 92% identity to a sequence defined by i). In some embodiments, sequence iv) has at least 83%, such as at least 88%, such as at least 94% identity to a sequence defined by iii).

In some embodiments, such changes may be made in any position of the sequence of the IBF sequence as disclosed herein. In other embodiments, such changes may be made only in the positions that do not allow for other variation, i.e. positions other than the "$X_n$" positions. In other embodiments, such changes may be only in the variable "$X_n$" positions.

In some embodiments, the IBF is useful as IB forming fusion tag in its own right. In other embodiments, it forms part of a longer sequence, which may comprise other elements derived from ssTorA or other sequence elements without affecting the IB forming function.

In one such embodiment, there is provided a fusion polypeptide, wherein said inclusion body tag comprises the amino acid sequence:

$X_2X_3X_4$-Z-IBF wherein, independently from each other,
$X_2$, $X_3$ and $X_4$ are each individually selected from N, A, K and T;
Z is a spacer sequence comprising 0-10 amino acids; and
IBF is an inclusion body forming sequence as defined above.

In one embodiment of this longer inclusion body tag, the sequence [Z] consists of 0 amino acids, so that the tag comprises $X_2X_3X_4$-[IBF].

In another embodiment, [Z] consists of the five amino acid residues DLFQA (SEQ ID NO:45), so that the tag comprises $X_2X_3X_4$-DLFQA-[IBF](SEQ ID NO:46).

In yet another embodiment, [Z] consists of the nine amino acid residues DLFQASRRR (SEQ ID NO:47), so that the tag comprises $X_2X_3X_4$-DLFQASRRR-[IBF] (SEQ ID NO:48).

In one embodiment, the amino acid sequence comprised in the inclusion body tag further includes an M residue in the position corresponding to position 1 of the ssTorA sequence (SEQ ID NO:3).

In analogy to what is explained above in connection with Table 1, the disclosure encompasses all possible individual combinations of sequences with the alternative amino acid residues given herein. Thus, Table 2 below is to be read in the same way as explained for Table 1.

TABLE 2

| $X_n$ | Possible residues |
|---|---|
| $X_2$ | N, A, K and T |
| $X_2$ | N and A |
| $X_2$ | K and T |
| $X_2$ | N |
| $X_2$ | A |
| $X_2$ | K |
| $X_2$ | T |
| $X_3$ | N, A, K and T |
| $X_3$ | N and A |
| $X_3$ | K and T |
| $X_3$ | N |
| $X_3$ | A |
| $X_3$ | K |
| $X_3$ | T |
| $X_4$ | N, A, K and T |
| $X_4$ | N and A |
| $X_4$ | K and T |
| $X_4$ | N |
| $X_4$ | A |
| $X_4$ | K |
| $X_4$ | T |
| $X_2X_3X_4$ | NNN |
| $X_2X_3X_4$ | NAN |
| $X_2X_3X_4$ | NKN |
| $X_2X_3X_4$ | NNA |
| $X_2X_3X_4$ | KTK |

In one embodiment, the inclusion body tag further comprises additional amino acids at the C-terminal end. In one such embodiment, the inclusion body tag comprises an amino acid sequence selected from:

```
                                         (SEQ ID NO: 49)
IBF-PSLLTPRRAX38A
and (SEQ ID NO: 50)
X2X3X4-Z-IBF-PSLLTPRRAX38A;
``` wherein $X_2$, $X_3$ $X_4$, Z and IBF are as defined above; and $X_{38}$ is selected from S and T.

In one embodiment, $X_{38}$ is S.
In one embodiment, $X_{38}$ is T.
In one embodiment, $X_{38}$ is R.

In another embodiment of an inclusion body tag that comprises additional amino acids at the C-terminal end, the inclusion body tag comprises an amino acid sequence selected from:

```
                                         (SEQ ID NO: 58)
IBF-PSLLTPRR
and (SEQ ID NO: 59)
X2X3X4-Z-IBF-PSLLTPRR;
``` wherein $X_2$, $X_3$ $X_4$, Z and IBF are as defined above

As described in detail in the experimental section below, the mutational analysis of the ssTorA sequence led to the identification of a number of individual inclusion body tags, which are listed in this disclosure. These sequences constitute individual embodiments of the inclusion body tag in the fusion polypeptide according to this first aspect. Hence, in one embodiment of the fusion polypeptide according to this aspect, the sequence of the inclusion body tag is selected from the group consisting of SEQ ID NO:3-9, 11-14, 21-22, 26, 28-33 and 39-44. In another embodiment, the sequence of the inclusion body tag is selected from the group consisting of SEQ ID NO:3-9, 12-13, 21-22, 28-33, 39-41 and 44. In another embodiment, the sequence of the inclusion body tag is selected from the group consisting of SEQ ID NO:3-9, 11-14, 21-22, 26, 28-33 and 39-43. In another embodiment, the sequence of the inclusion body tag is selected from the group consisting of SEQ ID NO:3-9, 12-13, 21-22, 28-33 and 39-41. In another embodiment, the sequence of the inclusion body tag is selected from the group consisting of SEQ ID NO:4-5, 12-13, 22, 28-32 and 39-41. In another embodiment, the sequence of the inclusion body tag is selected from the group consisting of SEQ ID NO:12-13, 22, 28, 30, 32 and 39-41. In another embodiment, the sequence of the inclusion body tag is selected from SEQ ID NO:30 and 32. In another embodiment, the sequence of the inclusion body tag is selected from SEQ ID NO:12 and 13. In another embodiment, the sequence of the inclusion body tag is selected from the group consisting of SEQ ID NO:22, 28 and 39-41.

In one embodiment of the fusion polypeptide, the inclusion body tag comprises a truncated ssTorA sequence, SEQ ID NO:22. This tag sequence is denoted "ssTorA[Δ29-36]" throughout the disclosure. In an alternative embodiment, ssTorA[Δ29-36] lacks the last C-terminal alanine residue and comprises the sequence SEQ ID NO:53.

In one embodiment of the fusion polypeptide, the inclusion body tag comprises the native ssTorA sequence with a T38S mutation, SEQ ID NO:3. This tag sequence is denoted "ssTorA" throughout the disclosure.

In one embodiment of the fusion polypeptide, the inclusion body tag comprises the native ssTorA sequence, SEQ ID NO:44. This tag sequence is denoted "ssTorA[WT]" throughout the disclosure.

In an alternative embodiment, such a sequence is not part of the disclosure, but, on the contrary, is disclaimed. Thus, in this embodiment, there is provided a fusion polypeptide as defined above, but subject to the proviso that the inclusion body tag does not comprise the amino acid sequence SEQ ID NO:44.

In the fusion polypeptide according to this aspect, the inclusion body tag is fused to the polypeptide of interest.

In one embodiment, the fusion of inclusion body tag to polypeptide of interest is N-terminal. In another embodiment, it is C-terminal.

In one embodiment, the fusion polypeptide comprises more than one inclusion body tag, i.e. comprises two or more copies of an inclusion body tag as defined above, such as two consecutive copies at either or both termini, or one or more tags on either end. In such a case, each copy fulfills the sequence definition for an inclusion body tag given herein, but the copies do not necessarily have to be identical. In one embodiment, all copies of inclusion body tags in the fusion polypeptide have the same amino acid sequence. In an alternative embodiment, one or more inclusion body tag(s) in the fusion polypeptide has a sequence which differs from the sequence of one or more of the other inclusion body tag(s).

In one embodiment of the fusion polypeptide, it comprises three consecutive copies of said inclusion body tag fused to the N-terminus of said polypeptide of interest.

In one embodiment of the fusion polypeptide, it comprises at least one inclusion body tag fused to the N-terminus of the polypeptide of interest and at least one inclusion body tag fused to the C-terminus of the polypeptide of interest. In a more specific embodiment of the fusion polypeptide, it comprises three consecutive copies of said inclusion body tag fused to the N-terminus of said polypeptide of interest and three consecutive copies of said inclusion body tag fused to the C-terminus of said polypeptide of interest.

In one embodiment, the fusion polypeptide further comprises at least one cleavage element for separation of the inclusion body tag from the at least one polypeptide of interest.

The inclusion body tag comprised in the fusion polypeptide of the invention is advantageous as it induces inclusion body formation when fused to any kind of polypeptide, regardless of its inherent size, conformation and solubility. Even very soluble proteins, such as thioredoxin (TrxA) and maltose-binding protein (MBP), which are known to prevent inclusion body formation of other proteins, form inclusion bodies when fused to the inclusion body tag described herein.

The inclusion body tag enables efficient production and isolation of heterologous and homologous proteins which are otherwise very soluble and/or difficult to produce due to toxicity to the host cell and/or due to difficulties in isolation and purification from other proteins and/or cellular components of the host cell.

When fused to the inclusion body tag in the fusion polypeptide according to the first aspect of the disclosure, the polypeptide of interest (POI) is expressed and aggregated in insoluble inclusion bodies. In this form, the POI is protected from proteolytic degradation and the host cell is protected from any toxicity possibly exerted by the POI. Eliminating these adverse factors through the use of the disclosed inclusion body tag naturally leads to an increased production of the POI. The level of expression of the fusion polypeptide and thus the production of the POI is further increased with the increased number of inclusion body tags fused to the amino acid sequence of the POI. Thus, by fusion of the POI to the inclusion body tag in a fusion polypeptide according to the present disclosure, the POI can be isolated and separated in a more simplified and efficient manner.

Also, the disclosed inclusion body tag is advantageous in that it may be used on either side, or both, of the POI. Most known inclusion body tags are only tested and used at the N-terminal side of a POI. Because modification of the N-terminus of a POI may have deleterious consequences with regard to for example biological activity of the POI, the possibility to use the disclosed inclusion body tag at the C-terminal side of a POI is advantageous.

In a second aspect, the disclosure provides an inclusion body comprising a fusion polypeptide according to the first aspect. Also provided is an inclusion body obtained by the method of the sixth aspect, described below.

In a third aspect, the disclosure provides a nucleic acid molecule encoding key parts or all of the fusion polypeptide according to the first aspect.

In one embodiment of this aspect, there is provided a nucleic acid molecule comprising:
i) a nucleic acid sequence encoding at least one inclusion body tag as defined herein; and ii) a cloning site sequence which allows in-frame cloning of at least one nucleic acid sequence encoding at least one polypeptide of interest.

This embodiment of a nucleic acid molecule could for example be a cloning vector, which is ready for insertion of nucleic acid encoding a protein of interest that a user wants to express in the form of inclusion bodies.

In another embodiment of this aspect, there is provided a nucleic acid molecule comprising:
i) a nucleic acid sequence encoding at least one inclusion body tag as defined herein; and
ii) a nucleic acid sequence encoding at least one polypeptide of interest,
wherein sequences i) and ii) are arranged in a transcriptional unit encoding a fusion polypeptide according the first aspect of the disclosure.

In one embodiment of this aspect, the nucleic acid molecule further comprises a sequence comprising a promoter operably linked to said transcriptional unit, wherein said promoter is arranged to yield expression of said fusion polypeptide in inclusion bodies. For example, the promoter may be arranged to yield expression of said fusion polypeptide at a level and/or rate of expression whereby inclusion bodies comprising said fusion polypeptide are formed.

In one embodiment, the nucleic acid further comprises a sequence encoding at least one cleavage site for separation of the inclusion body tag from the at least one polypeptide of interest.

In a fourth aspect, the present disclosure provides an expression vector for expression of a fusion polypeptide as defined herein, comprising the abovementioned nucleic acid.

In one embodiment of this aspect, the expression vector comprises an origin of replication having a copy number that is high enough to yield expression of the abovementioned fusion polypeptide in inclusion bodies. For example, the expression vector may comprise an origin of replication of a copy number that is high enough to yield expression of said fusion polypeptide at a level of expression which causes inclusion bodies comprising said fusion polypeptide to be formed.

In one embodiment, the origin of replication of said expression vector yields at least 100 copies of said expression vector per host cell.

Arranging the nucleic acid in a vector provides a very beneficial way of producing the protein of interest as it allows for a fast and strong expression of the fusion polypeptide in a relatively short period of time. There are several ways in which the expression level can be enhanced. One is to include a sequence for a strong promoter in the nucleic acid, by which rapid expression kinetics are obtained and the fusion polypeptide is produced fast. Moreover, choosing a vector of a high copy number in which the nucleic acid is arranged enables multiple copies of the vector and thus of the nucleic acid encoding the fusion polypeptide to exist simultaneously in the host cell. Consequently, the fusion polypeptides are expressed in parallel from the multiple copies meaning a high expression level at a fast rate. The current invention allows for the combination of a strong, fast promoter as a part of the nucleic acid arranged in a vector of a high copy number, yielding a higher and faster expression of the fusion polypeptide.

In yet another, fifth, aspect, the disclosure provides a microbial host cell comprising the aforementioned nucleic acid or expression vector.

In one embodiment of this aspect, the microbial host cell is selected from species from the bacterial genera *Escherichia, Salmonella, Bacillus, Pseudomonas, Erwinia, Agrobacterium, Lactococcus, Vibrio, Shigella, Burkholderia, Acinetobacter, Zymomonas, Erythrobacter, Chlorobium, Chromatium, Flavobacterium, Cytophaga, Rhodobacter, Rhodococcus, Streptomyces, Brevibacterium, Corynebacteria, Mycobacterium, Deinococcus, Pantoea, Sphingomonas, Methylomonas, Methylobacter, Methylococcus, Alcaligenes, Synechocystis, Synecoccus, Anabaena, Thiobacillus, Methanobacterium, Klebsiella, Myxococcus, Bordetella* and *Caulobacter*, and species from fungal or yeast genera such as *Aspergillus, Trichoderma, Saccharomyces, Pichia, Yarrowia, Candida* and *Hansenula*.

The growth cycles and conditions regarding temperature and medium in which microbial host cells from the abovementioned genera optimally grow are generally well-known. Therefore, it is possible to maximize the yield of the expressed fusion polypeptide by harvesting the cells when the cell cultures reach stationary phase. It is also well-known in the art how to isolate inclusion bodies from such bacterial cells and cell lysates, using centrifugation or filtration techniques and combinations thereof.

In a sixth aspect, the present disclosure provides a method for producing a fusion polypeptide as disclosed herein and comprising an inclusion body tag fused to a polypeptide of interest in inclusion bodies, comprising:
i) providing a microbial host cell as defined above, and
ii) culturing said cell under conditions wherein said fusion polypeptide is expressed and inclusion bodies thereof are formed.

In one embodiment of this aspect, the conditions under which the microbial host cell is cultured to express the fusion protein include a temperature of about 37-42° C.

BRIEF DESCRIPTION OF THE FIGURES

FIG. 5. SDS-PAGE analysis of the expression of A) hEGF and B) IL-3 in inclusion bodies upon N-terminal fusion of various signal sequences as indicated to hEGF and IL-3, respectively. Non-processed (*) and processed (>) forms of the respective fusion polypeptides are indicated. Molecular mass (kDa) markers are indicated at the left side of the panels. The analysis shows both anhydrotetracycline (+ ahtc) induced expression and non-induced (− ahtc) expression.

FIG. 6. Phase contrast microscopy analysis of expression of A) hEGF and B) IL-3 in inclusion bodies upon N-terminal fusion of the signal sequence from TorA. The figures show both anhydrotetracycline (+ ahtc) induced expression (lower square) and non-induced (− ahtc) expression (upper square).

FIG. 7. SDS-PAGE analysis of the expression of A) thioredoxin A, TrxA, and B) maltose binding protein, MBP, under different conditions. FIG. 7A shows analysis of TrxA alone and in N-terminal fusion of single and double (2×) ssTorA. FIG. 7B shows analysis of MBP alone and in N-terminal fusion of single, double (2×) and triple (3×)

ssTorA. Whole cell sample (WC), insoluble material including inclusion bodies (IB) and soluble proteins (S) are indicated. TrxA and MBP (fusion) protein bands of interest (*) and bands corresponding to exogenous, added lysozyme (Lys) are indicated. Molecular mass (kDa) markers are indicated at the left side of the panels.

FIG. 8. Phase contrast microscopy analysis of inclusion body formation of TrxA after expression of A) empty vector, B) TrxA alone and C) TrxA in fusion with ssTorA. The formation of IBs is shown by the appearance of white spherical entities in cells expressing the fusion polypeptide ssTorA/TrxA (indicated by arrow in FIG. 8C).

Figure 9A:
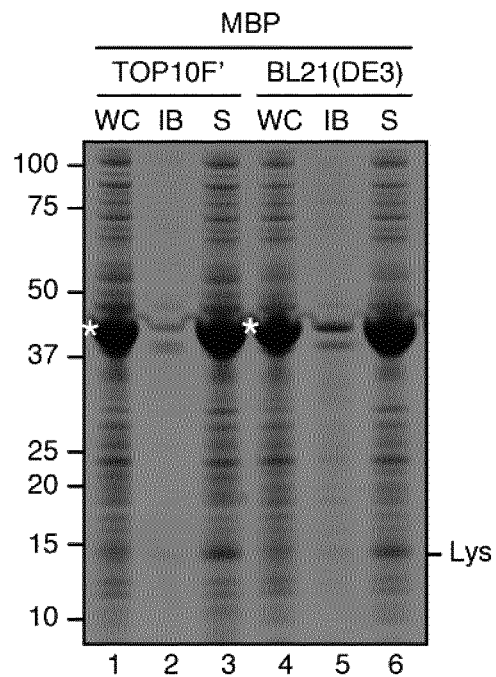
Figure 9B:
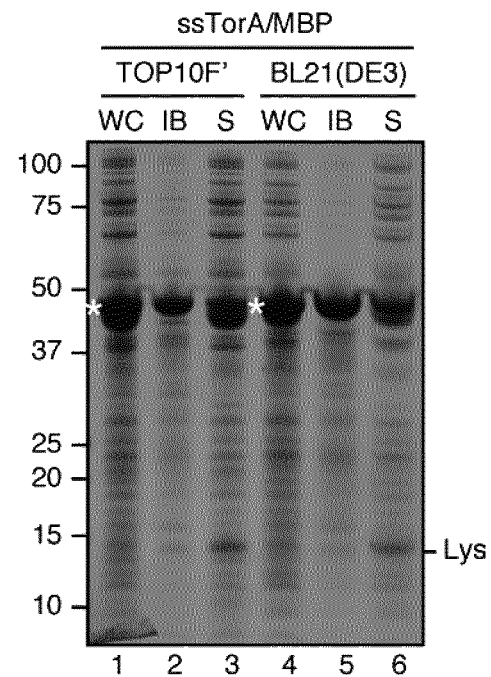

FIG. 9. SDS-PAGE analysis of inclusion body formation in *E. coli* strains TOP10F' and BL21 (DE3), after culture of A) strains TOP10F' and BL21(DE3) carrying pIBA-MBP (without ssTorA) and B) strains TOP10F' and BL21(DE3) carrying pIBA-ssTorA/MBP. Whole cell sample (WC), insoluble material including inclusion bodies (IB) and soluble proteins (S) are indicated. Protein bands of interest (*) and bands corresponding to exogenous, added lysozyme (Lys) are indicated. Molecular mass (kDa) markers are indicated at the left side of the panels.

FIG. 10. SDS-PAGE analysis of the role of twin-arginine motif in IB formation and the effect of replacement of RR by A) KK and B) AA. Non-processed (*) and processed (>) forms of the respective fusion polypeptides are indicated. Whole cell sample (WC), insoluble material including inclusion bodies (IB) and soluble proteins (S) are indicated. Bands corresponding to exogenous, added lysozyme (Lys) are also indicated. Molecular mass (kDa) markers are indicated at the left side of the panels.

FIG. 11. SDS-PAGE analysis of the role of the triple Asn motif of ssTorA and the effect on inclusion body formation of replacing NNN by A) NAN, NKN and NNA or B) KTK. Whole cell sample (WC), insoluble material including inclusion bodies (IB) and soluble proteins (S) are indicated. Non-processed (*) forms of the respective fusion polypeptides are indicated. Bands corresponding to exogenous, added lysozyme (Lys) are also indicated. Molecular mass (kDa) markers are indicated at the left side of the panels.

FIG. 12. SDS-PAGE analysis of role the of N- and C-terminal moieties of ssTorA in IB formation. FIG. 12A shows results with ssTorA/TrxA (WT), ssTorA with a C-terminal part only (C') and ssTorA with an N-terminal part only (N'). FIG. 12B shows results with ssTorA/TrxA (WT), ssTorA with a C-terminal part and inserted NNN sequence at positions 2-4 (C'+NNN)) and ssTorA with a C-terminal part and inserted KTK sequence at positions 2-4 (C'+KTK). Whole cell sample (WC), insoluble material including inclusion bodies (IB) and soluble proteins (S) are indicated. Non-processed (*) forms of the respective fusion polypeptides are indicated. Bands corresponding to exogenous, added lysozyme (Lys) are also indicated. Molecular mass (kDa) markers are indicated at the left side of the panels.

Figure 13:
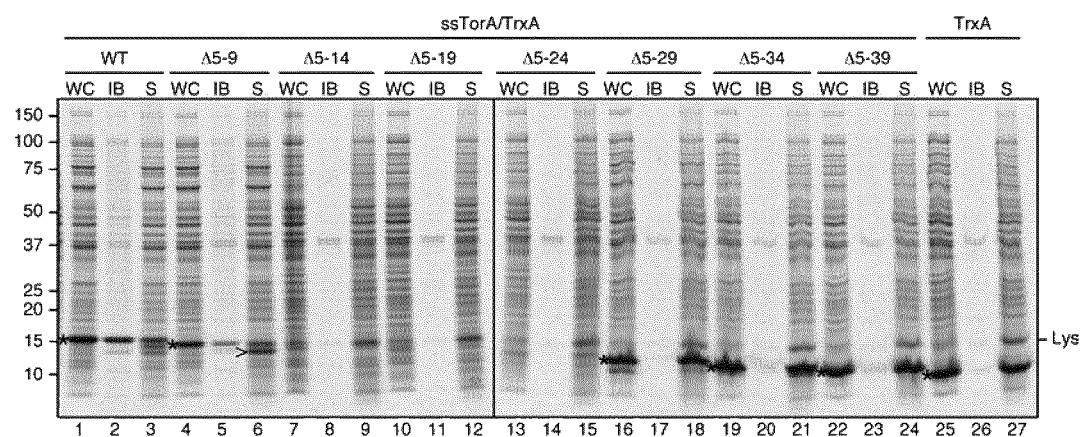

FIG. 13. SDS-PAGE analysis of N' to C' progressive deletion of ssTorA, illustrating deletion of amino acid residues 5-39 (Δ5-9, Δ5-14, Δ5-19, Δ5-24, Δ5-29, Δ5-34 and Δ5-39) compared to ssTorA (WT) as indicated. Whole cell sample (WC), insoluble material including inclusion bodies (IB) and soluble proteins (S) are indicated. Non-processed (*) forms of the respective fusion polypeptides are indicated. Bands corresponding to exogenous, added lysozyme (Lys) are also indicated. Molecular mass (kDa) markers are indicated at the left side of the panels.

Figure 14:
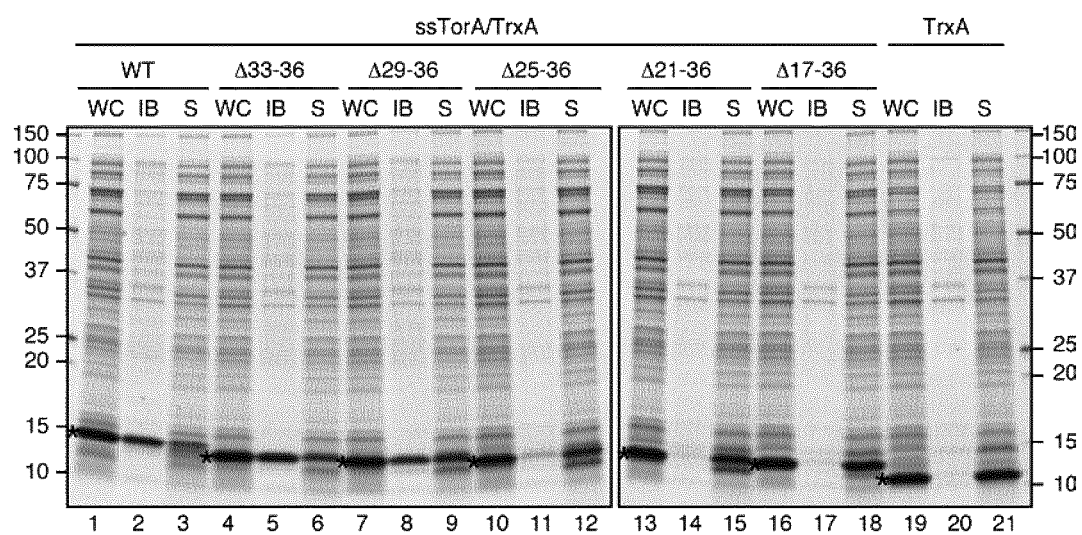

FIG. 14. SDS-PAGE analysis of C' to N' progressive deletion of ssTorA, illustrating deletion of amino acid residues 17-36 (Δ17-36, Δ21-36, Δ25-36, Δ29-36 and Δ33-36) compared to ssTorA (WT) as indicated. Whole cell sample (WC), insoluble material including inclusion bodies (IB) and soluble proteins (S) are indicated. Non-processed (*) forms of the respective fusion polypeptides are indicated. Bands corresponding to exogenous, added lysozyme (Lys) are also indicated. Molecular mass (kDa) markers are indicated at the left side of the panels.

Figure 15:
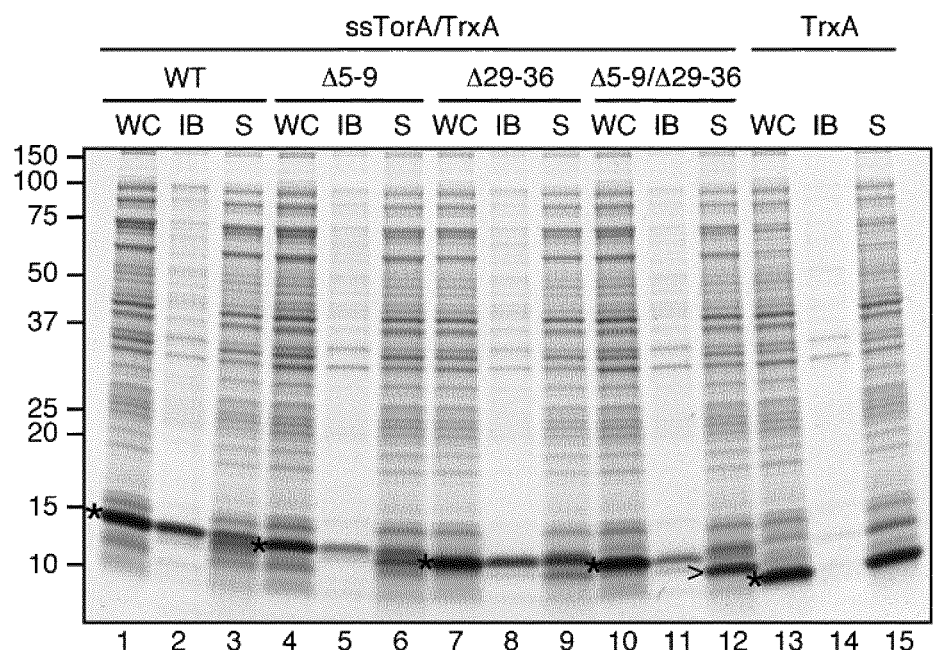

FIG. 15. SDS-PAGE analysis of combined N' and C' deletion of ssTorA, illustrating the deletion of amino acid residues 5-9 (Δ5-9) and 29-36 (Δ29-36) individually and in combination (Δ5-9/Δ29-36) in comparison with ssTorA/TrxA (WT) and TrxA. Whole cell sample (WC), insoluble material including inclusion bodies (IB) and soluble proteins (S) are indicated. Non-processed (*) and processed (>) forms of the respective fusion polypeptides are indicated. Bands corresponding to exogenous, added lysozyme (Lys) are also indicated. Molecular mass (kDa) markers are indicated at the left side of the panels.

Figure 16:
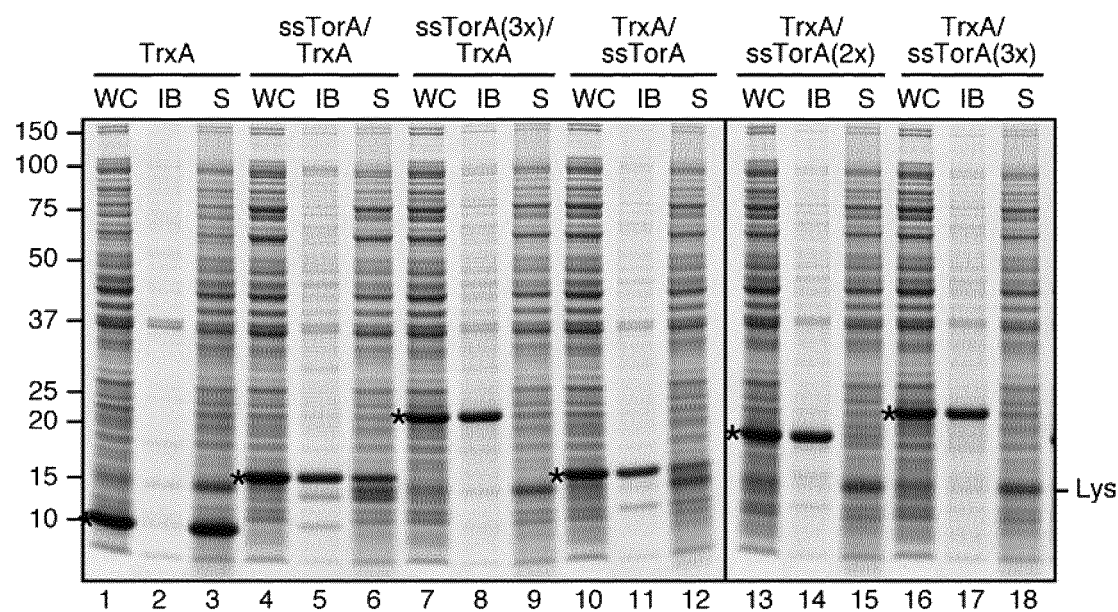

FIG. 16. SDS-PAGE analysis of inclusion body formation upon C-terminal fusion of ssTorA and of repeated ssTorA inclusion body tag sequences, illustrating expression of TrxA in IBs upon C-terminal fusion of ssTorA (lanes 10-12). Enhanced expression of TrxA in IBs upon fusion to repeats of ssTorA (doublets: 2x; triplets: 3x) at the C-terminus (lanes 13-15; lanes 16-18) is shown. Whole cell sample (WC), insoluble material including inclusion bodies (IB) and soluble proteins (S) are indicated. Non-processed (*) forms of the respective fusion polypeptides are indicated. Bands corresponding to exogenous, added lysozyme (Lys) are also indicated. Molecular mass (kDa) markers are indicated at the left side of the panels.

FIG. 17. SDS-PAGE analysis of inclusion body formation of *E. coli* enzyme chloramphenicol acetyltransferase (CAT) upon fusion to ssTorA or ssTorA[N'] as indicated. Whole cell sample (WC), insoluble material including inclusion bodies (IB) and soluble proteins (S) are indicated. Non-processed (*) forms of the respective fusion polypeptides are indicated. Bands corresponding to exogenous, added lysozyme (Lys) are also indicated. Molecular mass (kDa) markers are indicated at the left side of the panels.

FIG. 18. SDS-PAGE analysis of the influence on IB formation of A16P and F14Y substitutions in ssTorA in context of ssTorA/CAT as described in Example 14. Whole cell sample (WC), insoluble material including inclusion bodies (IB) and soluble proteins (S) are indicated. Non-processed (*) and processed (>) forms of the respective fusion polypeptides are indicated. Bands corresponding to exogenous, added lysozyme (Lys) are also indicated. Molecular mass (kDa) markers are indicated at the left side of the panels.

FIG. 19. A) SDS-PAGE analysis of the expression of full-length TorA carrying a C-terminal HA tag (TorA(HA)) in inclusion bodies when expressed from the vector pBAD24 under control of the araBAD promoter. Whole cell sample (WC), insoluble material including inclusion bodies (IB) and soluble proteins (S) are indicated. Non-processed (*) forms of the respective fusion polypeptides are indicated. Bands corresponding to exogenous, added lysozyme (Lys) are also indicated. Molecular mass (kDa) markers are indicated at the left side of the panels. B) Micrograph of the expression of TorA(HA) in IBs in *E. coli* cells (indicated by arrows).

Figure 20:
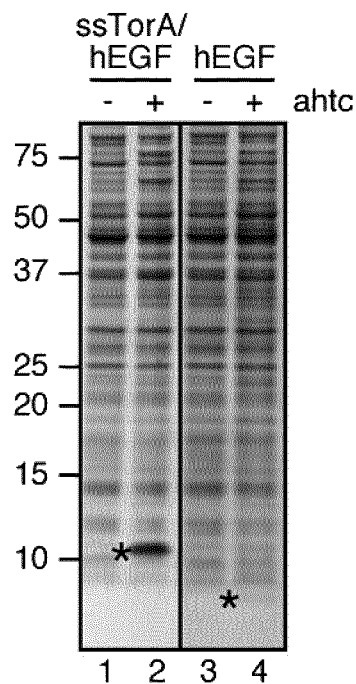

FIG. 20. SDS-PAGE analysis of the expression of an unstable protein (hEGF) upon fusion to ssTorA (ssTorA/hEGF) as indicated, showing samples withdrawn from the cultures at the time point of induction (− ahtc) and 2 hours after induction (+ ahtc). The hEGF-(fusion) protein band (*) is indicated. Molecular mass (kDa) markers are indicated at the left side of the panel.

Figure 21A:
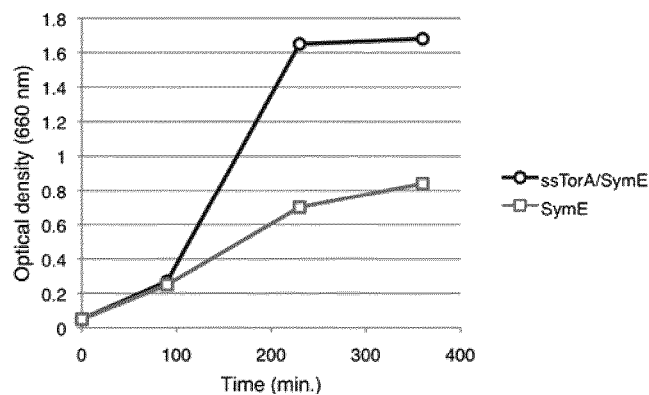

FIG. 21. Expression of a toxic protein upon fusion to ssTorA. A) Optical density of *E. coli* culture over time, for cells expressing toxic SymE or SymE in fusion with ssTorA as indicated. B) SDS-PAGE analysis of the expression of SymE upon fusion to ssTorA (ssTorA/SymE) in comparison with expression of SymE without ssTorA as indicated (*). Whole cell sample (WC), insoluble material including inclusion bodies (IB) and soluble proteins (S) are indicated. Bands corresponding to exogenous, added lysozyme (Lys) are also indicated. Molecular mass (kDa) markers are indicated at the left side of the panels.

Figure 22:
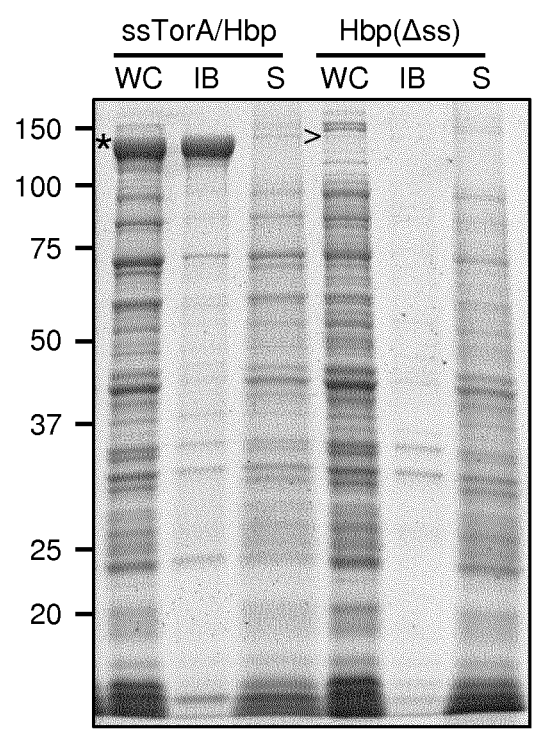

FIG. 22. SDS-PAGE analysis of the expression of a large, unstable Hbp derivative protein [Hbp(Δss)] into IBs under the control of an IPTG-inducible promoter (*). ssTorA/Hbp is recovered only from the IB fraction when expressed under these conditions (lane 2). In contrast, Hbp(Δss) analyzed under the same conditions is detected at very low levels (indicated by > in lane 4). Whole cell sample (WC), insoluble material including inclusion bodies (IB) and soluble proteins (S) are indicated. Molecular mass (kDa) markers are indicated at the left side of the panels.

Figure 23:
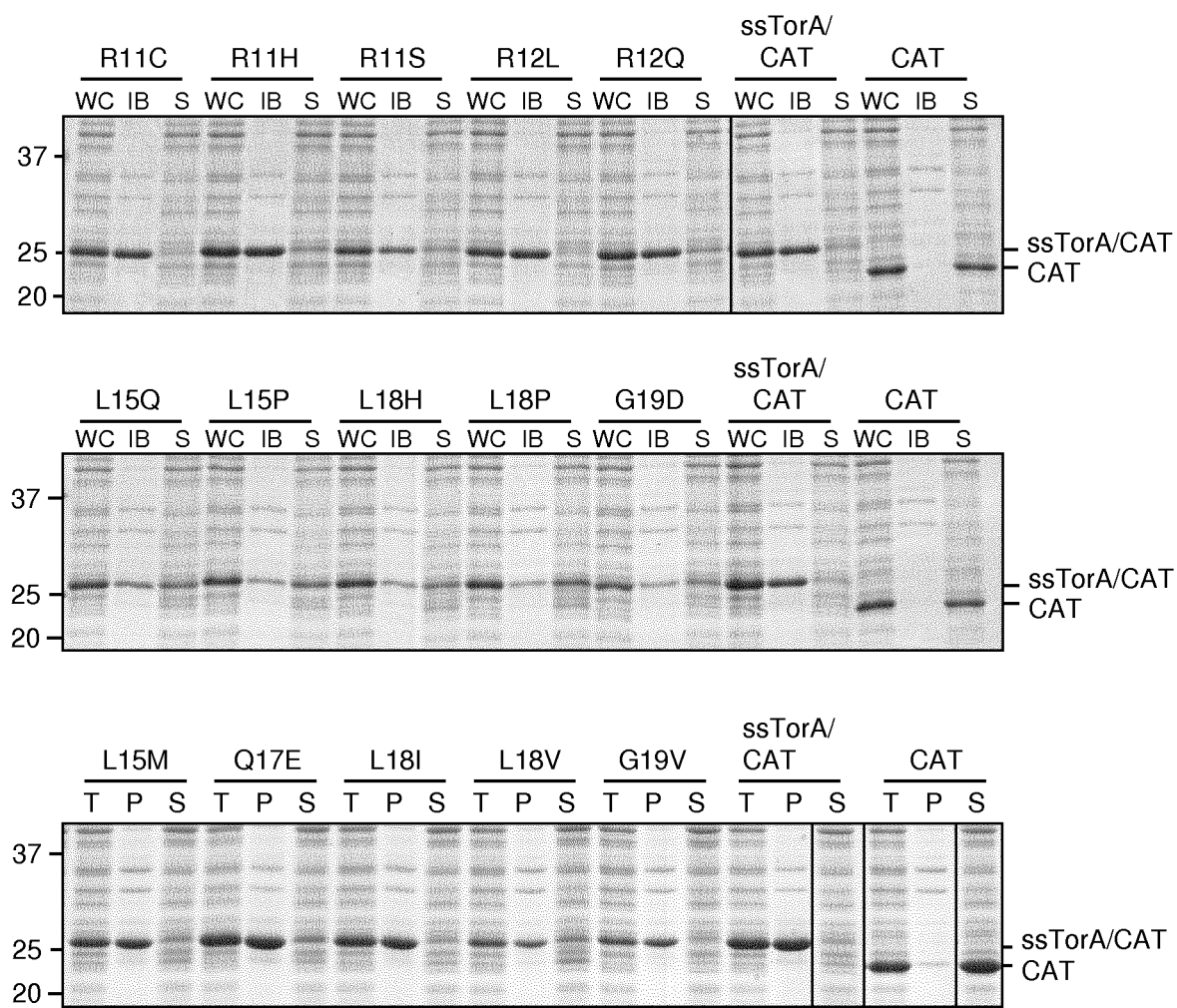

FIG. 23. SDS-PAGE analysis of IB formation upon amino acid substitution in ssTorA in the context of CAT to identify sequence variants of ssTorA sustaining IB formation. The indicated substitution mutants of ssTorA were analyzed. Whole cell sample (WC or T), insoluble material including inclusion bodies (IB or P) and soluble proteins (S) are indicated. Molecular mass (kDa) markers are indicated at the left side of the panels.

Figure 24:
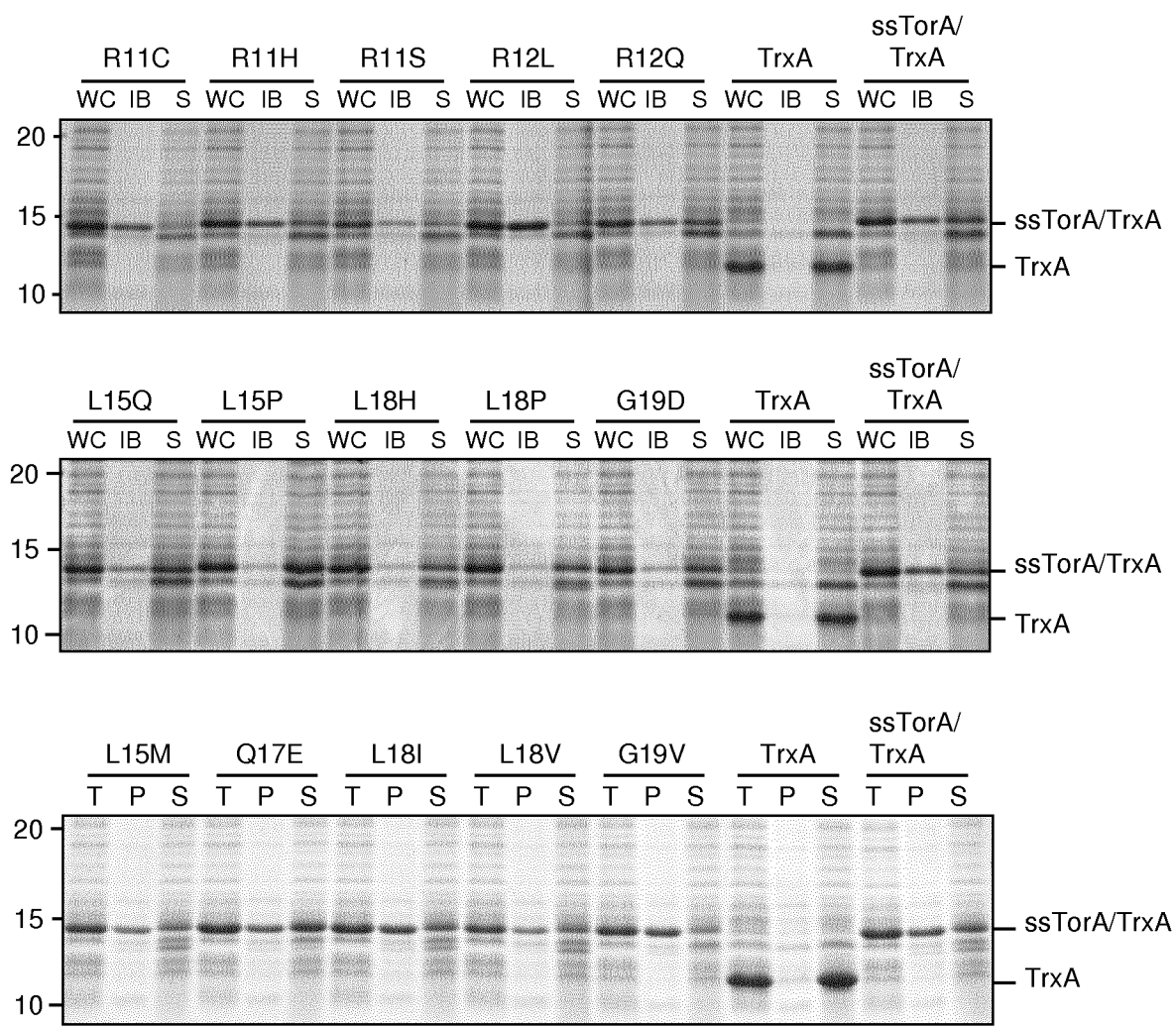

FIG. 24. SDS-PAGE analysis of IB formation upon amino acid substitution in ssTorA in the context of TrxA to identify sequence variants of ssTorA sustaining IB formation. The indicated substitution mutants of ssTorA were analyzed. Whole cell sample (WC or T), insoluble material including inclusion bodies (IB or P) and soluble proteins (S) are indicated. Molecular mass (kDa) markers are indicated at the left side of the panels.

FIG. 25. SDS-PAGE (A, C) and phase-contrast microscopy (B) analysis of IB formation upon fusion to truncated ssTorA and to repeats thereof. (A, C) Whole cell sample (WC), insoluble material including inclusion bodies (IB) and soluble proteins (S) are indicated. GFP fusion polypeptides (*) and a proteolytic product of a GFP fusion polypeptide (<) are indicated. Molecular mass (kDa) markers are indicated at the left side of the panel. (B) Examples of IBs are indicated (arrow head). Scale bar: 2 μm.

FIG. 26. SDS-PAGE (A) and phase contrast microscopy (B) analysis of IB formation upon fusion to ssTorA and derivatives thereof, compared to fusion to KSI. (A) Whole cell sample (WC), insoluble material including inclusion bodies (IB) and soluble proteins (S) are indicated. GFP fusion polypeptides (*) are indicated. Molecular mass (kDa) markers are indicated at the right hand side of the panel. (B) Examples of IBs are indicated (arrow head). Scale bar: 2 μm.

Figure 27:
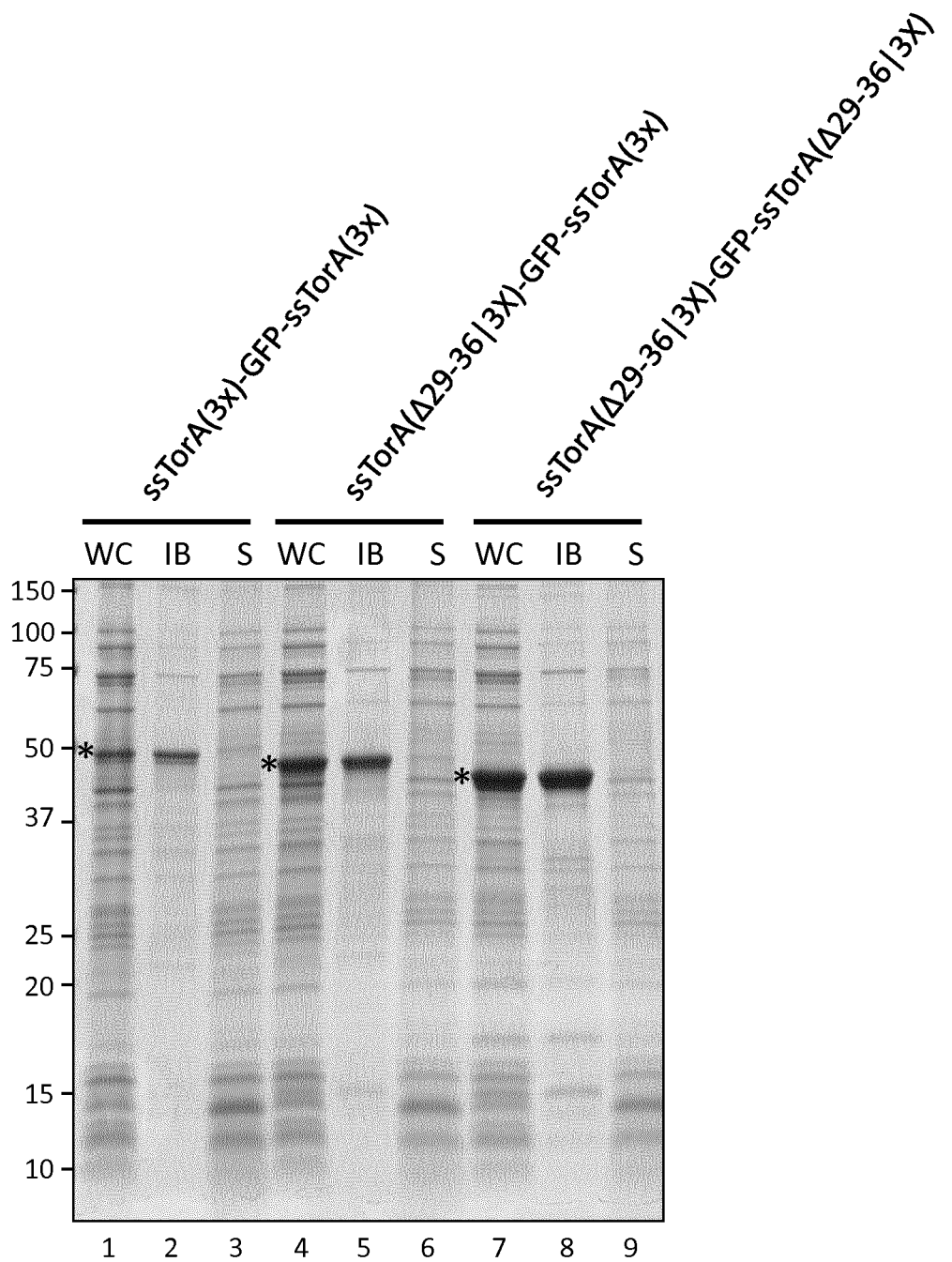

FIG. 27. SDS-PAGE analysis of IB formation upon simultaneous fusion of repeats of ssTorA or an abridged derivative thereof at the N- and C-termini of GFP. Whole cell sample (WC), insoluble material including inclusion bodies (IB) and soluble proteins (S) are indicated. GFP fusion polypeptides (*) are indicated. Molecular mass (kDa) markers are indicated at the left side of the panel.

FIG. 28. SDS-PAGE (A) and phase contrast microscopy (B) analysis of IB formation upon fusion to tandem repeats of an abridged derivative of ssTorA to a panel of various model proteins. (A) Whole cell sample (WC), insoluble material including inclusion bodies (IB) and soluble proteins (S) are indicated. Overexpressed fusion polypeptides (*) are indicated. Molecular mass (kDa) markers are indicated at the left side of the panel. (B) Examples of IBs are indicated (arrow head). Scale bar: 2 μm.

BRIEF DESCRIPTION OF THE SEQUENCES

Table 3 below lists the designations and SEQ ID NO:s of the different fusion tags used and exemplified herein.

TABLE 3

| Designation | SEQ ID NO: |
| --- | --- |
| Generic IBF - short | 1 |
| Generic IBF - long | 2 |
| ssTorA | 3 |
| ssTorA[RR/KK] | 4 |
| ssTorA[RR/AA] | 5 |
| ssTorA[NNN/NAN] | 6 |
| ssTorA[NNN/NKN] | 7 |
| ssTorA[NNN/NNA] | 8 |
| ssTorA[NNN/KTK] | 9 |
| ssTorA[N'] | 10 |
| ssTorA[C'] | 11 |
| ssTorA[C' + NNN] | 12 |
| ssTorA[C' + KTK] | 13 |
| ssTorA[Δ5-9] | 14 |
| ssTorA[Δ5-14] | 15 |
| ssTorA[Δ5-19] | 16 |
| ssTorA[Δ5-24] | 17 |
| ssTorA[Δ5-29] | 18 |
| ssTorA[Δ5-34] | 19 |
| ssTorA[Δ5-39] | 20 |
| ssTorA[Δ33-36] | 21 |
| ssTorA[Δ29-36] | 22 |
| ssTorA[Δ25-36] | 23 |
| ssTorA[Δ21-36] | 24 |
| ssTorA[Δ17-36] | 25 |
| ssTorA[Δ5-9/Δ29-36] | 26 |
| ssTorA[A16P] | 27 |
| ssTorA[F14Y] | 28 |
| ssTorA[R11C] | 29 |
| ssTorA[R11H] | 30 |
| ssTorA[R11S] | 31 |
| ssTorA[R12L] | 32 |
| ssTorA[R12Q] | 33 |
| ssTorA[L15Q] | 34 |
| ssTorA[L15P] | 35 |
| ssTorA[L18H] | 36 |
| ssTorA[L18P] | 37 |
| ssTorA[G19D] | 38 |
| ssTorA[L15M] | 39 |
| ssTorA[Q17E] | 40 |
| ssTorA[L18I] | 41 |
| ssTorA[L18V] | 42 |
| ssTorA[G19V] | 43 |
| ssTorA[WT] | 44 |
| ssTorA[Δ29-36]$_{GFP}$ | 53 |
| ssTorA[Δ29-36|2x]$_{GFP}$ | 54 |
| ssTorA[Δ29-36|3x]$_{GFP:N}$ | 55 |
| ssTorA[Δ29-36|3x]$_{GFP:C}$ | 56 |
| ssTorA[Δ29-36|3x] | 57 |

Definitions

As used herein, the following definitions are supplied in order to facilitate the understanding of the present invention.

As used herein, the term "inclusion body", abbreviated "IB", refers to an insoluble deposit of aggregated polypeptides in the cytoplasm or nucleus of a cell. Herein, the term mainly refers to inclusion bodies formed within the cytoplasm of prokaryotic, bacterial cells. The term may also refer to polypeptide aggregates in the cytoplasm and/or nucleus of eukaryotic cells. Inclusion bodies may form spontaneously within a host cell, for example as the result of overexpression of insoluble or partly insoluble polypeptides. However, in the present disclosure, a polypeptide of interest that is normally soluble or partly soluble within a host cell may be fused to an IB tag, resulting in a fusion polypeptide comprising the polypeptide of interest operably linked to the inclusion body tag. When the fusion polypeptide is expressed, the inclusion body tag induces the fusion polypeptide, and thus the polypeptide of interest, to form inclusion bodies. The aggregated polypeptides contained in the inclusion bodies may be misfolded, partly misfolded or may have a native or nearly native fold. The insoluble form of a polypeptide in an inclusion body protects the polypeptide from degradation by proteolytic enzymes within the host cell. Moreover, it protects the host cell from any toxic effect that the polypeptide might have in its soluble, native form. Also, the formation of inclusion bodies may facilitate isolation and purification of certain polypeptides that are otherwise difficult to purify or that otherwise require many and/or expensive purification steps. Means and methods to identify inclusion bodies and quantify inclusion body formation are well known in the art. Such means and methods include inclusion body fractionation assay, phase contrast microscopy, other optical measuring techniques, particle size measurements, gel separation assays (e.g. SDS-PAGE), proteolytic digestion and electron microscopy.

The terms "inclusion body tag" and "inclusion body forming tag" refer to a polypeptide sequence that induces formation of inclusion bodies when fused to a polypeptide of interest. The inclusion body tag causes a fusion polypeptide comprising the polypeptide of interest and the inclusion body tag to aggregate in inclusion bodies. An inclusion body tag may be comprised of a protein entity or a polypeptide entity.

The term "polypeptide" is herein used to designate a series of two or more amino acid residues connected to one another by peptide bonds between the alpha-amino and carboxy groups of adjacent residues. The term is used to designate a peptide of unspecified length. Thus, peptides, oligopeptides, polypeptides and proteins are included within the definition of a "polypeptide" herein. The term "peptide" is herein used to designate a short polypeptide, for example having a length of about two amino acids to about 50 amino acids. The term "protein" is herein used to designate longer and/or more complex polypeptides, such as a complex of two or more polypeptide chains. A protein may also be bound to cofactors or other proteins. The terms "peptide", polypeptide" and "protein" may also include posttranslational modifications, such as glycosylations, acetylations, phosphorylations etc. Polypeptides comprising one or more amino acid analogue or labeled amino acid are also included within the definition.

The interchangeable terms "polypeptide sequence", "peptide sequence" and "protein sequence" refer to the order of amino acids in a polypeptide, peptide or protein. As is conventional, a polypeptide sequence is herein generally reported from the N-terminal end to the C-terminal end.

The terms "polypeptide of interest", "peptide of interest" and "protein of interest", abbreviated "POI", are used interchangeably to refer to a polypeptide, peptide or protein that is of interest to a user of the present invention and that may be expressed by the genetic machinery of a host cell, e.g. as a recombinant protein. The terms are also meant to be equivalent to the commonly used terms "target protein", "target polypeptide", "target peptide", "expressible polypeptide" or "expressible protein". The POI can be any type of POI. For example, the POI may be a) a heterologous or homologous polypeptide, b) a soluble or partly soluble cytoplasmic polypeptide, a soluble or partly soluble secretory polypeptide or a membrane polypeptide. In embodiments of particularly advantageous use, the POI is a polypeptide that is toxic to the host cell, that degrades easily in the host cell or that is difficult to purify from the host cell when in soluble form. The POI is of any length. In particular, the POI may be at least from about 10, 25 or 50 amino acids long, and may be up to 1000, 1500, 2000, 3000 or 5000 amino acids long.

By "heterologous polypeptide" or "polypeptide heterologous to a host" is meant a polypeptide that is foreign to the host, i.e. a polypeptide originating from a donor different from the host or a chemically synthesized polypeptide that is foreign to the host. In case the host is a particular prokaryotic species, the heterologous polypeptide preferably originates from a different genus or family, more preferred from a different order or class, in particular from a different phylum (division) and most particular from a different domain (empire) of organisms.

The terms "homologous polypeptide" and "polypeptide homologous to a host" mean a polypeptide that is from the host, i.e. a polypeptide originating from the host or a chemically synthesized polypeptide with an amino acid sequence that originates from the host.

The terms "fusion polypeptide", "fusion protein" and "fusion peptide" refer to a polymer of amino acids, i.e. a polypeptide, protein or peptide, comprising at least two portions, each portion representing a distinct function and/or origin. A fusion polypeptide of the present invention comprises, in any order, at least a first portion comprising the disclosed inclusion body tag and at least a second portion comprising a polypeptide of interest. The fusion polypeptide of the present invention may in alternative embodiments comprise more than one inclusion body tag and/or more than one POI. It may also comprise further portions comprising other functionalities, such as a cleavable element for separation of the inclusion body tag(s) from the POI(s).

The terms "cleavable element", "cleavage element", "cleavable site" and "cleavage site" are used interchangeably and refer to elements that enable cleavage at a selected site of an amino acid sequence by use of a chemical entity, such as an enzyme, or a method that imparts specific cleavage at the element. The cleavage element is for example an amino acid sequence of between about 1 and 50 amino acids, the amino acid sequence being recognized by a specific protease or being sensitive to a specific chemical. An example of a cleavage element that does not require use of proteases is self-cleaving inteines, e.g. the inteine tags in the IMPACT™ kit from New England Biolabs®, cleaved in the presence of thiols such as DDT. Other autocatalytical cleavage elements are also known in the art.

The term "solubility" refers to the amount of a substance that can be dissolved in a unit volume of a liquid under certain conditions. Herein solubility is mainly discussed with regard to the ability of a peptide, such as a polypeptide of interest, an inclusion body tag or a fusion polypeptide comprising a POI fused to an inclusion body tag, to be dissolved in a volume of solvent. The solvent may for instance be a biological buffer. In one embodiment, the native POI is soluble in the host cell used for protein production under normal physiological conditions. That is, the native POI does not precipitate in the cell when expressed under normal physiological conditions. Fusion of the POI to the inclusion body tag, on the other hand, results in a fusion polypeptide that is insoluble in the host cell under normal physiological conditions. That is, the fusion polypeptide aggregates into inclusion bodies when expressed under normal physiological conditions. In one embodiment, the native POI is soluble in an aqueous matrix having a pH of 6-10 and a temperature range of 5-50° C., preferably 10-45° C.

The terms "operably linked" and "coupled" refer to the association of a first portion of a polypeptide or a nucleic acid fragment with a second portion of the polypeptide or nucleic acid fragment, such that the function of one of the portions is affected by the other. For example, a fusion polypeptide according to the invention comprises a POI operably linked to an inclusion body tag, meaning that the POI is linked to and affected by the inclusion body tag, but that the two parts are not necessarily contiguously fused. Similarly, with regard to nucleic acids, a promoter may for instance be operably linked to coding sequence, for example coding for a fusion polypeptide according to the invention, meaning that the promoter is able to affect the expression of the coding sequence, i.e. that the coding sequence is under transcriptional control of the promoter. A translation initiation region such as a ribosome binding site is operably linked to a nucleic acid sequence encoding e.g. a polypeptide, if it is positioned so as to facilitate translation of the polypeptide.

The terms "nucleic acid", "nucleic acid molecule" and "nucleic acid fragment", as referred to in the present disclosure, represent a polymer of DNA or RNA or a DNA/RNA hybrid, optionally comprising synthetic, non-natural or altered nucleotide bases. In case the nucleic acid is located on a vector, it is usually DNA. DNA which is referred to herein can be any polydeoxynucleotide sequence, including, e.g., double-stranded DNA, single-stranded DNA, double-stranded DNA wherein one or both strands are composed of two or more fragments, double-stranded DNA wherein one or both strands have an uninterrupted phosphodiester backbone, DNA containing one or more single-stranded portion(s) and one or more double-stranded portion(s), double-stranded DNA wherein the DNA strands are fully complementary, double-stranded DNA wherein the DNA strands are only partially complementary, circular DNA, covalently closed DNA, linear DNA, covalently cross-linked DNA, cDNA, chemically synthesized DNA, semi-synthetic DNA, biosynthetic DNA, naturally isolated DNA, enzyme-digested DNA, sheared DNA, labeled DNA, such as radiolabeled DNA and fluorochrome-labeled DNA, DNA containing one or more non-naturally occurring species of nucleic acid. DNA fragments can be synthesized by standard chemical techniques, for example the phosphotriester method, or via automated synthesis methods or PCR methods. A purified and isolated DNA fragment may also be produced by enzymatic techniques.

RNA which is referred to herein can be e.g. single-stranded RNA, cRNA, double-stranded RNA, double-stranded RNA wherein one or both strands are composed of two or more fragments, double-stranded RNA wherein one or both strands have an uninterrupted phosphodiester backbone, RNA containing one or more single-stranded portion(s) and one or more double-stranded portion(s), double-stranded RNA wherein the RNA strands are fully complementary, double-stranded RNA wherein the RNA strands are only partially complementary, covalently cross-linked RNA, enzyme-digested RNA, sheared RNA, mRNA, chemically synthesized RNA, semi-synthetic RNA, biosynthetic RNA, naturally isolated RNA, labeled RNA, such as radiolabeled RNA and fluorochrome-labeled RNA, RNA containing one or more non-naturally occurring species of nucleic acid.

The terms "nucleic acid sequence" and "nucleotide sequence" refer to the order of nucleotides in a nucleic acid, nucleic acid molecule or nucleic acid fragment. As is conventional, a nucleic acid sequence is herein generally reported from the 5' end to the 3' end.

The terms "isolated nucleic acid", "isolated nucleic acid molecule" and "isolated nucleic acid fragment" refer to a nucleic acid that is free or substantially free of material with which it is naturally associated, such as other nucleic acids or cellular constituents with which it is found in its natural environment, or constituents from the environment in which it is prepared (e.g. cell culture), when such preparation is by recombinant technology practiced in vitro or in vivo.

A "heterologous nucleic acid", "heterologous nucleic acid sequence" or "nucleic acid heterologous to a host" is a nucleic acid or nucleic acid sequence which originates from a donor different from the host and/or encodes an expression product such as a polypeptide that is foreign to the host ("heterologous expression" or "heterologous product"). The heterologous nucleic acid may be derived from a donor cell which is different from the host cell, or may be a chemically synthesized nucleic acid which has a nucleotide sequence or encodes a polypeptide that is foreign to the host. In case the host is a particular prokaryotic species, the heterologous nucleic acid preferably originates from a different genus or family, more preferred from a different order or class, in particular from a different phylum (division) and most particular from a different domain (empire) of organisms.

A heterologous nucleic acid originating from a donor different from the host can be modified before it is introduced into a host cell, by mutations, insertions, deletions or substitutions of single nucleotides or a part of the heterologous nucleic acid as long as such modified nucleic acids exhibit the same function (functionally equivalent) as the reference nucleic acid. A heterologous nucleic acid as referred herein encompasses as well nucleic acids originating from a different domain (empire) of organisms such as from eukaryotes (of eukaryotic origin) such as e.g., human antibodies which have been used in phage display libraries and of which single nucleic acids or a part of the nucleic acid sequences have been modified according to the "codon usage" of a host.

A "homologous nucleic acid", "homologous nucleic acid sequence" or "nucleic acid homologous to a host" is a nucleic acid or nucleic acid sequence which is naturally present in the host cell and/or which encodes e.g., an expression product such as a polypeptide that is from the host ("homologous expression" or "homologous product") i.e., a nucleic acid originating from the host or a chemically synthesized nucleic acid which encodes e.g., an expression product such as a polypeptide that is from the host.

A "substantially identical" nucleic acid sequence or polypeptide sequence is a nucleic acid or polypeptide sequence that differs from a reference sequence by one or more conservative substitutions, or by one or a few non-conservative substitutions, deletions, or insertions. Conservative substitution with regard to polypeptides is substitution of an amino acid to another amino acid whose side chains has similar biochemical properties. Conservative substitution with regard to nucleic acid sequences means a substitution of a nucleotide such that, in case the nucleic acid sequence is a coding sequence, the substituted nucleic acid sequence encodes the same amino acid or a similar amino acid as the original sequence, or such that, in case the nucleic acid sequence is a non-coding sequence, the substituted nucleic acid sequence retains the same function, to a similar extent, as the original nucleic acid sequence.

A substantially identical sequence can be any value from 10% to 99%, or more generally at least 10%, 20%, 30%, 40%, 50, 55% or 60%, or at least 65%, 75%, 80%, 85%, 90%, or 95%, or as much as 96%, 97%, 98%, or 99% identical to the reference sequence, when optimally aligned at the amino acid or nucleotide level using, for example, the Align Program 18 or FASTA. The length of comparison sequences may be at least 5, 10, 15, 20, or 25 nucleotides or amino acids, or at least 30, 40, or 50 nucleotides or amino acids. In alternate embodiments, the length of comparison sequences may be at least 60, 70, 80, or 90 nucleotides or amino acids, or over 100, 200, or 500 nucleotides or amino acids.

Sequence identity can be readily measured using publicly available sequence analysis software (e.g., Sequence Analysis Software Package of the Genetics Computer Group, University of Wisconsin Biotechnology Center, 1710 University Avenue, Madison, Wis.; 53705, or BLAST software available from the National Library of Medicine, or as described herein). Examples of useful software include the programs Pile-up and PrettyBox. Such software matches similar sequences by assigning degrees of homology to various substitutions, deletions, substitutions, and other modifications. Substantially identical sequences include homologous sequences, such as COPI related sequences from non-human species as described herein or known in the art.

Alternatively, or additionally, two nucleic acid sequences may be "substantially identical" if they hybridize under high stringency conditions. High stringency hybridization is also relied upon for the success of numerous techniques routinely performed by molecular biologists, such as high stringency PCR, DNA sequencing, single strand conformational polymorphism analysis, and in situ hybridization. In contrast to northern and Southern hybridizations, these techniques are usually performed with relatively short probes (e.g., usually about 16 nucleotides or longer for PCR or sequencing and about 40 nucleotides or longer for in situ hybridization). The high stringency conditions used in these techniques are well known to those skilled in the art of molecular biology, and examples of them can be found, for example, in Ausubel et al., Current Protocols in Molecular Biology, John Wiley and Sons.

The terms "variant", "variant of a sequence", "variant gene" are "variant polypeptide", as well as "derivative", "derivative of a sequence", "derivative gene" and "derivative polypeptide", all refer to a polypeptide or nucleic acid sequence that varies from a reference sequence either by conservative substitutions, as defined above, or by non-conservative substitutions that maintain the function of the reference sequence. Variants and derivatives encompass degenerated sequences as well as sequences with deletions and insertions, as long as such variant or derivative sequences exhibit the same function as (are functionally equivalent to) the reference sequence. For example, a variant or derivative of the inclusion body tag disclosed herein, which is based on the signal sequence ssTorA from the enzyme trimethylamine N-oxide reductase (TorA) of E. coli, varies from (or is derived from) the native ssTorA sequence by one or more amino acid substitutions, deletions and/or insertions, but retains the function of inducing inclusion body formation when fused or operatively linked to a POI.

The term "codon degeneracy" refers to the natural redundancy of the genetic code, wherein the genetic code permits variation of the nucleotide sequence without changing the amino acid sequence of the encoded polypeptide. A skilled person within the field of the invention is well aware of the codon bias exhibited by certain host cells, wherein certain nucleotide codons are more preferably used in certain host cells or organisms, to encode for a certain amino acid. When constructing an expression vector according to the invention it is therefore within the boundaries of the invention to adapt the codon usage in such an expression vector to the selected host cell.

The term "genetic construct" refers to an engineered combination of genetic elements, such as genes or other polypeptide coding elements, promoters, regulatory elements, transcription and termination regions etc, assembled into a single nucleic acid. A genetic construct may also comprise genetic elements encoding two or more portions from different polypeptides, such that the genetic construct encodes a fusion polypeptide comprising the two or more portions.

The expressions "recombinant polypeptide", "recombinant nucleic acid" and "recombinant genetic construct" refer to polypeptides or nucleic acids that result from the use of laboratory methods to bring together genetic material from multiple sources, creating nucleic acids and polypeptides encoded therefrom that would not otherwise be found in nature.

"Transcriptional unit" as used herein refers to a nucleic acid sequence that is normally transcribed into a contiguous RNA molecule. The transcriptional unit might contain one gene or coding sequence (monocistronic) or two (dicistronic) or more genes or coding sequences (polycistronic) that code for functionally related polypeptide molecules.

"Promoter", "promoter region" or "promoter sequence" as used herein refers to a nucleic acid sequence that initiates and/or regulates expression of a transcriptional unit. A promoter comprises a region capable of binding RNA polymerase and of initiating transcription of a downstream (3' direction) coding sequence. Within the promoter region there is also a transcription initiation site, as well as transcription factor binding sites and protein binding domains responsible for the binding of RNA polymerase such as the putative −35 region and the Pribnow box. The promoter may also, optionally, comprise regulatory elements involved in the regulation of timing and strength of the expression. A number of different promoters having various characteristics are known in the art. The promoters may for instance vary in their strength, i.e. their level of expression, in their kinetic properties, i.e. their transcriptional rate and in how fast the expression is turned on and off, and in the way that they control the expression, i.e. constitutive expression or induced expression, for example as a response to external stimuli.

"Translation initiation region" is a signal region which promotes translation initiation and which functions as the ribosome binding site such as the Shine Dalgarno sequence.

"Transcription termination region" refers to a sequence which causes RNA polymerase to terminate transcription. The transcription termination region is usually part of a transcriptional unit and increases the stability of the mRNA.

A "vector", "vector expressible in a host" or "expression vector" is a nucleic acid construct, generated recombinantly or synthetically, with a series of specified nucleic acid elements that permit transcription of a coding nucleic acid in a host cell. Typically, this vector includes a transcriptional unit, comprising a particular nucleic acid sequence to be transcribed, operably linked to a promoter. The vector may also comprise additional elements, such as selection markers and origins of replication. Inside a host cell the vector is an extrachromosomal element and often carries transcriptional units that encode polypeptides that are not part of the native cellular machinery. A vector is usually in the form of a circular, double stranded DNA molecule. A vector expressible in a host can be e.g., an autonomously or self-replicating plasmid, a cosmid, a phage, a virus or a retrovirus.

An "antibiotic resistance marker" or "selection marker", is a fragment of DNA that contains a gene whose product confers resistance to an antibiotic (e.g., chloropamphenicol, ampicillin, gentamycin, streptomycin, tetracyclin, kanamycin, neomycin) or the ability to grow on selective media (e.g., ura (uracil), leu (leucine), trp (tryptophan), his (histidine)). It is used in combination with host cells that are auxotrophic mutants, i.e. that cannot make the above mentioned molecules. A vector comprising a selection marker, i.e. a gene that can convert an auxotroph into a non-auxotroph, makes it possible for a cell comprising the vector to grow on medium lacking the molecule(s) it was not able to grow on before transformation (Amberg et al. (2005) Methods in Yeast Genetics. Cold Spring Harbor Laboratory Press). Usually, plasmids contain an antibiotic resistance marker to force the bacterial cell to maintain the plasmid.

The "origin of replication" (also called the replication origin) is a particular DNA sequence at which DNA replication is initiated. DNA replication may proceed from this point bidirectionally or unidirectionally.

The "copy number" of a vector, such as a plasmid, refers to the average number of a particular vector or plasmid per cell. The copy number is determined by the origin of replication.

The terms "host", "host cell" and "recombinant host cell" are used interchangeably herein to indicate a prokaryotic or eukaryotic cell into which one or more vectors or isolated and purified nucleic acid molecules of the invention have been or can be introduced. In a preferred embodiment, the host cell is a microbial host cell. In another preferred embodiment, the microbial host cell is a bacterial cell. It is understood that such terms refer not only to the particular subject cell but also to the progeny or potential progeny of such a cell. Because certain modifications may occur in succeeding generations due to either mutation or environmental influences, such progeny may not, in fact, be identical to the parent cell, but are still included within the scope of the term as used herein.

The terms "transformation", "transformed", "transfect", "transfected" or "introducing a nucleic acid into a host cell" denote any process wherein an extracellular nucleic acid like a vector, with or without accompanying material, enters a host cell. The term "cell transformed" or "transformed cell" means the cell or its progeny into which the extracellular nucleic acid has been introduced and thus harbors the extracellular nucleic acid. The nucleic acid might be introduced into the cell so that the nucleic acid is replicable either as a chromosomal integrant or as an extra chromosomal element.

Transformation of appropriate host cells with e.g., an expression vector can be accomplished by well-known methods such as microinjection, electroporation, particle bombardment or by chemical methods such as calcium phosphate-mediated transformation, described e.g., in Maniatis et al. 1982, Molecular Cloning, A laboratory Manual, Cold Spring Harbor Laboratory, or in Ausubel et al. 1994, Current protocols in molecular biology, John Wiley and Sons.

"Overexpression" and "production" are used interchangeably.

The term "level of expression" refers to the amount of mRNA or polypeptide that accumulates in the cell as a gene is expressed. By "strong expression" is meant that the expression results in high levels, or in other words a large amount, of mRNA or polypeptide accumulating in the cell. By "weak expression" is meant that the expression results in low levels, or a small amount, of mRNA or polypeptide accumulating in the cell.

By "rate of expression" is meant the kinetics of the expression, i.e. the amount of mRNA or polypeptide that accumulates in the cell per unit time as a gene is expressed. By "fast expression" is meant that high levels of mRNA or polypeptide accumulate in the cell in a short or relatively short time.

As is known in the art, the level and rate of expression of a polypeptide in a cell can be controlled in different ways, for example by selection of an appropriate promoter. A "strong promoter" yields high levels of mRNA or polypeptide from the transcriptional unit it controls, whereas a "weak promoter" yields lower levels of mRNA or polypeptide. A "fast promoter" gives fast expression. i.e. the levels of mRNA or polypeptide accumulate in a short or relatively short time.

DETAILED DESCRIPTION

The present invention relates generally to the use of an inclusion body tag, originally derived from the signal sequence (ssTorA) of the enzyme trimethylamine-N-oxide reductase (TorA, TOR or TMAO reductase), for the production of polypeptides of interest in inclusion bodies. The inventors have surprisingly found that the inclusion body tag disclosed herein functions as an efficient and universal tag sequence that can be used for the production of polypeptides of any kind (size, conformation, solubility etc.) in inclusion bodies. The inclusion body tag disclosed herein induces inclusion body formation when fused to any type of polypeptide, including the very soluble proteins thioredoxin (TrxA) and maltose-binding protein (MBP) that are normally used to prevent formation of inclusion body formation of other proteins. The present disclosure demonstrates the use of such a sequence as a powerful and universal inclusion body tag.

An ssTorA Derived Inclusion Body Tag

There are two main pathways for protein translocation and export in plant chloroplasts, bacteria, and archaea; the Sec pathway and the Twin-arginine-translocation (Tat) pathway. The majority of periplasmic and secreted proteins are targeted to the Sec pathway, which transports proteins across the thylakoid (chloroplasts) or cytoplasmic (bacteria and archaea) membrane in an unfolded state. The Tat pathway, on the other hand, enables translocation of already folded proteins across the cytoplasmic membrane in various organisms. The pathway comprises the Tat translocase, which is responsible for the translocation and is composed of two or three essential membrane proteins; TatA, TatB, and/or TatC, depending on organism. Substrates for the Tat translocase include enzymes that require cofactor insertion already in the cytoplasm, multimeric proteins that have to assemble in the cytoplasm, certain membrane proteins etc., i.e. proteins or polypeptides that require exportation across the cell membrane in a folded state.

Polypeptides that are targeted to the Tat pathway comprise a cleavable N-terminal signal sequence, a Tat signal sequence, that directs the protein to the Tat translocase and initiates the export (Oresnik, I. J. et al., Molecular Microbiology (2001) 40:323-331; Jack, R. L. et al., Biochem Soc Trans. (2005) 33:105-107). The Tat signal sequences are on average 38 amino acids long and have a tripartite structure; a positively charged N-terminal region (n-region), a hydrophobic core (h-region) and a polar C-terminal region (c-region). Signal sequences capable of targeting polypeptides to the Tat translocase comprise the consensus motif -S/T-R-R-X-F-L-K- (SEQ ID NO:51), where X is any polar amino acid. The twin-arginine dipeptide gave rise to the pathway's name. ssTorA is a Tat signal sequence originating from the N-terminal portion of the enzyme trimethylamine-N-oxide reductase (TorA). TorA is found in bacteria such as *E. coli, Salmonella typhimurium, Vibrio cholerae, Shewanella massilia, Vibrio vulnificus* and *Rhodobacter sphaeroides*. In its native context in these Gram-negative bacteria, ssTorA enables exportation of TorA from the cytoplasm across the inner membrane, to the periplasm, via the twin-arginine translocation (Tat) pathway (Lee, P. A. et al., Annu Rev Microbiol (2006) 60:373-395). Due to its ability to direct TorA to the Tat pathway and initiate the translocation of TorA across the inner membrane of Gram-negative bacteria and the cell membrane of Gram-positive bacteria, ssTorA has previously been explored as a fusion partner for periplasm- or growth medium-directed export of heterologous proteins that attain a folded conformation in the cytoplasm (Tinker, J. K. et al., Infect Immun. (2005) 73(6):3627-35; Kang, D. G. et al., J Biotechnol. (2005) 118(4):379-85; DeLisa, M. P. et al., Proc Natl Acad Sci USA. (2003) 100(10):6115-20; Kim, J. Y. et al., Appl Environ Microbiol. (2005) 71(12):8451-9; Barrett, C. M. et al., Biochem Biophys Res Commun. (2003) 304(2):279-84; DeLisa, M. P. et al., J Bacteriol. (2004) 186(2):366-73; Li, S. Y. et al., J Biotechnol. (2006) 122(4):412-21; Fisher, A. C. et al., Protein Sci. (2006) 15(3):449-58; Thomas, J. D. et al., Mol Microbiol. (2001) 39(1):47-53).

When testing ssTorA to mediate optimal targeting of recombinant proteins to the *E. coli* periplasm, the present inventors surprisingly found that it could be used to induce the formation of inclusion bodies. Based on this finding, and as demonstrated by the Examples, the inventors have further been able to define the core inclusion body forming sequence IBF, and to demonstrate use of many different variants thereof as a fusion partner to a polypeptide of interest, for production of the POI in inclusion bodies.

In one embodiment of the fusion polypeptide disclosed herein, the inclusion body tag is derived from the native ssTorA signal sequence. The inclusion body tag may for example be at least 60%, 65%, 70%, 75%, 80%, 85%, 90%, or 95%, or as much as 96%, 97%, 98%, or 99% identical to the native ssTorA signal sequence.

Fusion Polypeptides of the Invention Comprising the Inclusion Body Tag

The disclosed inclusion body tag can be fused to any polypeptide of interest for production of the POI in inclusion bodies. The POI may be of any length, function and solubility. In general, the present invention is advantageously used for POIs that are difficult to produce, due to being degraded in the host cell, due to being toxic to the host cell and/or due to being difficult to isolate and purify from the other proteins and/or cellular components of the host cell. Production of the POI is typically increased when it is expressed and aggregated in insoluble inclusion bodies, because i) the POI is protected from proteolytic degradation, ii) the host cell is protected from the toxicity of the POI and/or iii) inclusion bodies comprising the POI are easily separated from the other proteins and cellular components e.g. by centrifugation and/or filtration. In one embodiment, the POI is a POI that is produced at significantly higher levels when expressed in inclusion bodies compared to when expressed in soluble form.

In different embodiments, the POI, when not fused to the inclusion body tag, is very or appreciably soluble, soluble or partly soluble under normal physiological conditions. When the POI is fused to the inclusion body tag, the resulting fusion polypeptide of the invention is produced in insoluble inclusion bodies.

The inclusion body tag disclosed herein is useful for production of POIs of any length in inclusion bodies. In different embodiments, the POI may for example be between 10-5000 amino acids, 10-2000 amino acids or 10-1500 amino acids in length. Preferably the POI is between 10 and 1500 amino acids long.

In one embodiment, the POI has a molecular weight of between 1 and 500 kD. Typically, the POI has a molecular weight of less than 200 kD, such as less than 150 or 100 kD.

The POI can be a polypeptide that is heterologous or homologous to the host cell.

The POI may be a soluble or partly soluble cytoplasmic polypeptide, a soluble or partly soluble secretory polypeptide or a membrane polypeptide.

The function of the POI may vary. Examples include, but are not limited to: bioactive molecules such as curative agents for diseases (e.g. growth factors, hormones, interleukins, interferons and other polypeptides that target and affect cellular components such as receptors, channels and lipids), enzymes, toxins, structural polypeptides, research tools such as green fluorescent protein (GFP), antimicrobial polypeptides etc.

The fusion polypeptide may comprise more than one POI. Thus, the fusion polypeptide may comprise two, three or more POIs. Whenever referred to herein in singular form, the POI may also alternatively be present as two, three or more POIs.

As disclosed herein, the POI is fused to the inclusion body tag such that the tag and POI form a fusion polypeptide. This means that the POI is fused to the inclusion body tag such that they form one continuous polypeptide. The POI may be adjacent to the inclusion body tag. Alternatively, the fusion polypeptide may comprise an intermediate amino acid sequence between the POI and the inclusion body tag. Moreover, there is no limitation in the order of the POI relative to the inclusion body tag. Because design of the fusion polypeptide is carried out at the DNA level, care must be taken so that the reading frame of the POI is the same as the reading frame of the inclusion body tag.

In one embodiment, the fusion polypeptide comprises one or more POI(s) operably linked to at least one copy of the inclusion body tag. In another embodiment, the fusion polypeptide comprises one or more POI(s) operably linked to two, three or more copies of the inclusion body tag. Use of two, three or more copies of the inclusion body tag has the advantage of often yielding more efficient inclusion body formation. Whenever referred to herein in singular form, the inclusion body tag may also alternatively be present as two, three or more copies.

The inclusion body tag or tags may be fused to the N-terminal side or the C-terminal side of the POI. In one embodiment, one or more inclusion body tags are fused to both of the N-terminal side and the C-terminal side of the POI.

In one embodiment, the fusion polypeptide comprises a cleavable element, arranged or positioned between the POI and the inclusion body tag. The cleavable element enables separation of the POI from the inclusion body tag by a cleavage step. The use of cleavable elements is well known in the art and methods for cleaving include enzymatic cleavage and chemical hydrolysis. The cleavable element is for example a cleavable amino acid sequence that is recognized by a specific protease or is sensitive to a specific chemical. The cleavable amino acid sequence is generally between 1 and 50 amino acids long, depending on the protease or chemical to be used for cleavage. A number of cleavable elements are known in the art and may be used. Examples include the TEV recognition site, recognized by the TEV protease, the SUMO recognition site, recognized by the SUMO protease, inteine tags that are cleaved in the presence of thiols, and an acid cleavable aspartic acid-proline dipeptide (D-P) moiety, as well as cleavage elements recognized by factor Xa, thrombin, enterokinase and HRV 3C protease. The cleavable element may be incorporated into a fusion polypeptide of the invention comprising the inclusion body tag, by various recombinant techniques that are known in the art.

The POI may optionally also comprise additional portions of amino acid sequence for other functions, e.g. amino acid tags for use in purification or biochemical detection of the POI.

Expression Vectors

The fusion polypeptide is encoded by a nucleic acid, in the form of an expression vector, and expressed in a host cell. The nucleic acid can be constructed with the use of standard molecular biology techniques involving restriction enzymes, DNA ligases, PCR, oligonucleotide synthesis, DNA purification and other methods well-known to a person skilled in the art. A genetic construct is engineered comprising a transcriptional unit encoding the fusion polypeptide comprising the POI fused to the inclusion body tag. The transcriptional unit is arranged such that the reading frame of the portion encoding the POI matches the reading frame of the inclusion body tag. Optionally the transcriptional unit also comprises sequence encoding an intermediate amino acid sequence between the POI and the inclusion body tag and/or sequence encoding additional amino acid sequences providing other functionalities, e.g. tags for purification of the POI.

The transcriptional unit is arranged in an expression vector, in which it is operably linked to one or more promoters and/or other sequences controlling its expression. Typically, the vector comprises a region 5' of the transcriptional unit which harbors a promoter or transcription initiation region, and, optionally, a region 3' of the transcriptional unit which controls transcription termination. Such control regions preferably, although not necessarily, derive from genes that are native to the selected expression host cell.

Transcription initiation regions and promoters that are useful for driving expression of the fusion polypeptide from the transcriptional unit in different host cells are numerous and familiar to those skilled in the art. Suitable promoters depend on the host cell selected for expression. These include, but are not limited to, the tet, lac, tac, trc, ara (pBAD), trp, rha, lambda PL and T7 promoters for use in *E. coli*, the amy, apr and npr promoters for use in *Bacillus* and the CYC1, HIS3, GAL1, GAL10, ADH1, PGK, PHO5, GAPDH, ADC1, TRP1, URA3, LEU2, ENO and TPI promoters for use in *Saccharomyces*. Preferred promoters in *E. coli* include the tet, araBAD and lacUV5 promoters. Other promoters having similar kinetic properties are also preferred, both in *E. coli* and in other hosts. Such promoters enable strong and fast protein production and therefore contribute to efficient inclusion body production, as is described further below.

A transcription termination region may optionally be included in the vector for optimization of expression and/or increasing the stability of the transcribed mRNA. Such regions are also known in the art, or may be derived from various genes native to the preferred host.

Furthermore, the vector typically comprises other functions, such as one or more selection markers and a sequence allowing and controlling autonomous replication of the vector, e.g. an origin of replication (ori). The origin of replication determines the copy number of the vector. Preferably, the origin of replication is a high copy number origin of replication. Such origins of replication enable strong and fast protein production and therefore contribute to efficient inclusion body production, as will be described further below.

The vector is preferably an autonomously or self-replicating plasmid, a cosmid, a phage, a virus or a retrovirus. A wide variety of host/vector combinations may be employed in expressing the fusion polypeptides of this invention. Useful expression vectors, for example, may comprise of segments of chromosomal, non-chromosomal and/or synthetic nucleic acid sequences. Suitable vectors include vectors with a specific host range, such as vectors specific for e.g. *E. coli*, as well as vectors with a broad host range, such as vectors useful for Gram-negative or Gram-positive bacteria.

Preferred vectors are autonomously or self-replicating plasmids. More preferred are vectors with a specific host range, such as vectors specific for e.g. *E. coli*. Preferred vectors include pASK-IBA vectors comprising the tet promoter, such as pASK-IBA3 (IBA GmbH).

Other useful vectors for e.g. expression in *E. coli* are: pQE70, pQE60 und pQE-9 (QIAGEN, Inc.); pBluescript vectors, Phagescript vectors, pNH8A, [rho]NH16a, pNH18A, [rho]NH46A (Stratagene Cloning Systems, Inc.); ptrc99a, pKK223-3, [rho]KK233-3, pDR540, pRIT5 (Pharmacia Biotech, Inc.); pLG338, pACYC184, pBR322, pUC18, pUC19, pKC30, pRep4, pACYC177, pACYC184, pRSFIOIO and pBW22 (Wilms et al., 2001, Biotechnology and Bioengineering, 73 (2) 95-103) or derivatives thereof. Further useful plasmids are well known to the person skilled in the art and are described e.g. in "Cloning Vectors" (Eds. Pouwels P. H. et al. Elsevier, Amsterdam-New York-Oxford, 1985).

Expression Kinetics for Efficient Inclusion Body Formation

Vectors useful in the present disclosure are preferably arranged to facilitate a relatively high level of expression of the fusion polypeptide in a relatively short period of time. Fast and strong expression of the fusion polypeptide contributes to efficient inclusion body formation. The expression of the fusion polypeptide in the host cell at any time is determined not only by the level, i.e. strength, of expression, but also of the rate, i.e. kinetics, of the expression. For efficient inclusion body formation, it is preferred that the level of expression is high, i.e. that the expression is strong, and also that the rate of expression is high, i.e. that the expression is fast. A high level of expression at a fast rate can be achieved in various ways. For example, a strong promoter providing rapid expression kinetics can be selected for controlling the expression of the fusion polypeptide. An alternative way is to arrange the nucleic acid sequence encoding the fusion polypeptide in a vector of a high copy number, such that multiple copies of the nucleic acid encoding the fusion polypeptide will be present in the host cell. As expression is induced, the fusion polypeptide will be expressed in parallel from the multiple copies, ensuring a high level of expression at a fast rate. A combination of a strong, fast promoter and a vector of high copy number provides even more efficient expression in terms of level and speed.

In one embodiment, fast and strong expression of the fusion polypeptide of the present invention is achieved by arranging the transcriptional unit encoding the fusion polypeptide such that it is under control of a strong and fast promoter. The promoter is suitably selected to obtain the desired expression profile in combination with other factors influencing expression kinetics (e.g. plasmid copy number, see below). For example, where *E. coli* is used as host cell, a preferred promoter is the tetracyclin inducible promoter (tet promoter) (Skerra, A., Gene (1994), 151:131-135; Muthukrishnan, A-B et al., Nucleic Acids Res. (2012), 40:8472-8483). The tet promoter yields efficient production of fusion polypeptides comprising the inclusion body tag in inclusion bodies. The tet promoter is known to be a strong promoter with fast expression kinetics. The onset of expression is faster from the tet promoter than from many other known promoters in *E. coli*. The tet promoter thus yields higher levels of expressed protein in a shorter time, compared to many other promoters. It is believed that the fast and strong protein expression from the tet promoter contributes to efficient inclusion body formation, since the high levels of fusion polypeptide promote aggregation of the fusion polypeptide.

Strong and fast expression of the fusion polypeptide, and thus efficient inclusion body formation, may alternatively be achieved by other arrangements. For example, a promoter with similar expression kinetics as the tet promoter may be used.

Alternatively, strong and fast expression, facilitating IB formation, may be achieved by use of a vector or plasmid with a high copy number origin of replication. A high number of copies of the expression vector in the cell enables expression from a high number of transcriptional units in parallel at any one time, leading to a fast and strong expression of the fusion polypeptide. Thus, in one embodiment the expression vector used for expression of the fusion polypeptide of the invention comprises a high-copy number origin of replication (ori). Preferably, the ori enables production of at least 100 copies of the plasmid in the cell, such as at least 200, 300, 400 or 500 copies per cell. In one embodiment, the ori is pUC.

Host Cells

For protein expression and production of the fusion polypeptide of the invention, the vector comprising the transcriptional unit encoding the fusion polypeptide is transformed into a suitable host cell, using a suitable method known in the art. The host cell is preferably a cell which can be cultured and manipulated by methods well known to a person skilled in the art, which is able to express heterologous proteins and in which inclusion bodies may form upon overexpression of certain polypeptides. The host cell carrying the expression vector encoding the fusion polypeptide constitutes an expression system for production of the fusion polypeptide. The expression system may be inducible or non-inducible.

Preferred host cells for expression of the fusion polypeptide in inclusion bodies include microbial host cells such as bacteria, yeast and filamentous fungi. Examples of host cells that may be used include, but are not limited to, species of the bacterial genera *Escherichia, Salmonella, Bacillus, Pseudomonas, Erwinia, Agrobacterium, Lactococcus, Vibrio, Shigella, Burkholderia, Acinetobacter, Zymomonas, Erythrobacter, Chlorobium, Chromatium, Flavobacterium, Cytophaga, Rhodobacter, Rhodococcus, Streptomyces, Brevibacterium, Corynebacteria, Mycobacterium, Deinococcus, Pantoea, Sphingomonas, Methylomonas, Methylobacter, Methylococcus, Alcaligenes, Synechocystis, Synecoccus, Anabaena, Thiobacillus, Methanobacterium, Klebsiella, Myxococcus, Bordetella* and *Caulobacter*, and fungal or yeast genera such as *Aspergillus, Trichoderma, Saccharomyces, Pichia, Yarrowia, Candida* and *Hansenula*.

Preferred host cells include *Escherichia, Salmonella, Pseudomonas* and *Bacillus*. A highly preferred host cell is *Escherichia coli* (*E. coli*).

Expression of Fusion Polypeptide

In one aspect, the invention provides a method for expression of a polypeptide of interest in inclusion bodies, comprising the step of expressing a fusion polypeptide according to the invention in a host cell. The method comprises the step of culturing the host cell under conditions wherein the nucleic acid encoding the fusion polypeptide is translated to a multitude of fusion polypeptide molecules and the fusion polypeptide molecules aggregate in inclusion bodies.

The host cells are cultured in a culture medium that is suitable for the particular host cell. For example, the medium comprises a suitable carbon source. Furthermore, the medium is preferably optimized for protein expression. For example, the host cells may be cultured in conventional media known in the art, such as a complex medium like Luria-Bertani broth or "nutrient yeast broth medium", a glycerol containing medium as described by Kortz et al., 1995, J. Biotechnol. 39, 59-65, or a mineral salt medium as described by Kulla et al., 1983, Arch. Microbiol, 135, 1. The medium may be modified as appropriate, e.g. by adding further ingredients such as buffers, salts, vitamins or amino acids. An antibiotic which matches the antibiotic resistance marker of the expression vector is preferably added to the medium in order to ensure stable presence of the vector and thus stable protein expression.

If the host is *Escherichia coli*, Luria-Bertani broth (LB medium) is advantageously used. The cells are generally cultured at a temperature of 37° C. When the culture reaches early log phase (at an $OD_{660}$ of from approximately 0.3 to approximately 0.5), expression of target protein is suitably induced by the addition of an inducer to the culture medium, the inducer being adapted to the promoter of the expression vector used. In a preferred embodiment, the promoter is the tet promoter (tetracyclin inducible promoter) and the inducer is anhydrotetracyclin (ahtc), which may for example be added at a concentration of from about 0.01 to about 10 μg/ml, more specifically from about 0.1 to about 1 μg/ml, or approximately 0.2 μg/ml. In another embodiment, the promoter is the araBAD promoter and the inducer is arabinose, which may for example be used at around 0.2%. In another embodiment, the promoter is the lacUV5 promoter and the inducer is IPTG, which may for example be used at around 1 mM. The inducer induces expression of the fusion polypeptide comprising the POI and the inclusion body tag. Induction is generally performed at a temperature of about 30 to 45° C., often at a temperature of approx. 37° C. Induction at slightly higher temperatures, such as at approx. 42° C., is often preferred because it often results in more efficient inclusion body formation.

As to suitable systems for cell culture in the context of the present invention, continuous or discontinuous culture such as batch culture or fed batch culture may for example be used, in culture tubes, shake flasks or bacterial fermenters.

The expression of fusion polypeptide can be monitored by e.g. SDS-PAGE combined with Coomassie/silver staining, Western blotting or variants thereof including dot blotting.

Cell growth may also be monitored by following optical density at 660 nm over time. As the cell culture reaches a stage which is optimal for protein recovery, cells are harvested and the inclusion bodies containing fusion polypeptide recovered from the culture of host cells. In order to obtain a maximum yield of the expressed polypeptide, the cells are usually harvested as the cell culture reaches stationary phase. Typically, the cells are homogenized or lysed, for example by lysozyme treatment, sonication or French press, in order to release the insoluble inclusion bodies comprising the fusion polypeptides.

Recovery of Fusion Polypeptide and POI from Inclusion Bodies

Methods for isolating inclusion bodies from cell lysates are well known in the art and include centrifugation, filtration and combinations thereof (Burgess, R R, Methods Enzymol. (2009), 463:259-82; Nguyen, L, Protein Expr. Purif. (1993), 4:425-433; Palmer and Wingfield, Curr Protoc Protein Sci (2012), Chapter 6: UNIT 6.3; Batas, B et al., J Biotechnol. (1999), 68(2-3):149-58). Typically, the process involves several cycles of homogenization, centrifugation/filtration and washing. pH adjustment may also be necessary at different steps of the procedure, for optimal yield of the fusion protein.

After isolation and washing of the inclusion bodies, the inclusion bodies/fusion polypeptides may be directly subjected to cleavage in order to separate the POI from the inclusion body tag.

Alternatively, isolated and washed inclusion bodies may be dissolved in a suitable solvent, such as urea, GuHCl (Guanidinium chloride), SDS or sarkosyl prior to cleavage.

As has been described, cleavage is performed by use of a cleavage agent, such as an enzyme or a specific chemical. The cleavage agent used is chosen so as to correspond to a cleavage element arranged in the fusion polypeptide, as has been described above. The cleavage agent recognizes the cleavage element and cleaves the fusion polypeptide between the POI and the inclusion body tag. Examples of cleavage agents that are useful in connection with the present invention include TEV protease, SUMO protease and thrombin, as well as chemical cleavage reagents such as an acid, cyanogens bromide or hydroxylamine. Many other cleavage agents are known in the art and may be used in connection with the present invention.

Furthermore, the cleavage step may be omitted, for example where the inclusion body tag does not interfere with the function or activity of the POI.

The fusion polypeptides or POIs obtained can be further purified by standard protein purification procedures known in the art. These may include differential precipitation, molecular sieve chromatography, ion-exchange chromatography, isoelectric focusing, gel electrophoresis, affinity, and immunoaffinity chromatography. These well-known and routinely practiced methods are described in e.g. Ausubel et al., supra., and Wu et al. (eds.), Academic Press Inc., NY; Immunochemical Methods in Cell and Molecular Biology.

EXAMPLES

Host Cell Strains

*E. coli* strain MC4100 has been described previously (Casadaban and Cohen 1980 J Mol Biol 138: 179-207). Strain TOP10F' was obtained from Life Technologies. Strain BL21(DE3) was purchased from EMD Millipore. Strain HDB97 has been described previously (Bernstein & Hyndman 2001 J Bacteriol 183: 2187-2197).

Plasmids

Figure 1:
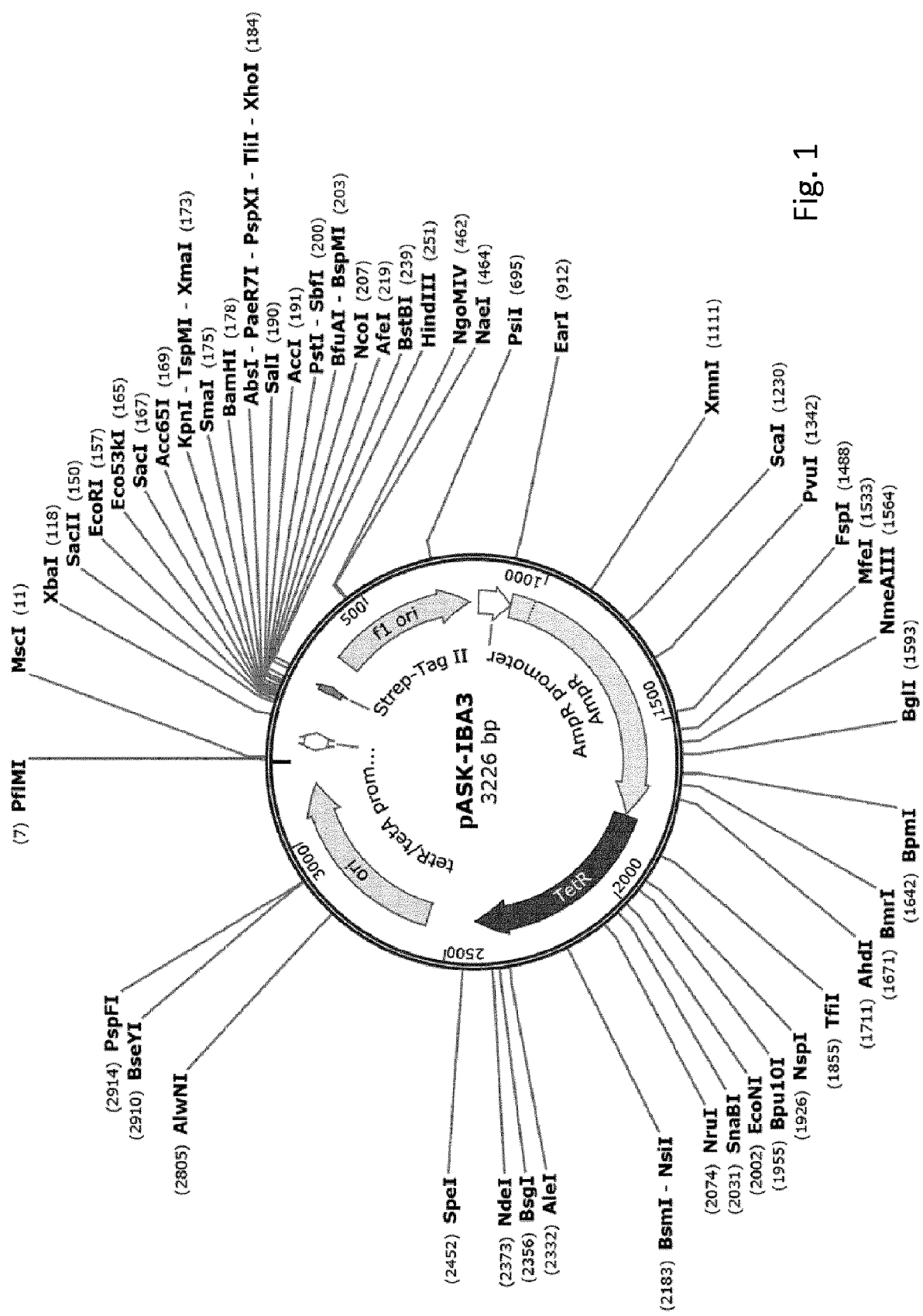
FIG. 1. Schematic illustration of expression vector pASK-IBA3 ("pIBA") comprising a tet promoter, as used in the expression of constructs in Examples 1-14, 16-17 and 19-25.

In Examples 1-14, 16-17 and 19-25, constructs were expressed from the expression vector pASK-IBA3 (IBA GmbH), schematically depicted in FIG. 1. In this high copy number vector, constructs were under the control of the strong and tightly controlled anhydrotetracycline-inducible TetA/TetR promoter.

Figure 2:
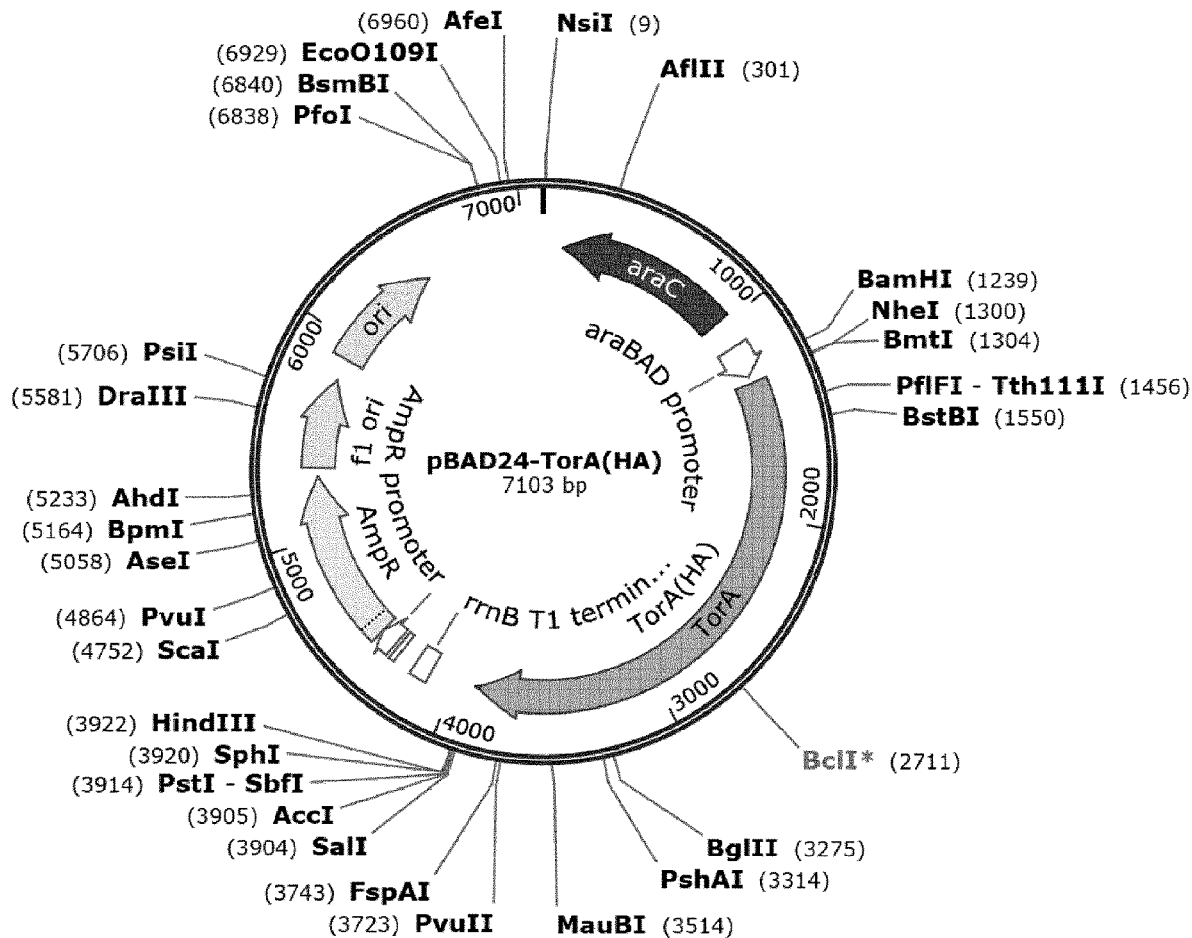
FIG. 2. Schematic illustration of expression vector pBAD24 comprising an araBAD promoter, as used in the expression of TorA(HA) in Example 15.

In Example 15, the construct was expressed from the high-copy number expression vector pBAD24 (Guzman et al. 1995 J Bacteriol 177: 4121-4130), schematically depicted in FIG. 2. In the pBAD24 vector, constructs were under the control of the arabinose-inducible araBAD promoter.

Figure 3:
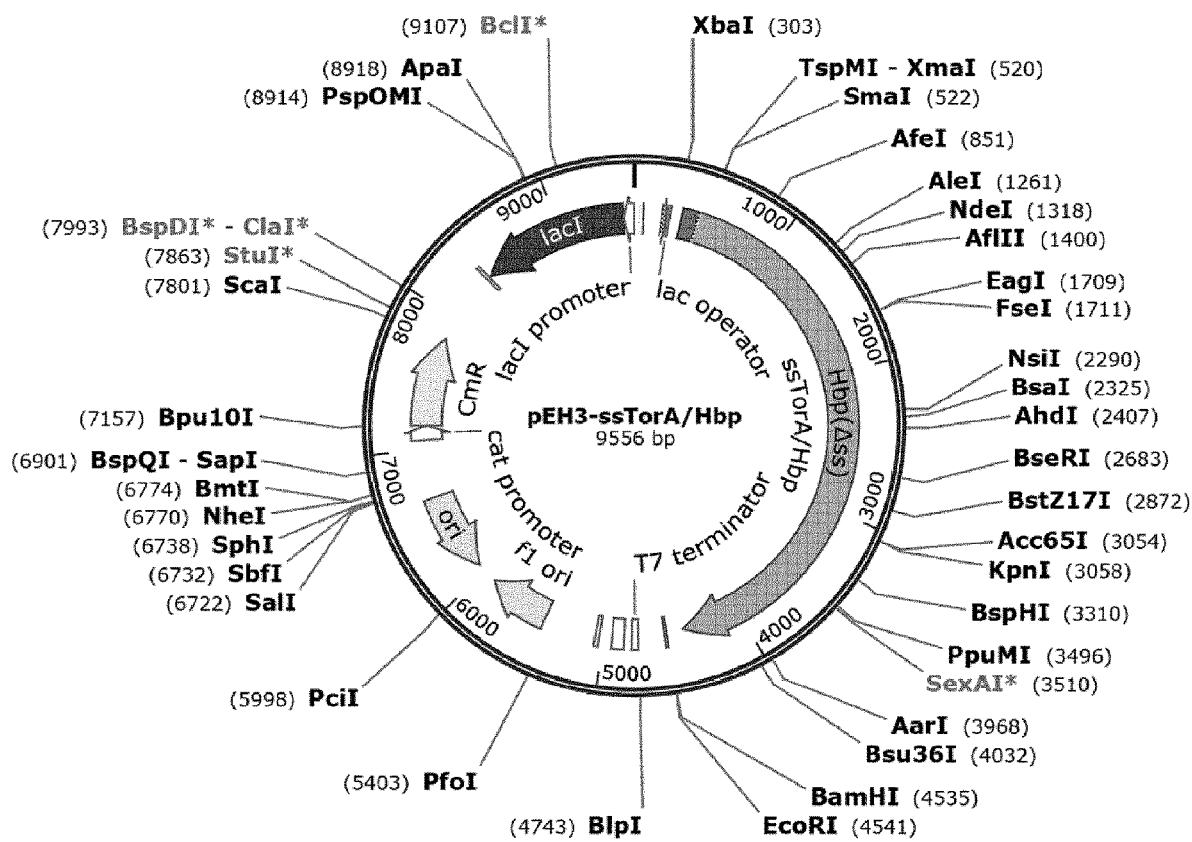
FIG. 3. Schematic illustration of expression vector pEH3 comprising a lacUV5 promoter, as used in the expression of ssTorA/Hbp in Example 18.
Figure 4:
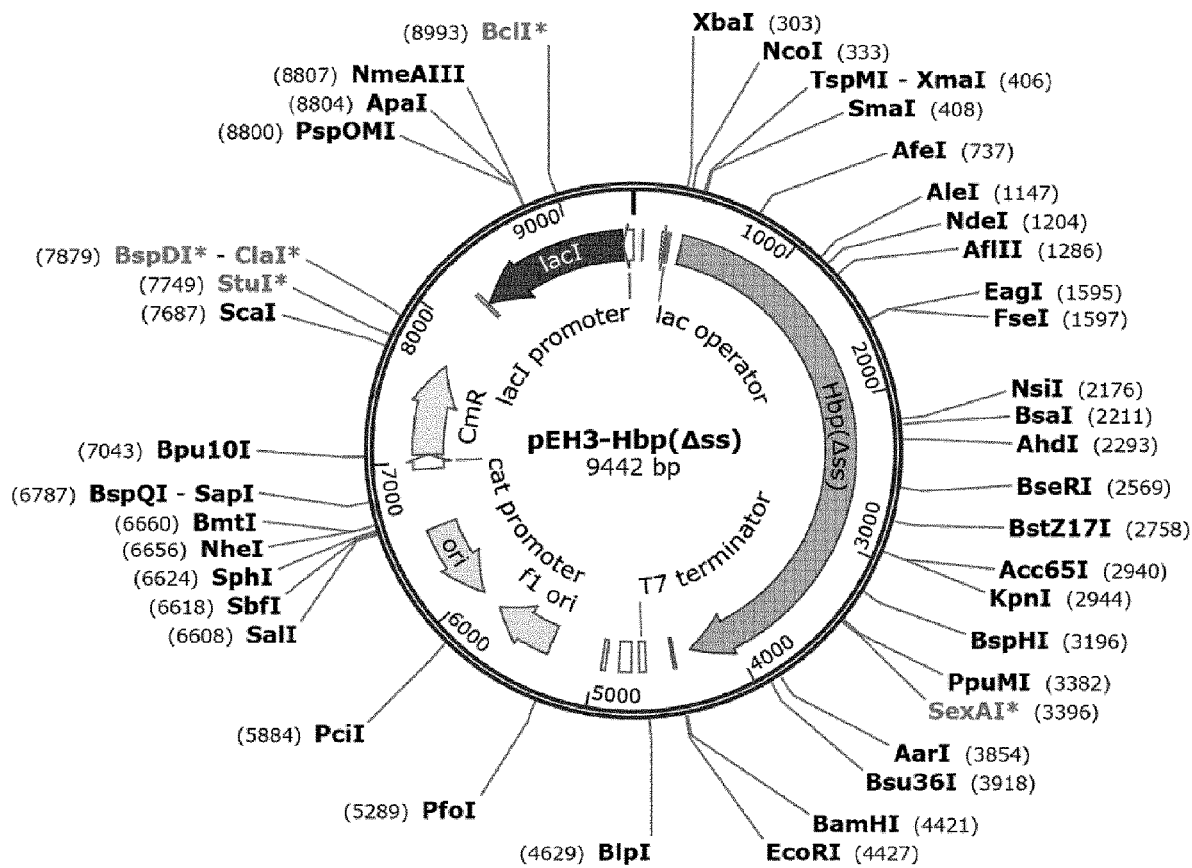
FIG. 4. Schematic illustration of expression vector pEH3 comprising a lacUV5 promoter, as used in the expression of Hbp(Δss) in Example 18.

In Example 18, constructs were expressed from the medium-copy number expression vector pEH3 (Hashemzadeh-Bonehi 1998 Mol Microbiol 30: 676-678). The vector expressing the ssTorA/Hbp fusion is schematically depicted in FIG. 3, and the vector expressing Hbp(Δss) alone is schematically depicted in FIG. 4. In the pEH3 vector, the constructs were under the control of an isopropyl β-D-1-thiogalactopyranoside-inducible lacUV5 promoter.

General Procedures

SDS-PAGE was performed using 12% or 4-12% NuPAGE Bis-Tris gels (Invitrogen) with a MES-SDS running buffer. Alternatively, SDS-PAGE was performed using 10%, 4-15% or "any-kD" Biorad mini-Protean TGX gels, or standard 12%, 14% or 15% SDS-PAGE gels. Before SDS-PAGE, protein samples were dissolved in 2×SDS-PAGE sample buffer (126 mM TrisHcl pH 6.8, 4% w/v SDS, 20% glycerol, 0.02% w/v bromophenol blue, 82 mM DTT) or 1×SDS-PAGE sample buffer (63 mM TrisHCl pH 6.8, 2% w/v SDS, 10% glycerol, 0.01% w/v bromophenol blue, 41 mM DTT) and boiled for 5 min. Gels were stained with Coomassie Brilliant Blue G-250 and captured using a Molecular Imager GS-800 Calibrated Densitometer (Bio-Rad).

Inclusion body fractionation was performed by taking two samples from the cell culture two hours (unless stated otherwise) after induction of protein expression. Cells of the first sample were used as a whole cell sample and stored on ice. Cells of the second sample were re-suspended in ice cold lysis buffer (100 mM NaCl, 1 mM EDTA, 50 mM Tris-HCL pH 7.6) after which lysozyme (17 ng/ml) was added. After 15 min incubation on ice, the suspensions were subjected to snap freezing and sonification (Branson Sonifier 250) to disrupt the cells. Subsequently, the cell lysates were subjected to centrifugation (4,500 g, 10 min) to pellet the inclusion bodies. The resulting supernatant, containing soluble proteins, was TCA precipitated. Corresponding amounts of whole cell sample (WC), insoluble material including inclusion bodies (IB) and soluble proteins (S) were analyzed by SDS-PAGE and Coomassie blue staining.

Example 1

Expression of hEGF and IL-3 Upon Fusion to Various Signal Sequences

This example illustrates high-level expression of a fusion polypeptide comprising an N-terminal signal sequence (ss) from TorA (ssTorA; SEQ ID NO:3) and the heterologous human epidermal growth factor (hEGF) in *E. coli* cells upon expression from vector pASK-IBA3 under control of the anhydrotetracycline (ahtc) inducible tetA promoter. The signal sequence is not processed, suggesting the fusion polypeptide is not translocated across the inner membrane into the periplasm but accumulates in the cytoplasm. By comparison, hEGF fusion polypeptides comprising any one of the signal sequences from PhoE, Hbp or DsbA are expressed at greatly reduced levels. Furthermore, a sub-population of these fusion polypeptides is processed, most likely by signal peptidase 1, suggesting translocation into the periplasm. Similar results are obtained using fusions of various signal sequences to the heterologous protein interleukin-3 (IL-3).

*E. coli* MC4100 cells carrying any one of the plasmids pIBA-ssTorA/hEGF, pIBA-ssPhoE/hEGF, pIBA-ssHbp/hEGF, pIBA-ssDsbA/hEGF, pIBA-ssTorAIIL-3, pIBA-ssPhoE/IL-3, pIBA-ssHbp/IL-3 and pIBA-ssDsbAIIL-3 were cultured in LB medium containing ampicillin at 37° C. When cultures reached early log-phase ($OD_{660} \approx 0.4$), protein synthesis was induced by addition of anhydrotetracyclin (ahtc; 0.2 µg/ml). Samples were withdrawn from the cultures at the time point of induction (− ahtc) and 2 hours after induction (+ ahtc). Of these samples, the cells were collected by low-speed centrifugation and analyzed by SDS-PAGE and Coomassie blue staining. FIG. 5 shows the results for A) the hEGF fusion polypeptides and B) the IL-3 fusion polypeptides.

Example 2

Inclusion Body Formation of hEGF and IL-3 Upon N-Terminal Fusion to the Signal Sequence of TorA This example demonstrates the expression of the fusion polypeptides ssTorA/hEGF and ssTorAIIL-3 in inclusion bodies in *E. coli*, using phase contrast microscopy. The formation of IBs is shown by the appearance of white spherical entities in cells induced for protein expression with anhydrotetracycline (+ ahtc) as opposed to non-induced cells (− ahtc).

*E. coli* MC4100 cells carrying either one of the plasmids pIBA-ssTorA/hEGF and pIBA-ssTorAIIL-3 were cultured in LB medium containing ampicillin at 37° C. When cultures reached early log-phase ($OD_{660} \approx 0.3$), they were split. One half was induced for protein synthesis by addition of anhydrotetracyclin (0.2 µg/ml; + ahtc), whereas the other half was left uninduced (− ahtc). Cells of each culture were collected 2 hours after induction and fixed with formaldehyde (2.8%) and glutaraldehyde (0.04%) in PBS (pH 7.2). After washing, cells were resuspended in PBS and immobilized on 1% agarose in water slab-coated object glasses. Microscopy was carried out using an Olympus BX-60 fluorescence microscope in the phase contrast mode with an UPLANFI 100×/1.3 oil objective. Images were captured using a Photometrics CoolSnap-fx CCD camera mounted in combination with Object-image 2.13 software. White spherical inclusion bodies (IB) of ssTorA/hEGF and ssTorA/IL-3 are shown in FIG. 6A and FIG. 6B, respectively.

Example 3

Inclusion Body Formation of Maltose Binding Protein and Thioredoxin a Upon N-Terminal Fusion to ssTorA Thioredoxin A (TrxA) and maltose binding protein (MBP) are well-soluble native proteins of *E. coli*, and are both being exploited as solubility tags to enhance the soluble expression of fused target proteins (Waugh 2005 Trends Biotechnol 23(6): 316-320). This example illustrates efficient expression of TrxA and MBP proteins in insoluble inclusion bodies upon N-terminal fusion to ssTorA (SEQ ID NO:3). TrxA and MBP remain soluble when not fused to ssTorA. Furthermore, the example shows enhanced expression of TrxA and MBP in inclusion bodies upon fusion to repeats of ssTorA (doublets denoted 2×; triplets denoted 3×). Inclusion body formation was assayed using the fractionation technique described in the section General procedures above, in which *E. coli* cell lysates are subjected to low-speed centrifugation to separate the non-soluble from the soluble material. The resulting pellet contained the inclusion bodies (IB), whereas the supernatant contains the soluble proteins (S). To analyze their protein content, both fractions are analyzed by SDS-PAGE and Coomassie staining, in parallel with a whole cell sample (WC).

*E. coli* TOP10F' cells carrying any one of the plasmids pIBA-TrxA, pIBA-ssTorA/TrxA, pIBA-ssTorA(2×)/TrxA, pIBA-MBP, pIBA-ssTorA/MBP, pIBA-ssTorA(2×)/MBP and pIBA-ssTorA(3×)/MBP were cultured in LB medium containing ampicillin at 37° C. When cells reached early log-phase ($OD_{660} \approx 0.4$), cells were induced for protein synthesis by addition of anhydrotetracyclin (0.2 µg/ml). After 2 hours, two samples were taken from each culture and subjected to inclusion body fractionation as described above. Results are shown in FIG. 7A (TrxA fused to one or two repeats of ssTorA) and FIG. 7B (MBP fused to one, two or three repeats of ssTorA).

Example 4

Inclusion Body Formation of Thioredoxin a Upon N-Terminal Fusion to ssTorA

This example illustrates the expression of TrxA upon N-terminal fusion to ssTorA in *E. coli* using phase contrast microscopy. The formation of IBs is shown by the appearance of white spherical entities in cells expressing the fusion polypeptide ssTorA/TrxA (FIG. 8C). In contrast, no IBs are visible in cells carrying an empty vector (FIG. 8A) or expressing TrxA without ssTorA (FIG. 8B).

*E. coli* TOP10F' cells carrying pASK-IBA3 (empty vector), pIBA-TrxA or pIBA-ssTorA/TrxA were cultured in LB medium containing ampicillin at 37° C. When cultures reached early log-phase ($OD_{660} \approx 0.3$), cells were induced for protein synthesis by addition of anhydrotetracyclin (0.2 µg/ml). Cells of each culture were collected 2 hours after induction and fixed with formaldehyde (2.8%) and glutaraldehyde (0.04%) in PBS (pH 7.2). After washing, cells were subjected to phase contrast microscopy as described in Example 2. The resulting images are shown in FIG. 8.

Example 5

Inclusion Body Formation in Various *E. coli* Strains

This example illustrates successful formation of IBs upon expression of an ssTorA fusion polypeptide in *E. coli* strains of different origin. Using the IB fractionation procedure described in General procedures above, successful IB formation of ssTorA/MBP was demonstrated in *E. coli* K-12 strain TOP10F' and *E. coli* B strain BL21(DE3). As a control, in both strains, MBP expressed without fused ssTorA remained soluble.

*E. coli* TOP10F' and BL21(DE3) cells carrying either pIBA-MBP or pIBA-ssTorA/MBP were cultured in LB medium containing ampicillin at 37° C. When cells reached early log-phase ($OD_{660} \approx 0.4$), cells were induced for protein synthesis by addition of anhydrotetracyclin (0.2 µg/ml). After 2 hours, two samples were taken from each culture and subjected to inclusion body fractionation as described above. Results are shown in FIG. 9A (MBP without ssTorA) and 9B (MBP fused to ssTorA).

Example 6

Role of Twin-Arginine Motif in IB Formation

This example illustrates that the twin-arginine motif of ssTorA is not critical for ssTorA-mediated IB formation of target proteins. Using the IB fractionation procedure described in General procedures above, it was shown that IB formation of ssTorA/TrxA was sustained upon conservative replacement of the twin-arginine pair of ssTorA by a twin-lysine pair (RR/KK; resulting in an inclusion body tag with the sequence SEQ ID NO:4). Furthermore, even upon non-conservative replacement of the twin-arginine pair by a twin-alanine pair (RR/AA; SEQ ID NO:5), IB formation was sustained.

Figure 10A:
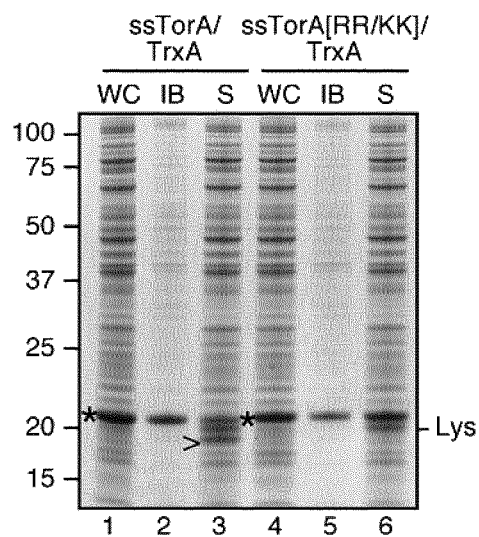
Figure 10B:
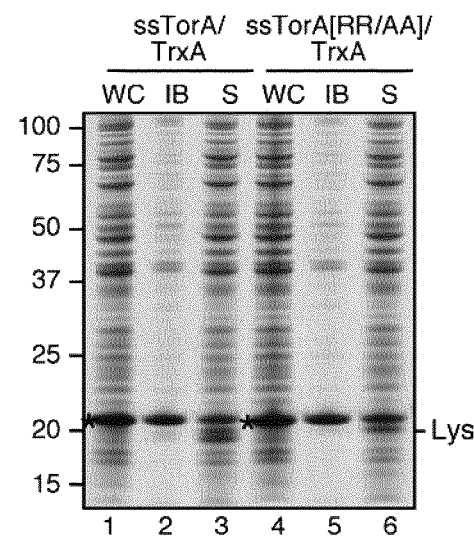

E. coli TOP10F' cells carrying any one of plasmids pIBA-ssTorA/TrxA, pIBA-ssTorA(RR/KK)/TrxA and pIBA-ssTorA(RR/AA)/TrxA were cultured in LB medium containing ampicillin at 37° C. When cells reached early log-phase ($OD_{660} \approx 0.4$), cells were induced for protein synthesis by addition of anhydrotetracyclin (0.2 µg/ml). After 2 hours, two samples were taken from each culture and subjected to inclusion body fractionation as described above. The results are shown in FIG. 10A for the RR/KK mutant and in FIG. 10B for the RR/AA mutant. The example demonstrates that positions R11 and R12 in the ssTorA sequence (SEQ ID NO:3) may be conservatively or non-conservatively mutated without loss of IB formation effect.

Example 7

The Triple Asn Motif of ssTorA is not Important for IB Formation

This example illustrates that the triple Asn motif at the N-terminus of ssTorA (SEQ ID NO:3) is not critical for ssTorA-mediated IB formation of target proteins. Using the IB fractionation procedure described in General procedures above, it was shown that IB formation of ssTorA/TrxA was sustained upon replacement of N3 of the ssTorA moiety by either an A (NNN/NAN; SEQ ID NO:6) or a K (NNN/NKN; SEQ ID NO:7) residue. Likewise, replacement of N4 by an A residue (NNN/NNA; SEQ ID NO:8) did not significantly affect IB formation compared to ssTorA/TrxA carrying a ssTorA (WT) signal sequence. Moreover, complete replacement of the triple Asn motif by a KTK sequence (NNN/KTK; SEQ ID NO:9), did not significantly reduce the efficiency of IB formation of ssTorA/TrxA.

E. coli TOP10F' cells carrying any one of plasmids pIBA-ssTorA/TrxA, pIBA-ssTorA(NNN/NAN)/TrxA, pIBA-ssTorA(NNN/NKN)/TrxA, pIBA-ssTorA(NNN/NNA)/TrxA and or pIBA-ssTorA(NNN/KTK)/TrxA were cultured in LB medium containing ampicillin at 37° C. When cells reached early log-phase ($OD_{660} \approx 0.4$), cells were induced for protein synthesis by addition of anhydrotetracyclin (0.2 µg/ml). After 2 hours, two samples were taken from each culture and subjected to inclusion body fractionation as described above. Results are presented in FIG. 11. The example demonstrates that the sequence NNN at positions 2-4 in the ssTorA sequence (SEQ ID NO:3), may be mutated without loss of IB formation effect.

Example 8

The Role the of N- and C-Terminal Parts of ssTorA in IB Formation

Part A of this example illustrates that the C-terminal moiety of ssTorA (positions 14-36 of SEQ ID NO:3) is needed for IB formation. Using the IB fractionation procedure described in General procedures above, it was shown that IB formation of ssTorA/TrxA was abolished upon deletion of residues 14-36 of ssTorA (yielding ssTorA(N')/TrxA, wherein the fusion tag ssTorA(N') has the sequence SEQ ID NO:10). Also, despite lowered expression and IB formation when compared to ssTorA/TrxA (WT), it is illustrated that the N-terminal moiety of ssTorA (positions 2-13 of SEQ ID NO:3) is not critical for IB formation, since significant levels of ssTorA/TrxA IB material were observed upon deletion of residues 2-13 of ssTorA (yielding ssTorA(C')/TrxA, wherein the fusion tag ssTorA(C') has the sequence SEQ ID NO:11).

Part B of this example illustrates enhanced expression and IB formation of ssTorA(C')/TrxA upon insertion of either an NNN sequence (C'+NNN; SEQ ID NO:12) or a KTK sequence (C'+KTK; SEQ ID NO:13) between ssTorA(C') (SEQ ID NO:11) and the initiator M residue.

E. coli TOP10F' cells carrying any one of pIBA-ssTorA/TrxA (WT), pIBA-ssTorA(N')/TrxA, pIBA-ssTorA(C')/TrxA, pIBA-ssTorA(C'+NNN)/TrxA and pIBA-ssTorA(C'+KTK)/TrxA were cultured in LB medium containing ampicillin at 37° C. When cells reached early log-phase ($OD_{660} \approx 0.4$), cells were induced for protein synthesis by addition of anhydrotetracyclin (0.2 µg/ml). After 2 hours, two samples were taken from each culture and subjected to inclusion body fractionation as described above. Resulting SDS-PAGE gels are shown in FIG. 12.

Example 9

N' to C' Progressive Deletion Analysis of ssTorA

This example illustrates that residues 5-9 of ssTorA are not necessary for IB formation. Using the IB fractionation procedure described in General procedures above, significant IB formation of ssTorA/TrxA was still observed upon deletion of residues 5-9 (Δ5-9; SEQ ID NO:14), although not to the same extent as ssTorA/TrxA carrying a ssTorA (WT; SEQ ID NO:3). The presence of residues 10-39 appears important for proper IB formation, IB expression, or both. This follows from the observation that deletion of residues 5-24 of ssTorA (exemplified by fusion tags Δ5-14 (SEQ ID NO:15), Δ5-19 (SEQ ID NO:16) and Δ5-24 (SEQ ID NO:17)) severely affects the expression of ssTorA/TrxA compared to ssTorA. Further truncation up to residue 39 (exemplified by fusion tags Δ5-29 (SEQ ID NO:18), Δ5-34 (SEQ ID NO:19) and Δ5-39 (SEQ ID NO:20)) restores expression, but ssTorA/TrxA is recovered exclusively from the soluble protein fraction, similar to TrxA without ssTorA (FIG. 13, lanes 25-27).

E. coli TOP10F' cells carrying pIBA-ssTorA/TrxA (WT), pIBA-ssTorA (Δ5-9)/TrxA, pIBA-ssTorA (Δ5-14)/TrxA, pIBA-ssTorA (Δ5-19)/TrxA, pIBA-ssTorA (Δ5-24)/TrxA, pIBA-ssTorA (Δ5-29)/TrxA, pIBA-ssTorA (Δ5-34)/TrxA, pIBA-ssTorA (Δ5-39)/TrxA or pIBA-TrxA were cultured in LB medium containing ampicillin at 37° C. When cells reached early log-phase ($OD_{660} \approx 0.4$), cells were induced for protein synthesis by addition of anhydrotetracyclin (0.2 µg/ml). After 2 hours, two samples were taken from each culture and subjected to inclusion body fractionation as described above. Resulting SDS-PAGE gels are shown in FIG. 13.

Example 10

C' to N' Progressive Deletion Analysis of ssTorA

This example illustrates that residues 29-36 of ssTorA are dispensable for IB formation. Using the IB fractionation procedure described in General procedures above, significant IB formation of ssTorA/TrxA was still observed upon deletion of residues 29-36 (exemplified by inclusion body tags Δ33-36 (SEQ ID NO:21) and Δ29-36 (SEQ ID NO:22)), similar to ssTorA/TrxA carrying a ssTorA. On the other hand, residues 17-28 are important for IB formation since deletion of these residues (exemplified by fusion tags Δ25-36 (SEQ ID NO:23), Δ21-36 (SEQ ID NO:24) and Δ17-36 (SEQ ID NO:25)) results in expression of ssTorA/TrxA virtually exclusively in the soluble protein fraction, similar to TrxA without ssTorA (FIG. 14, lanes 19-21).

*E. coli* TOP10F' cells carrying pIBA-ssTorA/TrxA (WT), pIBA-ssTorA(Δ33-36)/TrxA, pIBA-ssTorA (Δ29-36)/TrxA, pIBA-ssTorA (Δ25-36)/TrxA, pIBA-ssTorA (Δ21-36)/TrxA, pIBA-ssTorA (Δ17-36)/TrxA or pIBA-TrxA were cultured in LB medium containing ampicillin at 37° C. When cells reached early log-phase ($OD_{660}$≈0.4), cells were induced for protein synthesis by addition of anhydrotetracyclin (0.2 μg/ml). After 2 hours, two samples were taken from each culture and subjected to inclusion body fractionation as described above. Resulting SDS-PAGE gels are shown in FIG. 14.

Example 11

Combined N' and C' Deletion Analysis of ssTorA

This example illustrates that a tag comprising residues 1-4+10-28 of ssTorA is sufficient to express ssTorA/TrxA in inclusion bodies. This followed from an IB fractionation procedure as described in General procedures above, showing significant IB formation of ssTorA/TrxA upon combined deletion of residues 5-9 and 29-36 from the ssTorA sequence (inclusion body tag Δ5-9/Δ29-36 (SEQ ID NO:26)).

*E. coli* TOP10F' cells carrying pIBA-ssTorA/TrxA (WT), pIBA-ssTorA (Δ5-9)/TrxA, pIBA-ssTorA (Δ29-36)/TrxA, pIBA-ssTorA (Δ5-9/Δ29-36)/TrxA or pIBA-TrxA were cultured in LB medium containing ampicillin at 37° C. When cells reached early log-phase ($OD_{660}$≈0.4), cells were induced for protein synthesis by addition of anhydrotetracyclin (0.2 μg/ml). After 2 hours, two samples were taken from each culture and subjected to inclusion body fractionation as described above. A resulting SDS-PAGE gel is shown in FIG. 15.

Example 12

Inclusion Body Formation Upon C-Terminal Fusion of ssTorA and of Tandem Repeats of ssTorA This example illustrates successful expression of TrxA in IBs upon C-terminal fusion to ssTorA. Furthermore, the example shows enhanced expression of TrxA in inclusion bodies upon fusion to repeats of the ssTorA inclusion body tag (SEQ ID NO:3) (doublets: 2×; triplets: 3×) at the C-terminus. The efficiency of IB formation using C-terminally fused ssTorA is similar to using N-terminally fused ssTorA. Inclusion body formation was assayed using an IB fractionation procedure.

*E. coli* TOP10F' cells carrying pIBA-ssTorA/TrxA, pIBA-ssTorA (3×)/TrxA, pIBA-TrxA/ssTorA, pIBA-TrxA/ssTorA (2×), pIBA-TrxA/ssTorA (3×) or pIBA-TrxA were cultured in LB medium containing ampicillin at 37° C. When cells reached early log-phase ($OD_{660}$≈0.4), cells were induced for protein synthesis by addition of anhydrotetracyclin (0.2 μg/ml). After 2 hours, two samples were taken from each culture and subjected to inclusion body fractionation as described above. Resulting SDS-PAGE gels are shown in FIG. 16.

Example 13

Inclusion Body Formation of Chloramphenicol Acetyltransferase Upon Fusion to ssTorA This example illustrates very efficient IB formation of the *E. coli* enzyme chloramphenicol acetyltransferase (CAT) upon N-terminal fusion of ssTorA using an IB fractionation procedure. As a control, upon fusion of only the N-terminal part of ssTorA (N') (see Example 8), the vast majority of CAT remains soluble.

*E. coli* TOP10F' cells carrying pIBA-ssTorA/CAT or pIBA-ssTorA(N')/CAT were cultured in LB medium containing ampicillin at 37° C. When cells reached early log-phase ($OD_{660}$≈0.4), cells were induced for protein synthesis by addition of anhydrotetracyclin (0.2 μg/ml). After 2 hours, two samples were taken from each culture and subjected to inclusion body fractionation as described above. A resulting SDS-PAGE gel is shown in FIG. 17.

Example 14

Influence of A16P and F14Y Substitutions in ssTorA on IB Formation in the Context of ssTorA/CAT This example illustrates that substitution of the alanine residue at position 16 of ssTorA by a proline residue (A16P; SEQ ID NO:27) impairs IB formation in the context of an ssTorA/CAT fusion polypeptide. IB fractionation showed that the A16P substitution yields a largely soluble ssTorA/CAT fusion polypeptide, similar to ssTorA(N')/CAT (see Example 13). In contrast, substitution of the phenylalanine residue at position 14 of ssTorA by a tyrosine residue (F14Y; SEQ ID NO:28) does not affect IB formation. With the F14Y substitution, ssTorA/CAT is efficiently produced in IBs similar to ssTorA/CAT carrying a ssTorA sequence (WT).

*E. coli* TOP10F' cells carrying pIBA-ssTorA/CAT, pIBA-ssTorA(N')/CAT, pIBA-ssTorA(A16P)/CAT or pIBA-ssTorA(F14Y)/CAT were cultured in LB medium containing ampicillin at 37° C. When cells reached early log-phase ($OD_{660}$≈0.4), cells were induced for protein synthesis by addition of anhydrotetracyclin (0.2 μg/ml). After 2 hours, two samples were taken from each culture and subjected to inclusion body fractionation as described above. A resulting SDS-PAGE gel is shown in FIG. 18.

Example 15

Expression of Full-Length TorA in Inclusion Bodies Under the Control of an Arabinose-Inducible Promoter The ssTorA sequence normally functions as a signal sequence that mediates translocation of TorA across the *E. coli* inner membrane into the periplasm (Weiner et al. 1998, Cell 93(1): 93-101). This example demonstrates that ssTorA (SEQ ID NO:44) mediates expression of full-length TorA carrying a C-terminal HA tag (TorA(HA)) in inclusion bodies when expressed from the vector pBAD24 under control of the arabinose-inducible araBAD promoter. This followed from an IB fractionation procedure showing that TorA(HA) was recovered exclusively from the IB fraction. Hence, the expression conditions applied seem to change ssTorA from a translocation tag into an insolubility tag. Also, this example illustrates that ssTorA functions as an IB formation tag when expressed under the control of the arabinose-inducible araBAD promoter.

*E. coli* TOP10F' cells carrying pBAD24-ssTorA(HA), encoding the full-length TorA protein carrying a small C-terminally fused HA detection tag (YPYDVPDYA; SEQ ID NO:52) were cultured in LB medium containing ampicillin at 37° C. When cells reached early log-phase ($OD_{660} \approx 0.34$), cells were induced for protein synthesis by addition of arabinose (0.2%). After 2 hours, two samples were taken from each culture and subjected to A) inclusion body fractionation as described above and B) phase-contrast microscopy. For microscopy analysis, cells were re-suspended in LB medium and photographed with an Olympus F-view II camera mounted on an Olympus BH-2 microscope through an DApo100UV PL 1.30 oil 160/0.17 objective. Resulting SDS-PAGE gel and phase-contrast micrograph are shown in FIG. 19.

Example 16

Enhanced Expression of an Unstable Protein Upon Fusion to ssTorA

This example illustrates that fusion to ssTorA is an effective strategy to enhance the expression levels of a protein that is unstable when expressed in *E. coli*. A fusion polypeptide comprising ssTorA and hEGF (ssTorA/hEGF) is very highly expressed in *E. coli* as shown by the appearance of a dense band upon analysis of whole-cell sample by SDS-PAGE and Coomassie staining. In contrast, when not fused to ssTorA, hEGF is hardly detected by SDS-PAGE analysis, indicating poor expression and, in turn, instability of the protein in *E. coli*.

*E. coli* HDB97 cells carrying either the plasmid pIBA-ssTorA/hEGF or pIBA-hEGF were cultured in LB medium containing ampicillin at 37° C. When cultures reached early log-phase ($OD_{660} \approx 0.3$), protein synthesis was induced by addition of anhydrotetracyclin (ahtc; 0.2 μg/ml). Samples were withdrawn from the cultures at the time point of induction (− ahtc) and 2 hours after induction (+ ahtc). Of these samples, the cells were collected by low-speed centrifugation and analyzed by SDS-PAGE and Coomassie blue staining. Resulting SDS-PAGE gels are shown in FIG. 20.

Example 17

Expression of a Toxic Protein Upon Fusion to ssTorA

This example shows that fusion to ssTorA is an effective strategy to produce proteins that are toxic to *E. coli* host cells in IBs. In turn, production in IBs is an effective strategy to reduce the adverse effects on *E. coli* cell growth normally associated with overexpression of such toxic proteins. SymE is an *E. coli* toxin that binds to ribosomes, and overexpression of the protein leads to cell growth inhibition (Kawano et al. 2007 Mol Microbiol 64(3): 734-758). Upon overexpression of SymE from vector pASK-IBA3 under control of the anhydrotetracycline inducible tetA promoter, *E. coli* cell growth was greatly affected, the culture reaching a maximum $OD_{660}$ value of only 0.8. In contrast, upon overexpression of a fusion polypeptide comprising ssTorA and SymE (ssTorA/SymE), cell growth was dramatically improved, the culture reaching an $OD_{660}$ of ~1.7. An IB fractionation procedure showed that ssTorA/SymE is expressed almost exclusively in IBs. On the other hand, SymE without ssTorA appeared to remain largely soluble, explaining the toxicity towards the host cells expressing this protein.

Figure 21B:
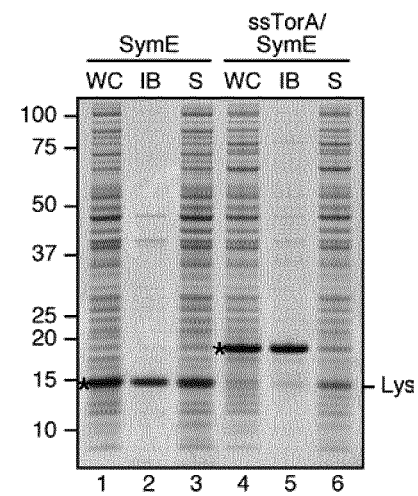

*E. coli* TOP10F' cells carrying either the plasmid pIBA-SymE or pIBA-ssTorA/SymE were cultured in LB medium containing ampicillin and glucose (0.4%) at 37° C. When cultures reached early log-phase ($OD_{660} \approx 0.3$), the cultures were shifted to 42° C. At this point, protein synthesis was induced by addition of anhydrotetracyclin (ahtc; 0.2 μg/ml), after which cell growth was continued. Cell growth was followed over time by measuring the optical density at 660 nm and plotted in the diagram shown in FIG. 21A. After 2 hours of expression, two samples were taken from each culture and subjected to inclusion body fractionation as described above. A resulting SDS-PAGE gel is shown in FIG. 21B.

Example 18

Expression of a Large, Unstable Hbp Derivative Protein into Inclusion Bodies Under the Control of an IPTG-Inducible Promoter Hbp is a large protein (1377 amino acid residues). An Hbp variant (1325 amino acid residues) lacking the 52 amino acid residue signal sequence [Hbp(Δss)] is unstable when expressed in *E. coli* due to proteolytic degradation by major cytoplasmic proteases such as Lon and ClpYQ (Sijbrandi et al. 2003 J Biol Chem 278(7):4654-9). This example shows that fusion to ssTorA is an effective strategy to enhance the expression levels of Hbp(Δss), which is unstable when expressed in *E. coli*. Furthermore, the example shows that ssTorA can provoke IB formation of proteins as large as 1325 amino acid residues. Moreover, this example shows that ssTorA (SEQ ID NO:44) is functional as an IB formation tag in the context of an IPTG-inducible lacUV5 promoter. SDS-PAGE analysis showed that ssTorA/Hbp was expressed at very high levels in *E. coli* cells from vector pEH3 under the control of an isopropyl β-D-1-thiogalactopyranoside-inducible lacUV5 promoter. In contrast, Hbp (Δss) expressed and analyzed under the same conditions was detected at very low levels. Furthermore, an IB fractionation procedure showed that ssTorA/Hbp was recovered exclusively from the IB fraction when expressed under these conditions.

*E. coli* TOP10F' cells carrying either pEH3-ssTorA/Hbp or Hbp(Δss) were cultured in LB medium containing chloramphenicol (30 μg/ml), tetracycline (6.25 μg/ml) and glucose (0.2%) at 37° C. When cells reached early log-phase ($OD_{660} \approx 0.3$), protein expression was induced by addition of isopropyl β-D-1-thiogalactopyranoside (1 mM). After 2 hours, two samples were taken from each culture and subjected to inclusion body fractionation as described above. ssTorA/Hbp (*) and a putative Hbp(Δss) expression product (>) are indicated in FIG. 22.

Example 19

Proteins of Various Origins and Sizes Produced in IBs by Fusion of ssTorA

A large number of proteins were successfully produced in IBs using N-terminal fusion to ssTorA (SEQ ID NO:3) or repeats thereof, and are listed in Table 4 below. This example illustrates the possibility to use ssTorA for IB formation of proteins of various sources (including eukaryotic and prokaryotic) and sizes, ranging from 53 (hEGF) to 1325 amino acid residues (Hbp). The example also shows successful IB formation of fusion proteins containing cleavage elements for separation of the inclusion body tag from a protein of interest, such as a TEV protease site and a thrombin cleavage site. By way of exception, the ssTorA and ssTorA(3×) sequences used with $His_6$-tagged GFP carried an S38R mutation compared to SEQ ID NO:3.

TABLE 4

Proteins produced in IBs using ssTorA and repeats thereof as inclusion body tag

| Origin | Protein | Accession | Amino acids | Remarks |
|---|---|---|---|---|
| E. coli | TorA | UniProtKB P33225 | 40-848 | Excluding signal sequence |
| | TrxA | UniProtKB P0AA25 | 2-129 | |
| | MBP | UniProtKB P0AEX9 | 27-396 | Excluding signal sequence |
| | TF | UniProtKB P0A850 | 2-432 | |
| | Hbp | UniProtKB P88093 | 53-1377 | Mature domain |
| | FtsL | UniProtKB P0AEN4 | 60-121 | Periplasmic domain |
| | FtsB | UniProtKB P0A6S5 | 24-103 | Periplasmic domain |
| | FtsQ | UniProtKB P06136 | 50-276 | Periplasmic domain |
| | FtsK | UniProtKB P46889 | 818-1329 | Cytoplasmic domain; Carrying N-terminal 6xHis tag |
| | SymE | UniProtKB P39394 | 2-113 | |
| | SurA | UniProtKB P0ABZ6 | 21-428 | Excluding signal sequence |
| | CAT | UniProtKB P62577 | 1-219 | |
| Mycobacterium marinum | EspG5 | UniProtKB B2HSU5 | 1-300 | Carrying C-terminal 6xHis tag |
| | EccCb1 | UniProtKB B2HMT4 | 1-591 | Carrying C-terminal 6xHis tag |
| | EccD1 | UniProtKB B2HNQ4 | 1-479 | Carrying C-terminal 6xHis tag |
| | EspE | UniProtKB B2HMS7 | 330-418 | C-terminal domain; Carrying C-terminal 6xHis tag |
| | EsxN | UniProtKB B2HDH7 | 1-94 | Carrying C-terminal 6xHis tag |
| | MycP5 | UniProtKB A5U3G3 | 40-585 | Carrying N-terminal 8xHis tag + TEV site |
| Homo sapiens | hEGF | NCBI ADEO6646 | 2-55 | Carrying N-terminal 6xHis tag |
| | IL-3 | UniProtKB P08700 | 19-148 | Excluding signal sequence |
| | Pla2 | UniProtKB P39877 | 21-138 | Excluding signal sequence |
| Aequorea victoria | GFP | UniProtKB P42212 | 2-238 | Carrying N-terminal 6xHis tag; Substitutions in GFP: S65A/V68L/S72A |
| Saccharomyces cerevisiae | SMT3 (SUMO) | UniProtKB Q12306 | 1-98 | Carrying N-terminal 6xHis tag + thrombin cleavage site |

Example 20

IB Formation Upon Amino Acid Substitution in ssTorA in the Context of CAT

To identify sequence variants of ssTorA sustaining IB formation, ssTorA residues R11, R12, L15, Q17, L18 and G19 were substituted by various conserved and non-conserved amino acids. The resulting variants were fused to the model polypeptide of interest chloramphenicol acetyl transferase (CAT). IB formation of the resulting ssTorA/CAT fusion protein was investigated. This example demonstrates that the following substitutions sustained IB formation: R11C, R11H, R11S, R12L, R12Q, L15M, Q17E, L18I, L18V and G19V (inclusion body tags having sequence identifiers SEQ ID NO:29, 30, 31, 32, 33, 39, 40, 41, 42 and 43, respectively). This followed from an IB fractionation procedure showing that ssTorA/CAT variants carrying these substitutions efficiently formed IBs.

E. coli TOP10F' cells carrying a pIBA derivative encoding any one of CAT, ssTorA/CAT, ssTorA(R11C)/CAT, ssTorA (R11H)/CAT, ssTorA(R11S)/CAT, ssTorA(R12C)/CAT, ssTorA(R12Q)/CAT, ssTorA(L15Q)/CAT, ssTorA(L15M)/CAT, ssTorA(L15P)/CAT, ssTorA(Q17E)/CAT, ssTorA (L18H)/CAT, ssTorA(L18I)/CAT, ssTorA(L18V)/CAT, pIBA-ssTorA(L18P)/CAT, ssTorA(G19V)/CAT and ssTorA (G19D)/CAT were cultured in LB medium containing ampicillin at 37° C. When cells reached early log-phase ($OD_{660}{\approx}0.3$), cells were induced for protein synthesis by addition of anhydrotetracyclin (0.2 μg/ml). After 1 hour, two samples were taken from each culture and subjected to inclusion body fractionation as described above. The migration position of the respective fusions of ssTorA and its variants with CAT is indicated in FIG. 23.

Example 21

IB Formation Upon Amino Acid Substitution in ssTorA in the Context of TrxA

The experiments of Example 20 were repeated, using TrxA as model polypeptide of interest instead of CAT. IB formation of the resulting ssTorA/TrxA fusion proteins was investigated. In this example, the following substitutions sustained IB formation: R11C, R11H, R11S, R12L, R12Q, L15M, Q17E, L18I, L18V and G19V (inclusion body tags having sequence identifiers SEQ ID NO:29, 30, 31, 32, 33, 39, 40, 41, 42 and 43, respectively). This followed from an IB fractionation procedure showing that ssTorA/TrxA variants carrying these substitutions efficiently formed IBs. In contrast, the IB fractionation procedure showed that the following substitutions impaired IB formation compared to ssTorA/TrxA carrying a non-modified ssTorA: L15Q, L15P, L18H, L18P and G19D (fusion tags having sequence identifiers SEQ ID NO:34, 35, 36, 37 and 38, respectively).

E. coli TOP10F' cells carrying a pIBA derivative encoding any one of TrxA, ssTorA/TrxA, ssTorA(R11C)/TrxA, ssTorA(R11H)/TrxA, ssTorA(R11S)/TrxA, ssTorA(R12C)/TrxA, ssTorA(R12Q)/TrxA, ssTorA(L15Q)/TrxA, ssTorA (L15M)/TrxA, ssTorA(L15P)/TrxA, ssTorA(Q17E)/TrxA, ssTorA(L18H)/TrxA, ssTorA(L18I)/TrxA, ssTorA(L18V)/TrxA, ssTorA(L18P)/TrxA, ssTorA(G19V)/TrxA and ssTorA(G19D)/TrxA were cultured in LB medium containing ampicillin at 37° C. When cells reached early log-phase ($OD_{660}{\approx}0.4$), they were induced for protein synthesis by addition of anhydrotetracyclin (0.2 μg/ml). After 2 hours, two samples were taken from each culture and subjected to inclusion body fractionation as described above. The migration position of the respective fusions of ssTorA and its variants with TrxA is indicated in FIG. 24.

Example 22

IB Formation Upon Fusion to Truncated ssTorA and to Repeats Thereof

Figure 25A:
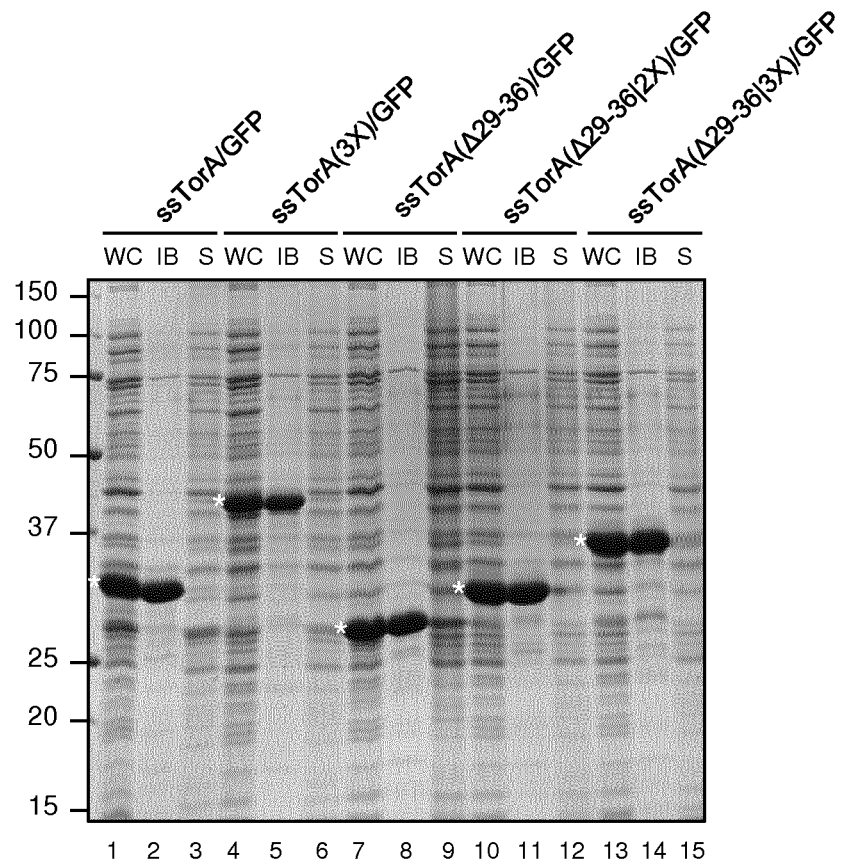
Figure 25B:
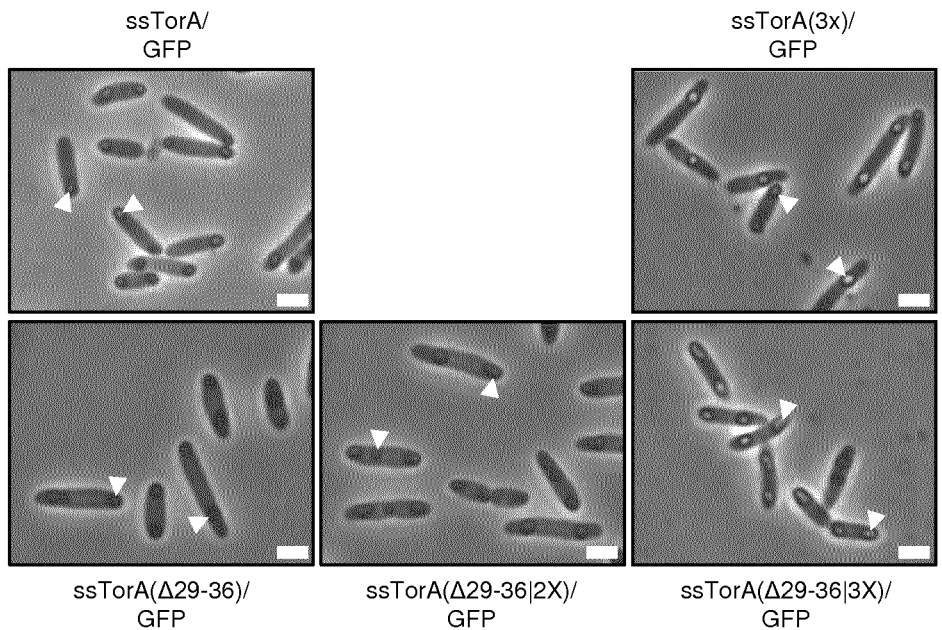

This example illustrates successful expression of GFP into IBs upon fusion to an abridged version of ssTorA denoted ssTorA[Δ29-36]$_{GFP}$ (SEQ ID NO:53). Furthermore, it showed that very efficient expression into IBs occurred upon fusion of GFP to doublet (ssTorA[Δ29-36|2×]$_{GFP}$; SEQ ID NO:54) and triplet (ssTorA[Δ29-36β×]$_{GFP:N}$; SEQ ID NO:55) repeats of ssTorA[Δ29-36]. Efficient IB formation was seen after an IB fractionation procedure, showing the almost complete recovery of expressed fusion proteins from the insoluble fraction of an *E. coli* cell lysate (FIG. 25A). Furthermore, white spherical entities representing IBs appeared in cells expressing the fusion proteins, as analyzed using phase contrast microscopy (FIG. 25B). In addition, analysis of samples from the IB fractionation procedure (FIG. 25A) showed that a fusion protein comprising GFP with ssTorA[Δ29-36|3×] at the N-terminus was expressed at a higher level (see whole cell samples) and gave a higher yield of IBs (see IB samples) compared to GFP carrying ssTorA(3×). In line with this result, phase-contrast microscopy (FIG. 25B) showed that a higher average number of IBs was observed per cell upon expression of ssTorA[Δ29-36|3×]/GFP, compared with cells expressing ssTorA(3×)/GFP. Furthermore, in cells expressing ssTorA[Δ29-36|3×]/GFP, IBs appeared larger and more prominent in phase contrast microscopy compared to IBs displayed by cells expressing ssTorA(3×)/GFP. As a control, IB fractionation data (FIG. 25C) showed that GFP has only a low tendency to form IBs when fused to the non-functional tag ssTorA(N') (SEQ ID NO:10; see Example 8). This is exemplified by the observation that only a minority of the total expressed ssTorA(N')/GFP could be recovered from the insoluble fraction of an *E. coli* lysate, while the majority of the material was detected in the soluble fraction as a lower molecular weight proteolytic product. In contrast, GFP carrying a functional ssTorA IB-forming tag was almost exclusively present in the insoluble fraction.

Figure 25C:
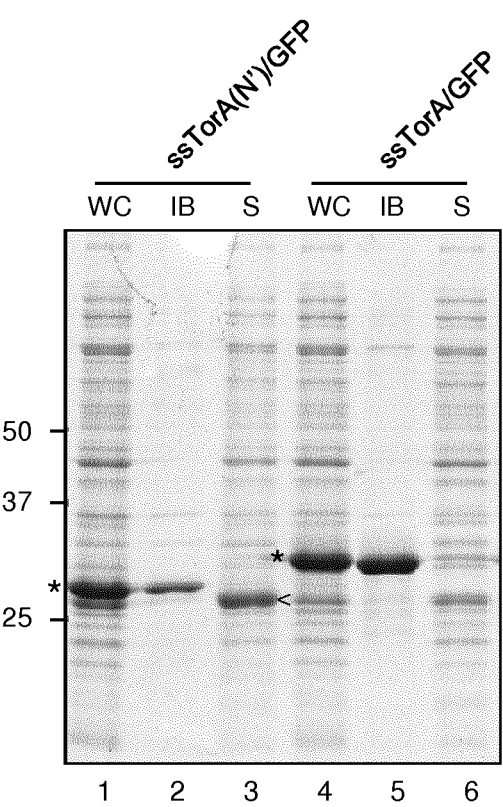

*E. coli* TOP10F' cells carrying any one of the plasmids pIBA-ssTorA[Δ29-36]/GFP, pIBA-ssTorA[Δ29-36|2×]/GFP, pIBA-ssTorA[Δ29-36|3×]/GFP, pIBA-ssTorA/GFP, pIBA-ssTorA(3×)/GFP and pIBA-ssTorA(N')/GFP were cultured in LB medium containing ampicillin at 37° C. As in Example 19, the ssTorA and ssTorA(3×) sequences used with GFP in this example carried an S38R mutation compared to SEQ ID NO:3. When cells reached early log-phase (OD$_{660}$≈0.3), cells were induced for protein synthesis by addition of anhydrotetracyclin (0.2 μg/ml). After 2 hours, samples were taken from each culture and subjected to inclusion body fractionation as described above (A and C). Selected samples were also subjected to phase-contrast microscopy (B). For microscopy analysis, harvested cells were fixed with formaldehyde (3%) and re-suspended in PBS. Cells were then photographed with an Olympus F-view II camera mounted on an Olympus BH-2 microscope through a DApo100UV PL 1.30 oil 160/0.17 objective. Resulting SDS-PAGE gels are shown in FIGS. 25A and 25C, whereas phase-contrast micrographs are shown in FIG. 25B.

Example 23

Figure 26A:
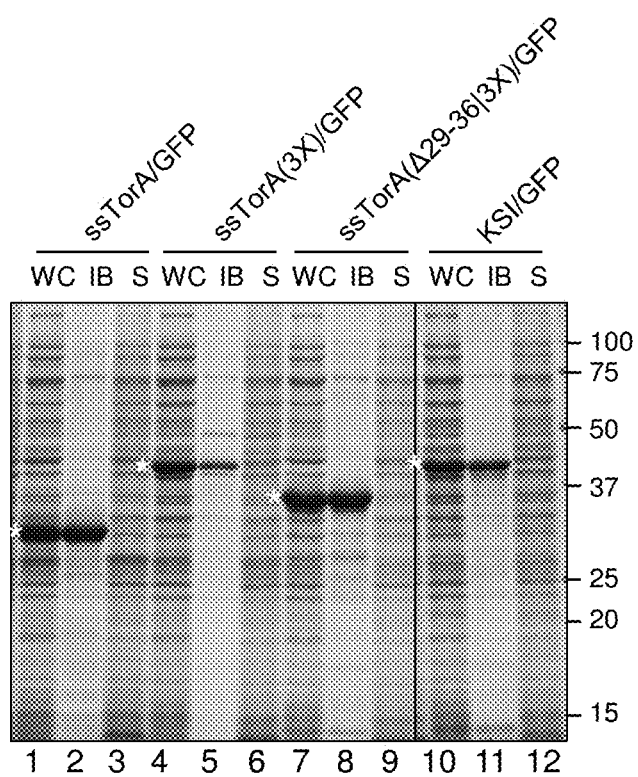
Figure 26B:
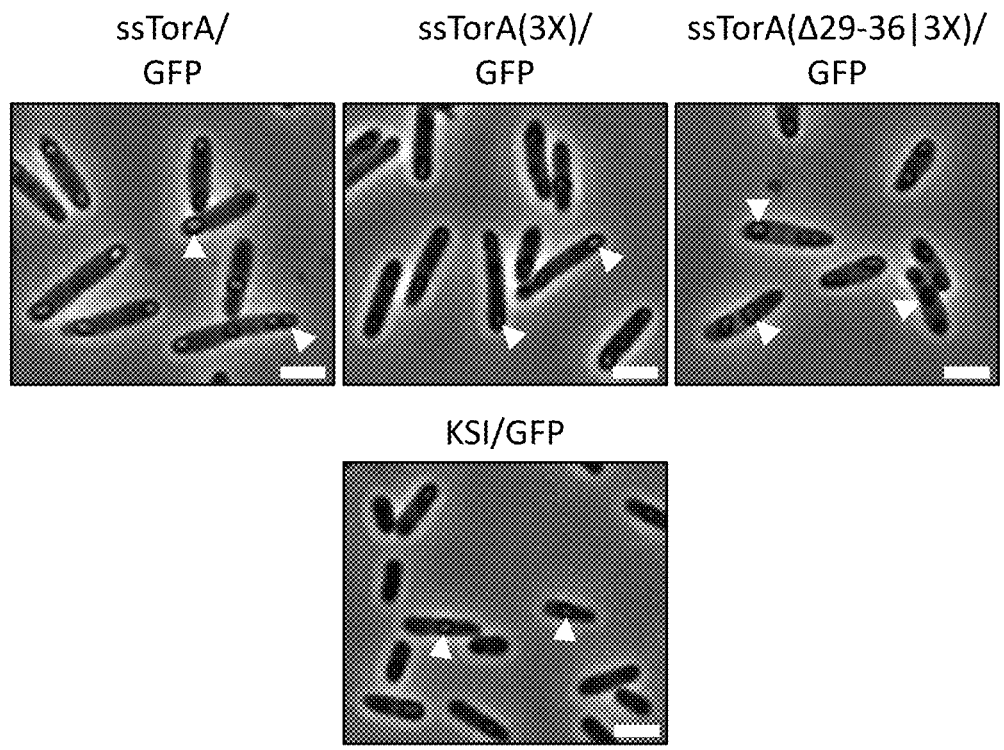

Improved IB Formation Upon Fusion to ssTorA or Derivatives Thereof Compared to KSI This example illustrates that ssTorA-derived tags were similar (ssTorA(3×)) or superior (ssTorA and ssTorA[Δ29-36|3×]) to the KSI tag as measured by their respective ability to mediate the expression of GFP in IBs using an IB fractionation procedure (FIG. 26A) and phase-contrast microscopy (FIG. 26B).

*E. coli* TOP10F' cells carrying any one of the plasmids pIBA-ssTorA/GFP, pIBA-ssTorA(3×)/GFP, pIBA-ssTorA[Δ29-36|3×]/GFP, and pIBA-KSI/GFP were cultured in LB medium containing ampicillin at 37° C. As in Example 19, the ssTorA and ssTorA(3×) sequences used with GFP in this example carried an S38R mutation compared to SEQ ID NO:3. When cells reached early log-phase (OD$_{660}$≈0.3), cells were induced for protein synthesis by addition of anhydrotetracyclin (0.2 μg/ml). After 2 hours, samples were taken from each culture and subjected to (A) inclusion body fractionation as described above and (B) phase-contrast microscopy. For microscopy analysis, harvested cells were fixed with formaldehyde (3%) and re-suspended in PBS. Cells were then photographed with an Olympus F-view II camera mounted on an Olympus BH-2 microscope through a DApo100UV PL 1.30 oil 160/0.17 objective. Resulting SDS-PAGE gel and phase-contrast micrograph are shown in FIGS. 26A and 26B, respectively.

Example 24

IB Formation Upon Fusion to Tandem Repeats of Truncated ssTorA

This example illustrates successful expression of GFP in inclusion bodies when fused to three repeats of ssTorA at both the N- and C-termini simultaneously. Furthermore, the example demonstrates very efficient IB formation of GFP, both when fused to three repeats of ssTorA[Δ29-36] (ssTorA[Δ29-36)|3×]; SEQ ID NO:57) at the N-terminus and to three repeats of ssTorA at the C-terminus, and when fused to three repeats of ssTorA[Δ29-36] at both termini. An IB fractionation procedure showed that all three constructs were almost exclusively recovered from the insoluble fraction upon expression in *E. coli*, demonstrating IB formation. Moreover, the example suggests that use of ssTorA[Δ29-36)|3×] as an N-terminal (ssTorA[Δ29-36)|3×]; SEQ ID NO:57) and C-terminal (ssTorA[Δ29-36)|3×]$_{GFP:C}$; SEQ ID NO:56) IB-tag has benefits over the use of ssTorA(3×). This follows from the observation that GFP carrying ssTorA[Δ29-36)|3×] at both N- and C-termini reached a higher expression level and yield of fusion protein compared to a counterpart carrying ssTorA[Δ29-36)|3×] at the N-terminus and ssTorA (3×) at the C-terminus. In turn, this latter GFP construct produced more insoluble fusion protein compared to a version carrying ssTorA(3×) at both termini, implying an additive effect of ssTorA[Δ29-36)|3×] on fusion protein expression and IB formation.

*E. coli* TOP10F' cells carrying any one of the plasmids pIBA-ssTorA(3×)/GFP/ssTorA(3×), pIBA-ssTorA[Δ29-36|3×]/GFP/ssTorA(3×) and pIBA-ssTorA[Δ29-36|3×]/GFP/ssTorA[Δ29-36|3×] were cultured in LB medium containing ampicillin at 37° C. When cells reached early log-phase (OD$_{660}$≈0.3), cells were induced for protein synthesis by addition of anhydrotetracyclin (0.2 μg/ml). After 2 hours, samples were taken from each culture and subjected to inclusion body fractionation as described above. The resulting SDS-PAGE gel is shown in FIG. 27.

Example 25

IB Formation Upon Fusion of Tandem Repeats of Truncated ssTorA to Various Model Proteins This example illustrates very efficient IB formation upon fusion of ssTorA[Δ29-36|3×] (SEQ ID NO:57) at the N-terminus of model proteins TrxA, MBP, CAT and hEGF. Using the IB fractionation procedure described in General procedures, it is shown that the fusion proteins were almost exclusively recovered from the IB containing insoluble fraction upon expression in E. coli, indicating very efficient IB formation. Furthermore, rather prominent IBs could be detected in cells expressing the fusion proteins using phase-contrast microscopy.

This example also illustrates an advantageous effect of the use of ssTorA[Δ29-36│3×] as an IB tag compared to ssTorA(3×). The IB fractionation assay shows that fusion proteins ssTorA[Δ29-36│3×]/TrxA and ssTorA[Δ29-36│3×]/MBP were expressed in the insoluble fraction to a considerably higher degree than their counterparts carrying ssTorA(3×). Moreover, phase-contrast microscopy shows much larger IBs in cells expressing ssTorA[Δ29-36│3×]/TrxA and ssTorA[Δ29-36│3×]/MBP, as compared with cells expressing TrxA and MBP fused to ssTorA(3×).

Figure 28A:
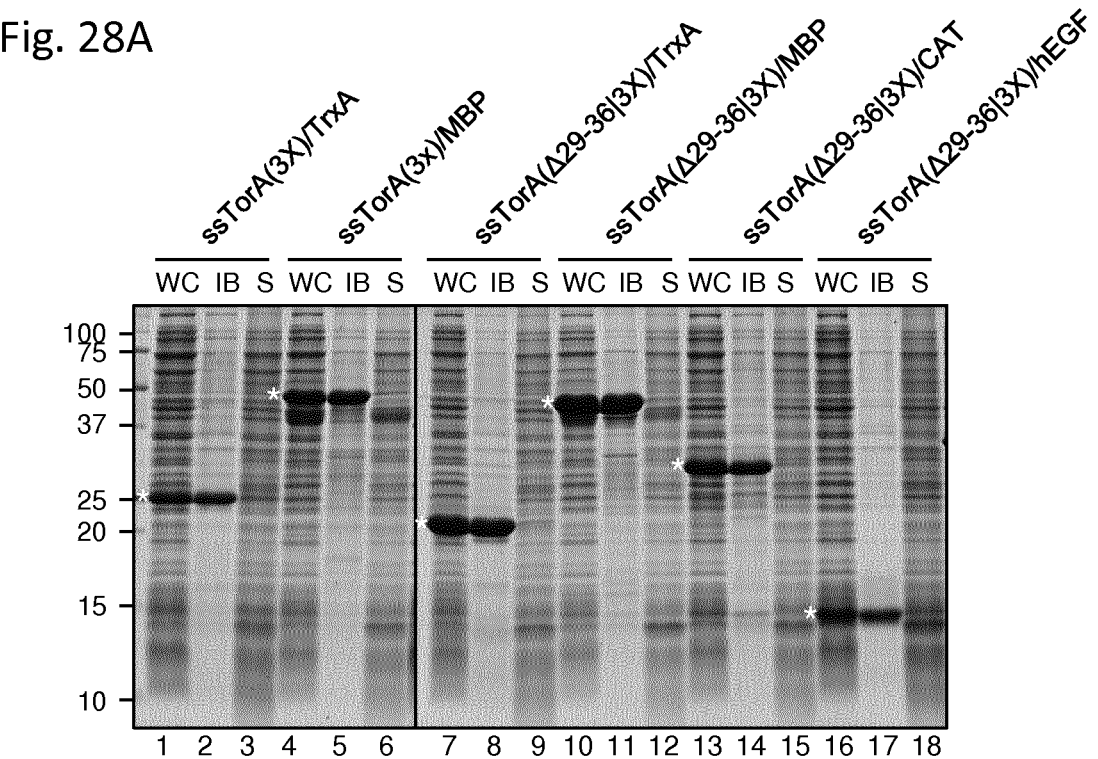
Figure 28B:
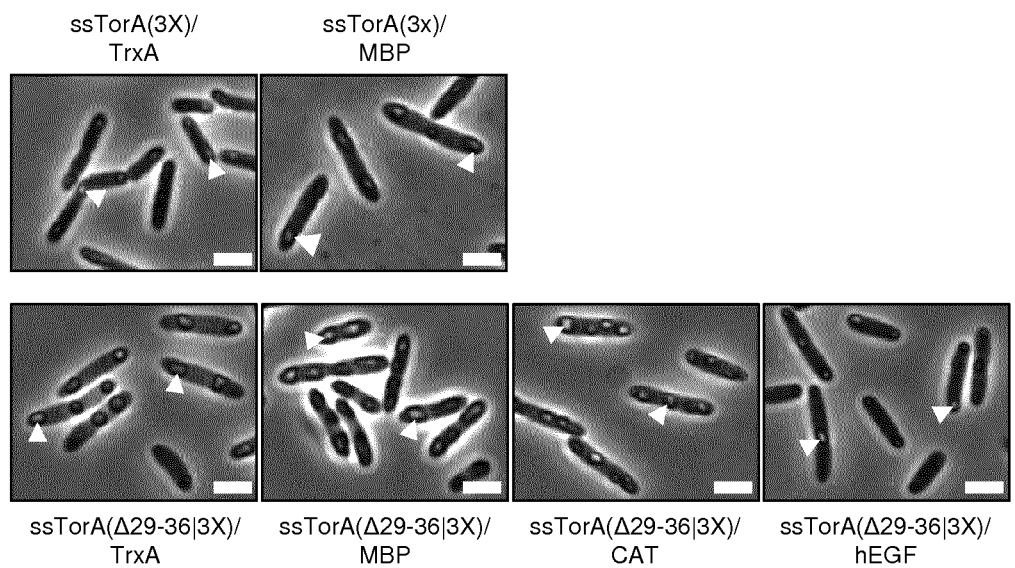

E. coli TOP10F' cells carrying any one of the plasmids pIBA-ssTorA(3×)/TrxA, pIBA-ssTorA(3×)/MBP, pIBA-ssTorA[Δ29-36│3×]/TrxA, pIBA-ssTorA[Δ29-36│3×]/MBP, pIBA-ssTorA[Δ29-36│3×]/CAT and pIBA-ssTorA[Δ29-36│3×]/hEGF were cultured in LB medium containing ampicillin at 37° C. When cells reached early log-phase ($OD_{660} \approx 0.3$), cells were induced for protein synthesis by addition of anhydrotetracyclin (0.2 μg/ml). After 2 hours, samples were taken from each culture and subjected to (A) inclusion body fractionation as described above and (B) phase-contrast microscopy. For microscopy analysis, harvested cells were fixed with formaldehyde (3%) and resuspended in PBS. Cells were then photographed with an Olympus F-view II camera mounted on an Olympus BH-2 microscope through a DApo100UV PL 1.30 oil 160/0.17 objective. Resulting SDS-PAGE gel and phase-contrast micrograph are shown in FIGS. 28A and 28B, respectively.

The invention claimed is:
1. A fusion polypeptide comprising an inclusion body tag fused to at least one polypeptide of interest, wherein said inclusion body tag comprises an inclusion body forming (IBF) amino acid sequence selected from:
   i) $X_{14}X_{15}AX_{17}X_{18}X_{19}$GLTVAGMLG (SEQ ID NO:1) wherein, independently from each other,
      $X_{14}$ is selected from F and Y;
      $X_{15}$ is selected from L and M;
      $X_{17}$ is selected from Q and E;
      $X_{18}$ is selected from L, V and I; and
      $X_{19}$ is selected from G and V; and
   ii) an amino acid sequence which has at least 71% identity to the sequence defined in i);
wherein:
   (a) the fusion polypeptide comprises two or more of the inclusion body tags;
   (b) the inclusion body tag is C-terminal to said polypeptide of interest; or
   (c) the inclusion body tag comprises the amino acid sequence of SEQ ID NO: 3 or SEQ ID NO:44 lacking one or more of the amino acids corresponding to positions 29-36 of SEQ ID NO: 3 or SEQ ID NO:44.

2. The fusion polypeptide according to claim 1, in which said IBF is selected from:
   iii) $SX_{11}X_{12}RX_{14}X_{15}AX_{17}X_{18}X_{19}$GLTVAGMLG (SEQ ID NO:2)
      wherein, independently from each other,
      $X_{11}$ is selected from R, C, K, A, S and H; and
      $X_{12}$ is selected from R, Q, K, A and L;
and
   iv) an amino acid sequence which has at least 77% identity to the sequence defined in iii).

3. The fusion polypeptide according to claim 1, wherein said inclusion body tag comprises the amino acid sequence:
   $X_2X_3X_4$-Z-IBF
wherein, independently from each other,
   $X_2$, $X_3$ and $X_4$ are each individually selected from N, A, K and T; and
   Z is a spacer sequence comprising 0-10 amino acids.

4. The fusion polypeptide according to claim 1, in which said inclusion body tag(s) is(are) fused to said polypeptide of interest at the N-terminus thereof.

5. The fusion polypeptide according to claim 1, in which said inclusion body tag(s) is(are) fused to said polypeptide of interest at the C-terminus thereof.

6. The fusion polypeptide according to claim 1, comprising two or more copies of the inclusion body tag, whose sequences may be identical or different.

7. The fusion polypeptide according to claim 6, in which at least one inclusion body tag is fused to the N-terminus of said polypeptide of interest and at least one inclusion body tag is fused to the C-terminus of said polypeptide of interest.

8. The fusion polypeptide according to claim 1, further comprising at least one cleavage element for separation of an inclusion body tag from the at least one polypeptide of interest.

9. The fusion polypeptide according to claim 1, with the proviso that said inclusion body tag does not comprise the amino acid sequence MNNNDLFQASRRRFLAQLG-GLTVAGMLGPSLLTPRRATA (SEQ ID NO:44).

10. An inclusion body comprising a fusion polypeptide according to claim 1.

11. A nucleic acid molecule comprising a coding sequence for the fusion polypeptide of claim 1.

12. The nucleic acid of claim 11, wherein the nucleic acid further comprises a promoter and terminator, wherein the promoter and terminator are operably linked to the coding sequence.

13. An expression vector comprising the nucleic acid of claim 12.

14. A microbial host cell comprising the nucleic acid of claim 12.

15. A method of producing a fusion polypeptide, comprising:
   i) providing a microbial host cell according to claim 14, and
   ii) culturing said cell under conditions wherein said fusion polypeptide is expressed and inclusion bodies thereof are formed.

16. An inclusion body produced by a method according to claim 15.

17. A fusion polypeptide according to claim 1, wherein said fusion polypeptide comprises two or more of the inclusion body tags.

18. A fusion polypeptide according to claim 1, the inclusion body tag is C-terminal to said polypeptide of interest.

19. A fusion polypeptide according to claim 1, wherein the inclusion body tag comprises the amino acid sequence of SEQ ID NO:44 lacking one or more of the amino acids corresponding to positions 29-36 of SEQ ID NO:44.

20. A fusion polypeptide according to claim 1, wherein the inclusion body tag comprises the amino acid sequence of SEQ ID NO:3 lacking one or more of the amino acids corresponding to positions 29-36 of SEQ ID NO:3.

* * * * *

UNITED STATES PATENT AND TRADEMARK OFFICE
CERTIFICATE OF CORRECTION

PATENT NO. : 11,124,555 B2
APPLICATION NO. : 16/480658
DATED : September 21, 2021
INVENTOR(S) : Wouter Simon Petrus Jong et al.

It is certified that error appears in the above-identified patent and that said Letters Patent is hereby corrected as shown below:

In the Specification

In Column 2, Line 60, please change "1-galactosidase" to --β-galactosidase--;

In Column 31, Line 6, please change "pIBA-ssTorAIIL-3" to --pIBA-ssTorA/IL-3--;

In Column 31, Line 7, please change "pIBA-ssDsbAIIL-3" to --pIBA-ssDsbA/IL-3--;

In Column 31, Line 25, please change "ssTorAIIL" to --ssTorA/IL-3--;

In Column 31, Line 32, please change "pIBA-ssTorAIIL-3" to --pIBA-ssTorA/IL-3--;

In Column 35, Line 14, please change "A25-36" to --Δ25-36--;

In Column 39, Line 7, please change "P88093" to --O88093--.

Signed and Sealed this
Ninth Day of November, 2021

Drew Hirshfeld
*Performing the Functions and Duties of the*
*Under Secretary of Commerce for Intellectual Property and*
*Director of the United States Patent and Trademark Office*